US010321941B2

United States Patent
Diao et al.

(10) Patent No.: US 10,321,941 B2
(45) Date of Patent: Jun. 18, 2019

(54) INTRAMEDULLARY REPAIR SYSTEM FOR BONE FRACTURES

(71) Applicant: EndoOrthopaedics, Inc., San Francisco, CA (US)

(72) Inventors: Edward Diao, San Francisco, CA (US); Harold F. Carrison, Pleasanton, CA (US)

(73) Assignee: ENDOORTHOPAEDICS, INC., San Francisco, CA (US)

( * ) Notice: Subject to any disclaimer, the term of this patent is extended or adjusted under 35 U.S.C. 154(b) by 0 days.

(21) Appl. No.: 15/297,121

(22) Filed: Oct. 18, 2016

(65) Prior Publication Data

US 2017/0035471 A1    Feb. 9, 2017

Related U.S. Application Data

(63) Continuation of application No. 12/622,309, filed on Nov. 19, 2009, now Pat. No. 9,474,556.
(Continued)

(51) Int. Cl.
*A61B 17/72*    (2006.01)
*A61B 17/68*    (2006.01)

(52) U.S. Cl.
CPC .......... *A61B 17/7258* (2013.01); *A61B 17/68* (2013.01); *A61B 17/72* (2013.01)

(58) Field of Classification Search
CPC . A61B 17/80–17/8095; A61B 17/72–17/7291; A61F 2/38–2/389
See application file for complete search history.

(56) References Cited

U.S. PATENT DOCUMENTS 3,842,825 A * 10/1974 Wagner ............... A61B 17/746
                                                        606/101
4,016,874 A *  4/1977 Maffei .................. A61B 17/72
                                                         606/62
(Continued)

FOREIGN PATENT DOCUMENTS

CN        1909848 A    2/2007
CN     101249015 A    8/2008
(Continued)

OTHER PUBLICATIONS

Chinese Notification of the First Office Action dated Mar. 13, 2013 for Patent Application No. 200980154919.3 (11 pages).
(Continued)

*Primary Examiner* — Nicholas J Plionis
*Assistant Examiner* — Steven J Cotroneo
(74) *Attorney, Agent, or Firm* — Dorsey & Whitney LLP

(57) ABSTRACT

An intramedullary bone fixation device is disclosed herein. The device includes a first longitudinally extending member, a second longitudinally extending member, and a coupling member. The first longitudinally extending member includes a connector end and a bone engagement end opposite the connector end. The second longitudinally extending member includes a connector end and a bone engagement end opposite the connector end. The coupling member is configured to engage the connector ends of the respective longitudinally extending members, thereby coupling the first longitudinally extending member to the second longitudinally extending member. The device may be provided in an kit form at least partially unassembled. The device may be delivered into a fracture and fully assembled within the fracture or adjacent bone via percutaneous or minimally invasive surgical procedures. The device, on account of its
(Continued)

configuration and assembly, may be considered modular in some cases.

13 Claims, 50 Drawing Sheets

Related U.S. Application Data

(60) Provisional application No. 61/116,074, filed on Nov. 19, 2008.

(56) References Cited

U.S. PATENT DOCUMENTS

| | | | |
|---|---|---|---|
| 4,190,044 A | 2/1980 | Wood | |
| 4,384,373 A * | 5/1983 | Sivash | A61F 2/28 623/23.45 |
| 4,787,907 A * | 11/1988 | Carignan | A61F 2/28 623/23.44 |
| 4,938,768 A * | 7/1990 | Wu | A61B 17/68 403/307 |
| 4,990,161 A * | 2/1991 | Kampner | A61F 2/30767 623/18.11 |
| 5,123,926 A * | 6/1992 | Pisharodi | A61F 2/441 606/247 |
| 5,263,955 A * | 11/1993 | Baumgart | A61B 17/7216 606/62 |
| 5,358,524 A * | 10/1994 | Richelsoph | A61F 2/36 403/109.4 |
| 5,507,825 A * | 4/1996 | Frei | A61B 17/1746 623/22.36 |
| 5,993,486 A * | 11/1999 | Tomatsu | A61F 2/08 623/13.11 |
| 6,113,638 A * | 9/2000 | Williams | A61F 2/442 128/898 |
| 6,375,684 B1 * | 4/2002 | Kriek | A61B 17/1666 623/23.39 |
| 6,454,810 B1 * | 9/2002 | Lob | A61B 17/72 606/62 |
| 6,730,090 B2 | 5/2004 | Orbay et al. | |
| 6,793,659 B2 | 9/2004 | Putnam | |
| 7,060,067 B2 | 6/2006 | Needham et al. | |
| 7,141,067 B2 * | 11/2006 | Jones | A61F 2/28 606/62 |
| 7,198,642 B2 * | 4/2007 | Hazebrouck | A61F 2/28 606/62 |
| 7,291,152 B2 | 11/2007 | Abdou | |
| 7,704,279 B2 * | 4/2010 | Moskowitz | A61B 17/0642 606/289 |
| 7,828,802 B2 | 11/2010 | Levy et al. | |
| 7,846,188 B2 * | 12/2010 | Moskowitz | A61B 17/0642 606/279 |
| 2003/0033019 A1 | 2/2003 | Lob | |
| 2004/0097930 A1 | 5/2004 | Justis et al. | |
| 2004/0243138 A1 | 12/2004 | Cole | |
| 2005/0102031 A1 * | 5/2005 | Leonard | A61F 2/3836 623/20.21 |
| 2005/0113924 A1 | 5/2005 | Buttermann | |
| 2005/0159749 A1 * | 7/2005 | Levy | A61B 17/68 606/62 |
| 2005/0278036 A1 | 12/2005 | Leonard et al. | |
| 2006/0009767 A1 | 1/2006 | Douglas | |
| 2006/0095136 A1 * | 5/2006 | McLuen | A61F 2/4455 623/23.47 |
| 2006/0149257 A1 | 7/2006 | Orbay et al. | |
| 2006/0235414 A1 * | 10/2006 | Lim | A61F 2/4425 623/17.14 |
| 2006/0247622 A1 | 11/2006 | Maughan et al. | |
| 2007/0055274 A1 | 3/2007 | Appenzeller et al. | |
| 2007/0100342 A1 | 5/2007 | Green et al. | |
| 2007/0118129 A1 * | 5/2007 | Fraser | A61F 2/0811 606/71 |
| 2007/0142921 A1 * | 6/2007 | Lewis | A61B 17/86 623/22.36 |
| 2007/0191854 A1 | 8/2007 | Grim | |
| 2007/0233146 A1 | 10/2007 | Henniges et al. | |
| 2007/0299532 A1 * | 12/2007 | Rhodes | A61F 2/389 623/20.32 |
| 2008/0027559 A1 | 1/2008 | Crowninshield et al. | |
| 2008/0147075 A1 | 6/2008 | Bonutti | |
| 2008/0161805 A1 | 7/2008 | Saravia et al. | |
| 2008/0208261 A1 | 8/2008 | Medoff | |
| 2008/0234676 A1 | 9/2008 | Schulze et al. | |
| 2009/0118766 A1 | 5/2009 | Park et al. | |
| 2010/0137862 A1 | 6/2010 | Diao et al. | |
| 2010/0137987 A1 | 6/2010 | Diao et al. | |

FOREIGN PATENT DOCUMENTS

| | | |
|---|---|---|
| DE | 19912696 A1 | 10/2000 |
| JP | H08502662 A | 3/1996 |
| WO | 98/19617 A1 | 5/1998 |
| WO | 2006078662 A1 | 7/2006 |

OTHER PUBLICATIONS

Chinese Search Report for Patent Application No. 200980154919.3, dated Mar. 5, 2013 (5 pages).
European Search Report for European Patent Application No. 09828240.3, dated Jun. 16, 2014 (8 pages).
Japanese Office Action for Patent Application No. 2011-537628, dated Jun. 11, 2013 (10 pages).
International Search Report for International Application No. PCT/US2009/065200, dated Jan. 21, 2010 (2 pages).
International Search Report for International Application No. PCT/US2009/065206, dated Jan. 26, 2010 (2 pages).
Japanese Final Office Action for Patent Application No. 2011-537628, dated Apr. 22, 2014 (10 pages).

* cited by examiner

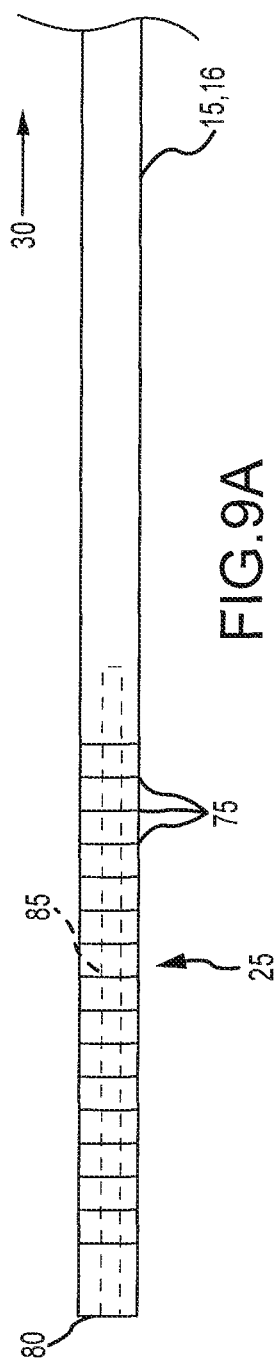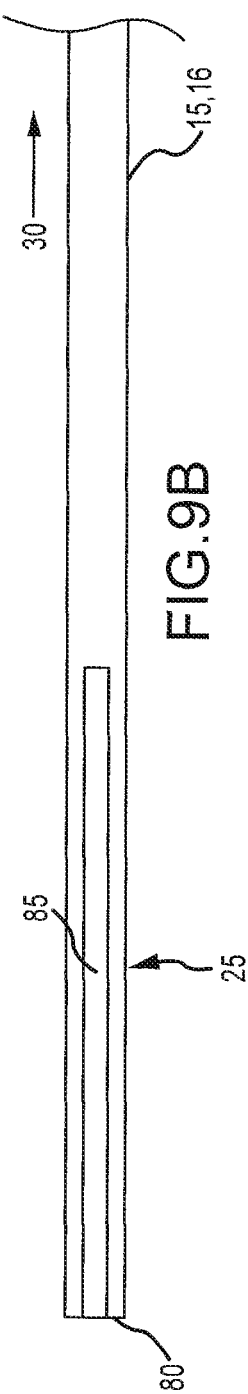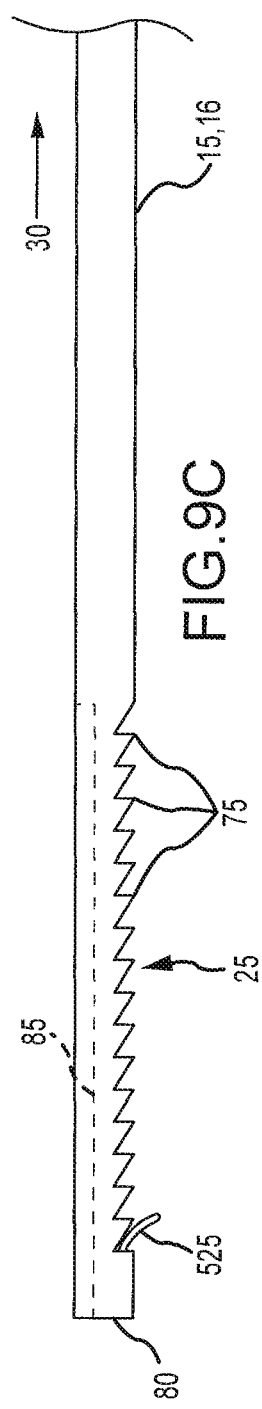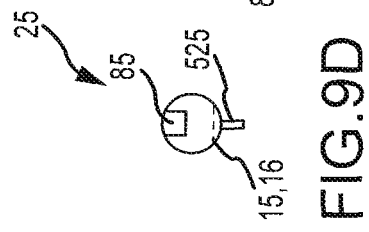

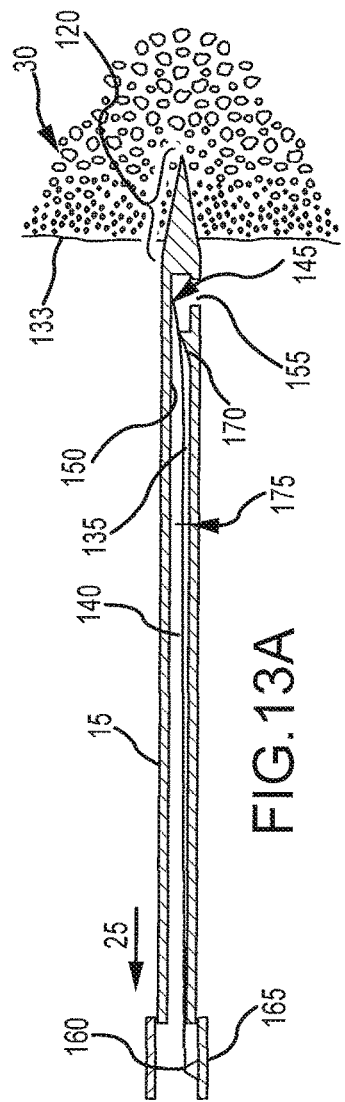
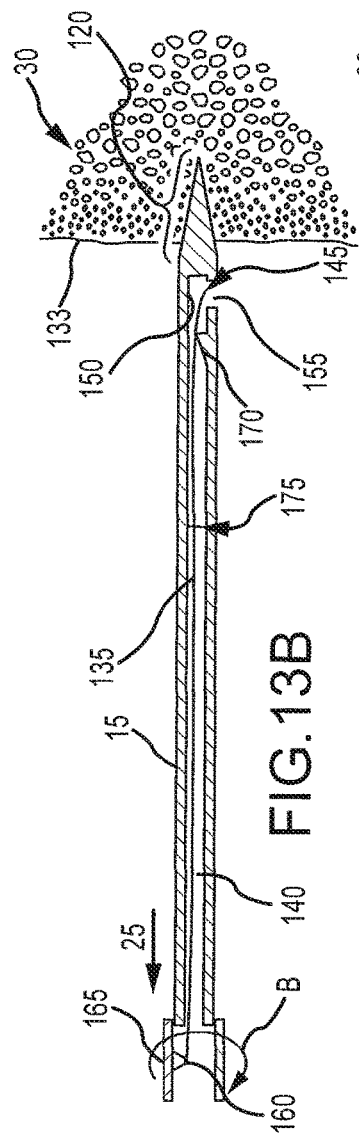
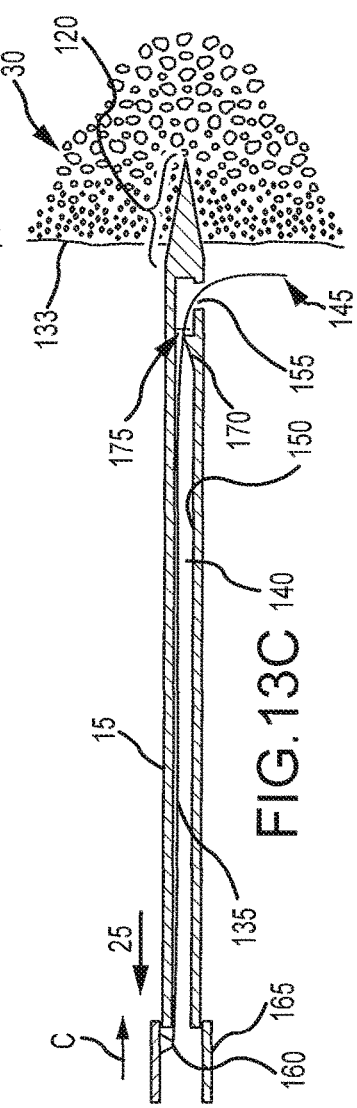

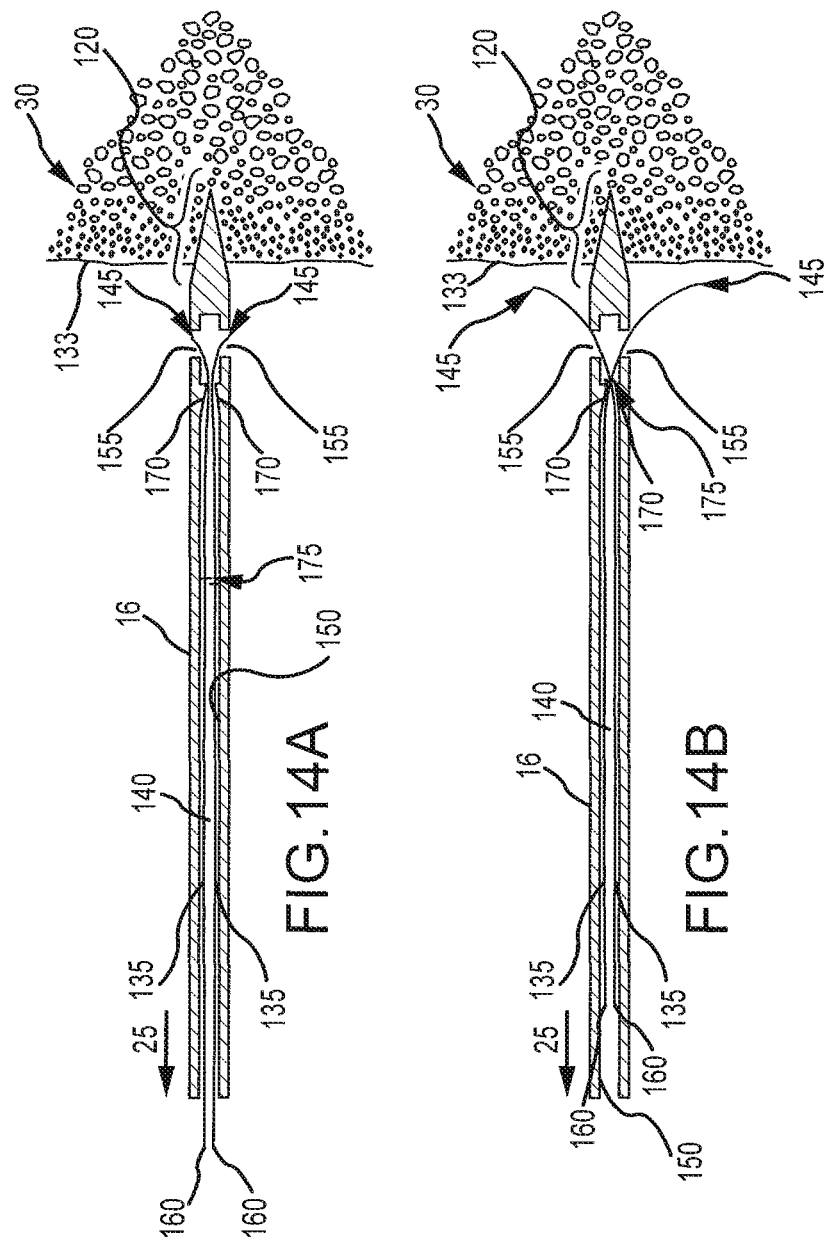

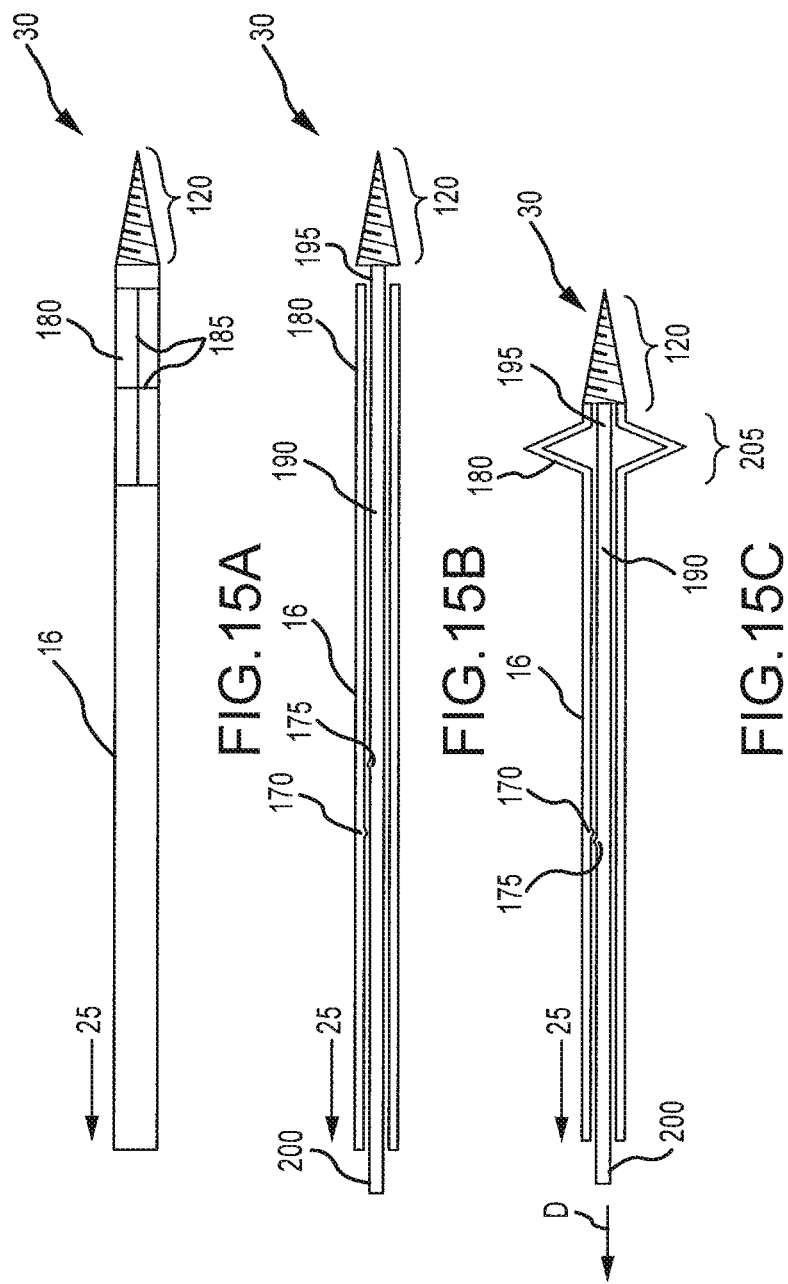

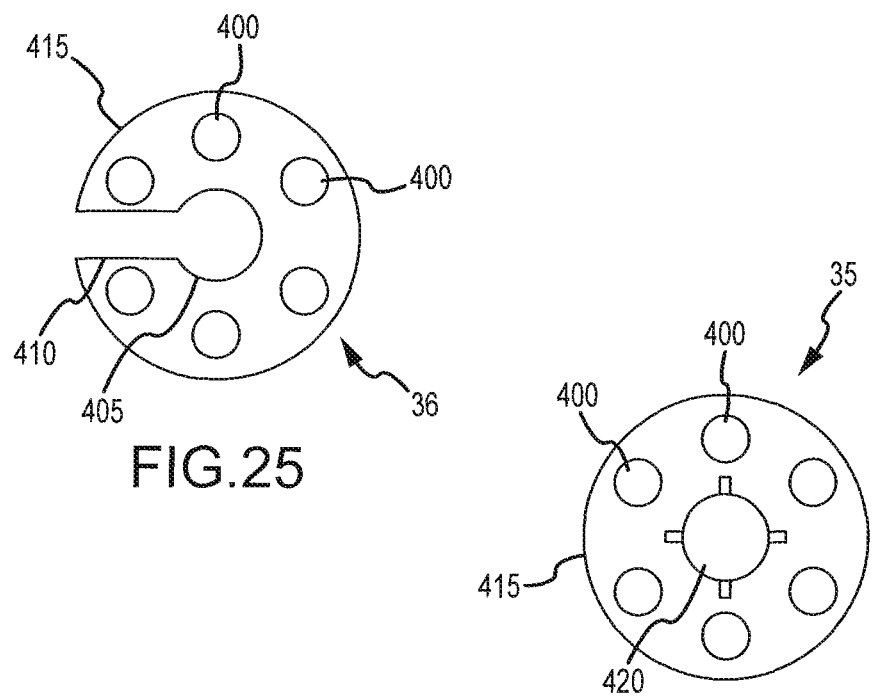
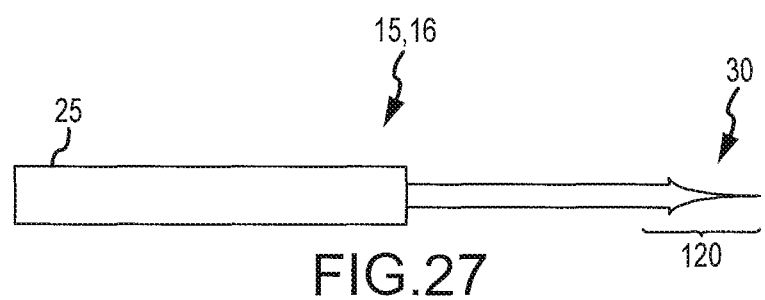
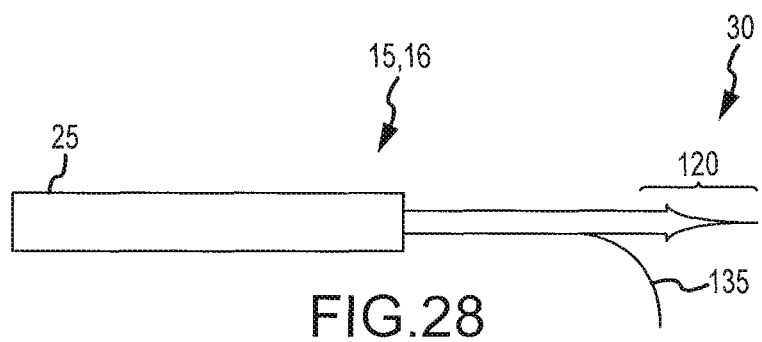

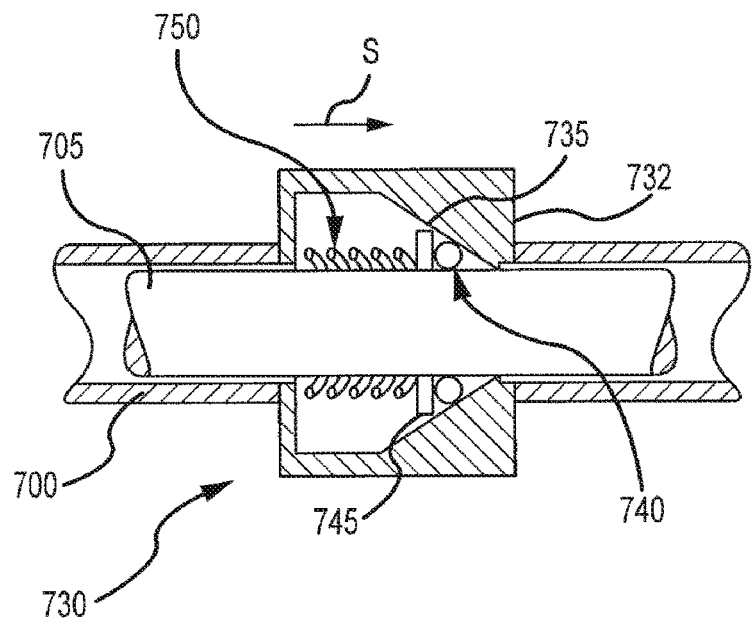
FIG.69
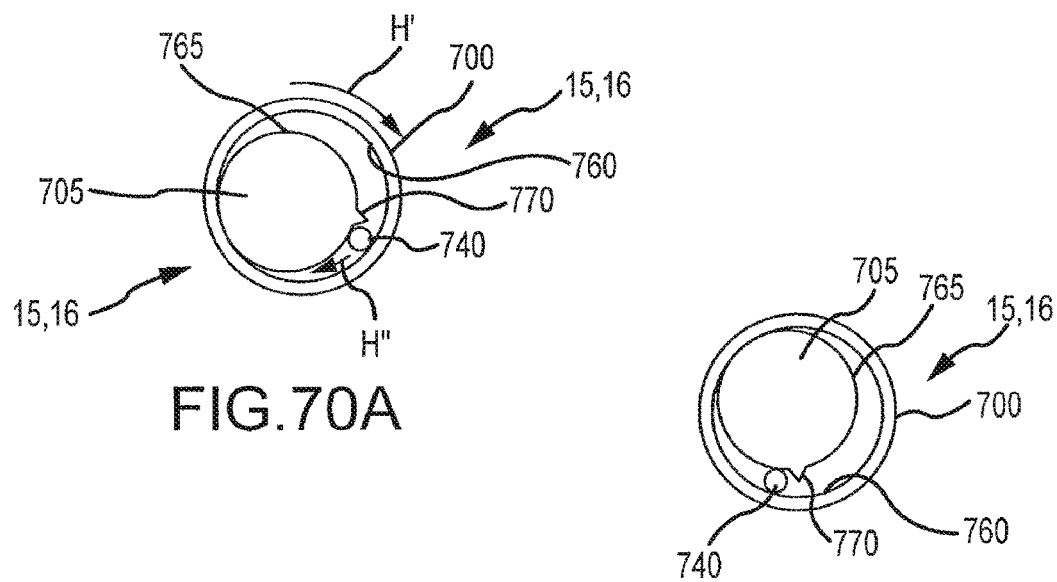
FIG.70A
FIG.70B

INTRAMEDULLARY REPAIR SYSTEM FOR BONE FRACTURES

CROSS REFERENCE TO RELATED APPLICATIONS

The present application is a continuation of co-pending U.S. patent application Ser. No. 12/622,309 filed 19 Nov. 2009 entitled "Intramedullary repair system for bone fractures," which claims priority under 35 U.S.C. § 119 to U.S. provisional patent application No. 61/116,074 filed 19 Nov. 2008 entitled "Intramedullary fixation device with universal adjuster and method of using." The disclosure of each of these applications is hereby incorporated herein by reference in its entirety.

The present application is also related to U.S. patent application Ser. No. 12/622,320 filed 19 Nov. 2009 entitled "Intramedullary repair system for vertebra fractures," the disclosure of which is hereby incorporated herein by reference in its entirety.

TECHNICAL FIELD

The present invention relates to orthopedic apparatus and methods. More specifically, the present invention relates to intramedullary bone fracture repair devices and methods.

BACKGROUND

Certain types and severities of bone fractures require orthopedic surgery to properly align the fracture and to implant an artificial structure across the fracture to maintain the proper alignment and reinforce the fractured bone as the fracture heals. An example of a fracture that often demands the implantation of an artificial structure across the fracture is a fracture at the distal radius, which is one of the most common sites of bone fracture and is the most common fracture site in the upper extremity, accounting for approximately 10% of all fractures in adults. A distal radial fracture often occurs as a compression injury that is sustained while the patient experiences axial loading of the bone as a result of a fall. This type of fracture is particularly common in elderly patients due to osteoporosis and in younger, physically active patients.

In 2004, there were over 1.5 million distal radial fractures, and this number is expected to increase steeply as the population ages. However, despite this frequency, the methods available to repair the distal radius are limited and prone to a variety of complications that limit the clinical outcome following definitive treatment. For example, open reduction of the distal radius enables the surgeon to most confidently realign the distal radius bone fragments and restore stability to the joint. This method is required in approximately 25% of patients (~375,000/year). Unfortunately, current practice requires the surgeon to disrupt the soft tissues over a 10 cm distance adjacent to the joint to expose the bone for placement of hardware to stabilize the fracture, such as a dorsal or volar locking plate. Thus, improved bone stability is achieved by sacrificing the integrity of an extensive tendon, ligament and neuromuscular network that is critical for proper wrist function. Also, plating techniques external to the bone can become a source of irritation to the soft tissue, including tendons and peripheral nerves. Such soft tissue irritation necessitates revision surgeries in over 30% of patients to remove the offending plates. This results in additional cost, disability and surgical risk to the patient. Furthermore, since plates are load-shielding as opposed to load-sharing, plates do not promote the bone remodeling that is necessary for better long-term strength of the bone tissue. Similar issues exist with respect to the treatment of other types of fractures (e.g., fractures in long bones, such as, for example, the proximal ulna and radius at the elbow, the distal humerus at the elbow, the proximal humerus at the shoulder, the proximal femur at the hip, the distal femur and proximal tibia at the knee, the distal tibia and other ankle and foot bones, the clavicle, and the spine, etc.)

There is a need in the art for devices and methods that offer improved outcomes for the treatment of bone fractures, resulting in better aligned and stronger healed fractures, reducing the likelihood of a revision being necessary, and reducing the damage to soft tissue adjacent the fracture. There is also a need in the art for devices and methods that offer a reduction in the surgical time required for the treatment of bone fractures.

SUMMARY

An intramedullary bone fixation device is disclosed herein. In one embodiment, the device includes a first longitudinally extending member, a second longitudinally extending member, and a coupling member. The first longitudinally extending member includes a connector end and a bone engagement end opposite the connector end. The second longitudinally extending member includes a connector end and a bone engagement end opposite the connector end. The coupling member is configured to engage the connector ends of the respective longitudinally extending members, thereby coupling the first longitudinally extending member to the second longitudinally extending member. The device may be provided in an kit form at least partially unassembled. The device may be delivered into a fracture and fully assembled within the fracture or adjacent bone via percutaneous or minimally invasive surgical procedures. The device, on account of its configuration and assembly, may be considered modular in some cases.

In another embodiment, the intramedullary bone fixation device may include a first bone engaging means for engaging a bone, a second bone engaging means for engaging a bone, and a coupling means for coupling together the first and second bone engaging means. The first and second bone engaging means may each include connector means for acting with the coupling means in coupling the together the first and second bone engaging means. Each connector means may include interdigitation means for forming an interdigitate relationship between the coupling means and the connector means. Each bone engaging means may include a free end and an anchor means at or near the free end for anchoring the free end in adjacent bone. Each bone engaging means may be extendable in length and include fixing means for fixing the length of the bone engaging means once adjusted as desired.

A bone fracture repair device is also disclosed herein. In one embodiment, the device includes a hub and at least two intramedullary rods radially extending from the hub. The hub may be configured such that at least one of the rods is securable at a selected radial position over a range of selectable radial positions extending over at least a portion of an edge boundary of the hub. The selectable positions may be incremental. For example, the incremental selectable positions may have increments of approximately five degrees or, in other embodiment, increments of greater or lesser than five degrees. In some embodiments, the hub may be configured such that at least one of the rods is securable at a selected extension position over a range of selectable extension positions, the selected extension position being the extent to which the at least one of the rods extends beyond an edge boundary of the hub. In some embodiments, the at least one of the rods is configured to allow an overall length of the at least one of the rods to be adjusted. The device may be configured for intramedullary implantation. The device may also be configured for percutaneous or minimally invasive surgical delivery.

Also disclosed herein is a bone fracture repair device. In one embodiment, the device includes a first bone engagement member, a second bone engagement member, a coupling member. The coupling member is configured to secure the first and second bone engagement members together in a variety of angular relationships to each other. For example, the angular relationship between engagement bone engagement members may be between approximately zero degrees and approximately 180 degrees. The bone engagement members and coupling member may be configured for percutaneous delivery and intramedullary implantation. In one embodiment, the coupling member is configured to secure at least one of the bone engagement members in a variety of extents to which the at least one of the bone engagement members extends from the coupling member. In one embodiment, the at least one of the bone engagement members is configured to allow an overall length of the at least one of the bone engagement member to be adjusted. In one embodiment, the bone engagement members include intramedullary rods and the coupling member includes a hub.

Also disclosed herein is a method of treating a bone fracture. In one embodiment, the method includes: intramedullarly implanting a first longitudinally extending member including a first bone anchor end and a first connector end opposite the first bone anchor end, wherein the first bone anchor end anchors in bone material on a first side of the bone fracture; intramedullarly implanting a second longitudinally extending member including a second bone anchor end and a second connector end opposite the second bone anchor end, wherein the second bone anchor end anchors in bone on a second side of the bone fracture opposite the first side; intramedullarly implanting a coupling member near the fracture; and connecting the first connector end to the coupling member and connecting the second connector end to the coupling member. Depending on the embodiment, the method may also include any of the following. For example, at least one of the longitudinally extending members may include an intramedullary rod. The implantation of one or more of the longitudinally extending members and/or the coupling member may be achieved via minimally invasive surgical procedures. In causing the bone anchor ends to anchor in bone material, the aspects of the bone anchor ends may be caused to expand into the bone material. The length of the longitudinally extending members may be adjusted as needed to facilitate the implantation of the longitudinally extending members and the coupling thereof to the coupler member.

Also disclosed herein is a bone fracture repair device, which, in one embodiment, includes a proximal hub, a distal hub, an intermediate intramedullary rod extending between the hubs, a proximal intramedullary rod extending proximally from the proximal hub, and a distal intramedullary rod extending distally from the distal hub. Such a multiple hub bone fracture repair device may be employed to repair fractures in, for example, long bones where a first fracture is at a proximal end of the bone and another fracture is at another end of the bone, the hubs being located at respective fracture locations and the intermediate intramedullary rod extending through the bone to secure the hubs together.

In another embodiment, a bone fracture repair device may include a hub configured to engage bone material and an intramedullary rod extending from the hub.

In yet another embodiment, a bone fracture repair device may include a first intramedullary rod, a second intramedullary rod, and an engagement member that is configured to allow the first and second intramedullary rods to move relative to each other along an axis in being received in the engagement member to secure the rods in a final position with respect to each other. In one embodiment, the engagement member may include a snap plate.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 9A and 9B are, respectively, enlarged bottom and top plan views of a connector end of intramedullary rods for coupling with the hub described with respect to FIGS. 5-8.

FIGS. 9C and 9D are, respectively, enlarged side and end elevations of the connector end depicted in FIGS. 9A and 9B.

FIG. 13A is a side elevation cross section of the free end of the rod with the anchor stowed.

FIGS. 13B and 13C are the same view as FIG. 13A, except of the anchor being progressively deployed.

FIG. 14A is a side elevation cross section of the free end of the rod with the anchors stowed.

FIG. 14B is the same view as FIG. 14A, except the anchors are fully deployed.

FIG. 15A is a side elevation view of a free end of the rod, wherein the rod is configured to expand.

FIG. 15B is a side elevation cross section of the free end of the rod of FIG. 15A, the rod being in a non-expanded state.

FIG. 15C is the same view as FIG. 15B, except the rod is in the expanded state.

FIG. 25 is a plan view of a proximal locking plate.

FIG. 26 is a plan view of a distal locking plate.

FIG. 27 is a side elevation view of an intramedullary rod that may be employed as part of the implant assembly.

FIG. 28 is the same view as FIG. 27, except showing the rod with an anchor deployed.

FIG. 69 is a longitudinal cross section of the sliding lock on the inner shaft 705.

FIGS. 70A and 70B are transverse cross sections of the intramedullary rods, wherein the embodiment depicted therein shows a rotation to lock the rods.

DETAILED DESCRIPTION

A universal assembly 10 of modular, telescopic, micro-adjustable bone implants for intramedullary fixation is disclosed herein that can be delivered minimally invasively and assembled by the surgeon partially, or entirely, at, or within, a fracture to restore the bone, including the shape of articulating surfaces impacted by the fracture. As the implant assembly 10 may be delivered to the fracture and assembled within the fracture via minimally invasive techniques, patient discomfort and soft tissue damage is minimized. As the implant assembly 10 is intramedullary, it is a load-sharing, not a load-shielding device, thereby promoting the remodeling performance of the bone after the fracture heals and leading to better long-term strength of the bone tissue. Also, as the implant assembly 10 is intramedullary, the assembly 10 does not result in irritation to the soft tissue, and revision surgeries are less likely to be needed. Due in part to its modular, telescopic, micro-adjustable characteristics, the implant assembly 10 is highly adaptable to a wide variety of fractures with respect to location, bone and severity. For example, while the method of implanting the implant assembly is given below in the context of a radial fracture, the implant assembly 10 is readily employable for any type of fracture in any type of bone. For example, the implant assembly 10 may be employed for fractures of long bones (e.g., humerus, ulna, radius, femur, tibia, etc.) anywhere along the long bone shaft or near a long bone joint (e.g., shoulder, elbow, wrist, hip, knee, ankle, etc.). The implant assembly 10 may also be employed for other bone fractures (e.g., fingers, toes, ribs, vertebra, pelvis, etc.) in the body of such bones or near any joint of such bones. The modular and minimally invasive characteristics of the implant assembly 10 may reduce by approximately 50% the number of surgical steps needed to repair a fracture as compared to repairing the same fracture with plates or intramedullary rods known in the art, saving surgical time, costs and risks to the patient from lengthened procedure times.

Figure 1:
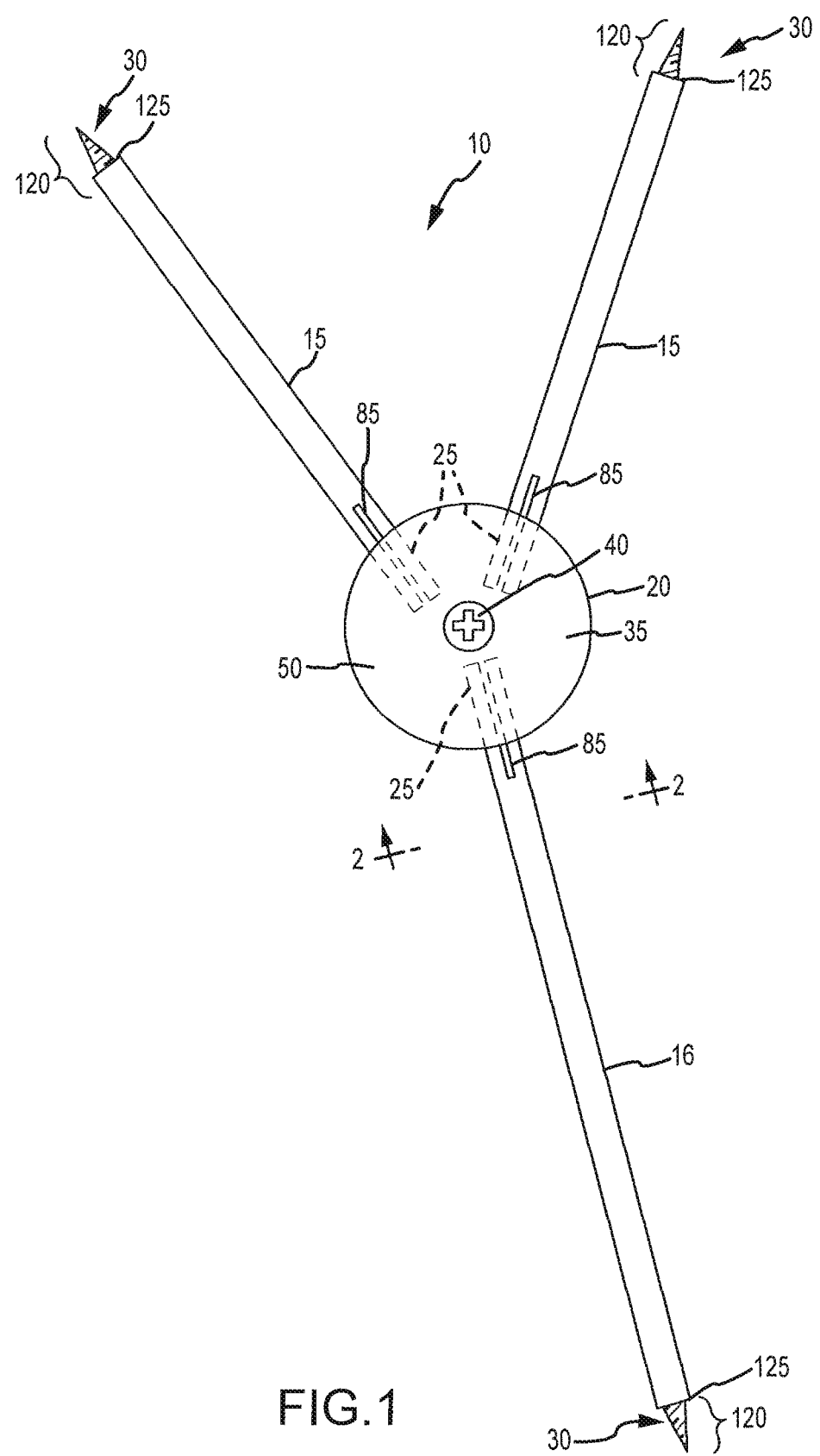
FIG. 1 is a top plan view of a first embodiment of the bone implant assembly in an assembled state.
Figure 2:
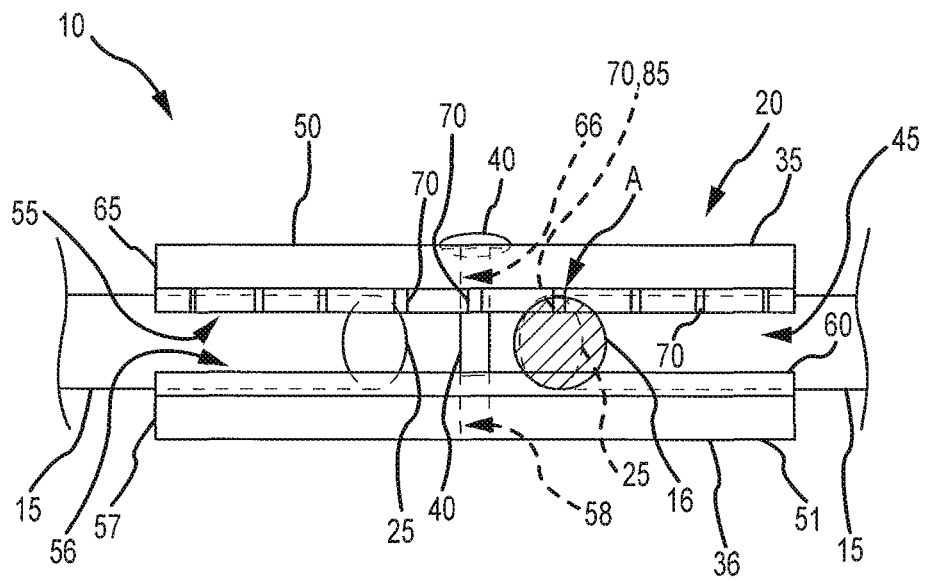
FIG. 2 is a side elevation view of the first embodiment of the bone implant assembly as taken along section line 2-2 in FIG. 1.
Figure 3:
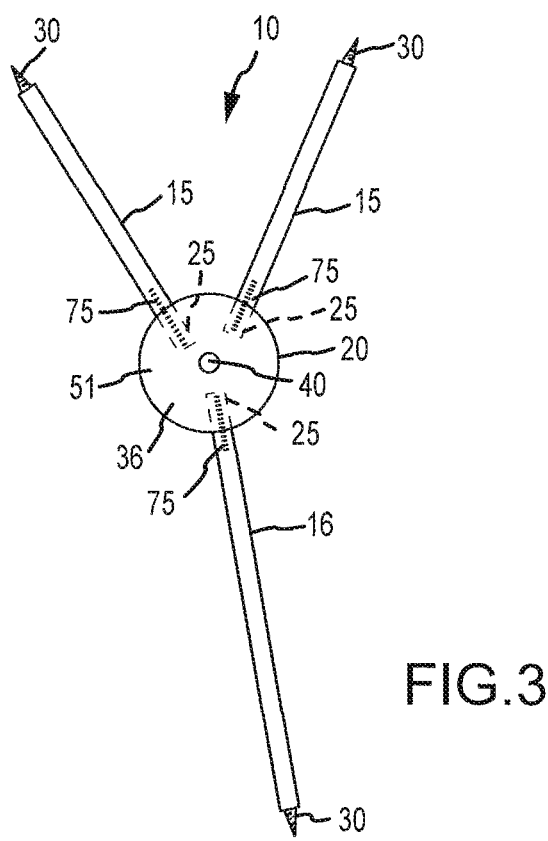
FIG. 3 is a bottom plan view of a first embodiment of the bone implant assembly in an assembled state.

For a detailed discussion of an embodiment of the bone implant assembly 10 disclosed herein, reference is made to FIGS. 1-3. FIGS. 1 and 3 are, respectively, top and bottom plan views of the first embodiment of the bone implant assembly 10 in an assembled state. FIG. 2 is a side elevation view of the first embodiment of the bone implant assembly 10 as taken along section line 2-2 in FIG. 1.

As can be understood from FIGS. 1 and 3, the bone implant assembly 10 in an assembled state includes multiple intramedullary members or rods 15, 16 radiating from a central locking member or hub 20. Depending on the needs of the fracture to be secured via the bone implant assembly 10, there may be at least two, three or more rods 15, 16 radiating from the hub 20. As will be discussed in greater detail below, at least one of the rods 15 will extend from the hub 20 to one side of the fracture (e.g., a distal side of the fracture), and at least another of the rods 16 will extend from the hub 20 to the other side of the fracture (e.g., a proximal side of the fracture). In other embodiments, as discussed below with respect to FIGS. 78 and 79, the bone implant assembly 10 may include one, two, three or more rods 15, 16 extending from the hub 20. For example, in one embodiment, one to five rods 15, 16 may extend from a single hub 20.

Figure 80:
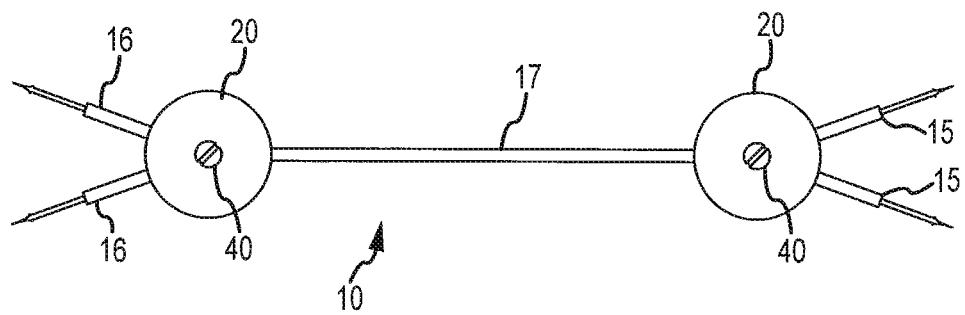
FIG. 80 is a plan view of a multiple hub embodiment of the implant assembly.

As discussed below with respect to FIG. 80, the implant assembly 10 may include two or more hubs 20 joined together by one or more rods 15, 16 and, in some embodiments, further including one, two, three, four or more rods 15, 16 further extending from the hubs 20. For example, in one embodiment, two to nine rods 15, 16 may extend from two hubs 20.

In some embodiments, the rods 15, 16 may have a fixed length and, in other embodiments, the rods 15, 16 may have an adjustable length. In some embodiments, the implant assembly 10 may employ only fixed length rods, only adjustable length rods, or a combination of fixed length and adjustable length rods.

As indicated in FIGS. 1-3, each rod 15, 16 includes a connector end 25 and a free end 30. When the assembly 10 is in an assembled state, the connector ends 25 are received in an engaged or coupled fashion in the hub 20, and the free ends 30 radiate away from the hub 20 such that the free ends 30 may be engaged to bone tissue.

In one embodiment as shown in FIGS. 1-3, the hub 20 includes an upper member or plate 35 and a bottom member or plate 36. While plate 35 and plate 36 are respectively referred to herein as the upper plate and lower plate, the positions of the plates may be reversed relative to each by design or in practice, depending on the embodiment. A securing member 40 (e.g. a screw, bolt, tab, etc.) extends between and through or into the plates 35, 36 to secure the plates 35, 36 to each other in an opposed fashion, defining a void or region 45 between the plates 35, 36 in which the connector ends 25 of the rods 15, 16 are received. In some embodiments, one, two or more securing members 40 may be employed to join together the plates 35, 36 of the hub 20. As each plate 35, 36 includes a respective outer face 50, 51 and respective inner face 55, 56, and the outer faces 50, 51 face away from each other and the inner faces 55, 56 face each other in an opposed fashion when the plates 35, 36 are secured together in an assembled fashion via the screw 40, the opposed inner faces 55, 56 define the void or region 45 in which the connector ends 25 of the intramedullary rods 15, 16 are received.

In one embodiment, the plates 35, 36 of the hub 20 and the connector ends 25 of the rods 15, 16 are configured to create an interlocking or interdigitation of the rods 15, 16 and the plates 35, 36. Described below are various embodiments for achieving this interlocking or interdigitation. For example, in some embodiments, the interdigitation or interlocking may be a notched interlocking of the connector ends 25 to the hub 20, the notched interlocking in some cases even being of a ratcheting arrangement. To begin a discussion of such an embodiment, reference is first made to FIGS. 5-6C, wherein FIG. 5 is a plan view of an inner face 56 of the lower plate 36 and FIGS. 6A-6C are cross sections of different embodiments of the lower plate 36 as taken along section line 6-6 in FIG. 5.

Figure 5:
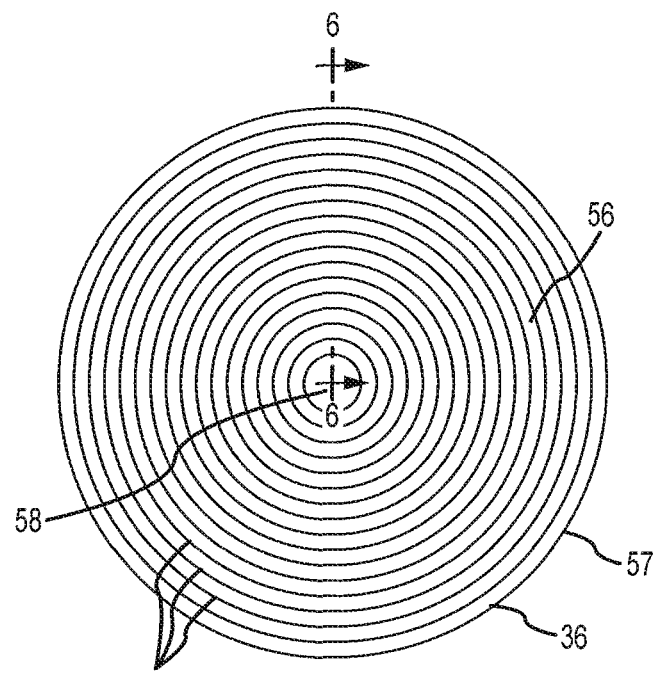
FIG. 5 is a plan view of an inner face of the lower plate.
Figure 6A:
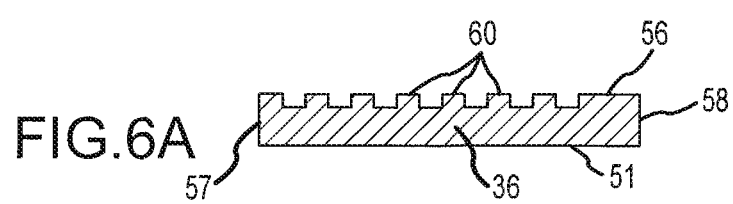
FIGS. 6A-6C are cross sections of different embodiments of the lower plate as taken along section line 6-6 in FIG. 5.
Figure 6B:
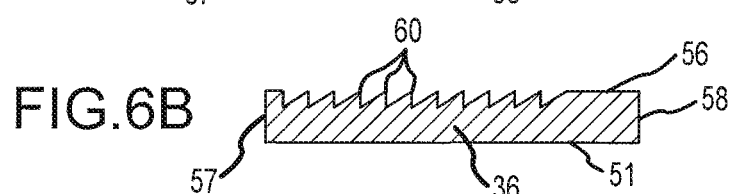

As shown in FIG. 5, the bottom plate 36 includes an outer edge or circumference 57 and a central hole 58 for receiving therein the screw 40. The inner face 56 of the lower plate 36 may have a plurality of concentric rings 60 defined in the inner face 56. As indicated in FIG. 6A, the rings 60 may have a square toothed cross section. Alternatively, as shown in FIG. 6B, the rings 60 may each have a saw toothed cross section, wherein each saw tooth profile is arranged to hold the rods in place and not allow them to move radially outward once fastened to the bottom plate 36. In one embodiment, each saw tooth profile of the rings has a triangular cross section. In one embodiment, the triangular cross section may be a right triangle cross section, the right angle of each ring cross section facing the direction of the central hole 58 and the slope of each ring cross section facing the direction of the outer edge 57. The ring cross section configurations of FIGS. 6A and 6B have features that transfer a pull load directly to the plates without relying on compressive loads from the plates, resulting in a desirable interdigitation or interlocking of the rods to the plates.

Figure 6C:
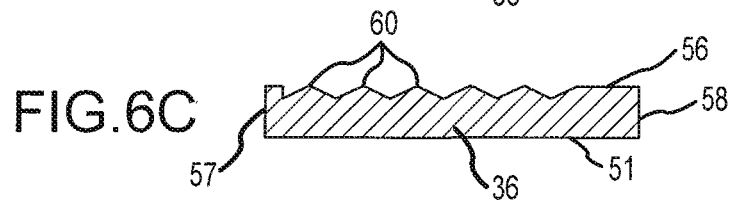

In another alternative, as shown in FIG. 6C, the triangular cross section of the rings 60 may be in the form of an isosceles, equal lateral or other type of triangle cross section, the slope of each triangle cross section facing the direction of the central hole 58 being generally equal to the slope of each triangle cross section facing the direction of the outer edge 57. Such a triangular cross section as depicted in FIG. 6C may be such that the plates 35, 36 be fastened together to produce a compressive force to fix the rods in place within the hub. Thus, such a configuration may rely less on interdigitation or interlocking and more on a friction fit aided by compressive force of the clamping plates.

In one embodiment, the lower plate 36 is machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. The lower plate 36 may have a diameter of between approximately 0.05" and approximately 3", an overall thickness of between approximately 0.02" and approximately 0.5", and the concentric rings 60 may have a height of between approximately 0.01" and 0.1". The lower plate 36 may have between approximately 2" and approximately 100 concentric rings 60. Concentric rings 60 can be evenly spaced, grouped in sections, or unevenly spaced on the plate surface 56. In some embodiments, the upper and lower plates 35, 36 may have generally the same diameters. However, in other embodiments, the upper and lower plates 35, 36 may have different diameters such that the edge of one of the plates may extend past the edge of the other plate.

Figure 7:
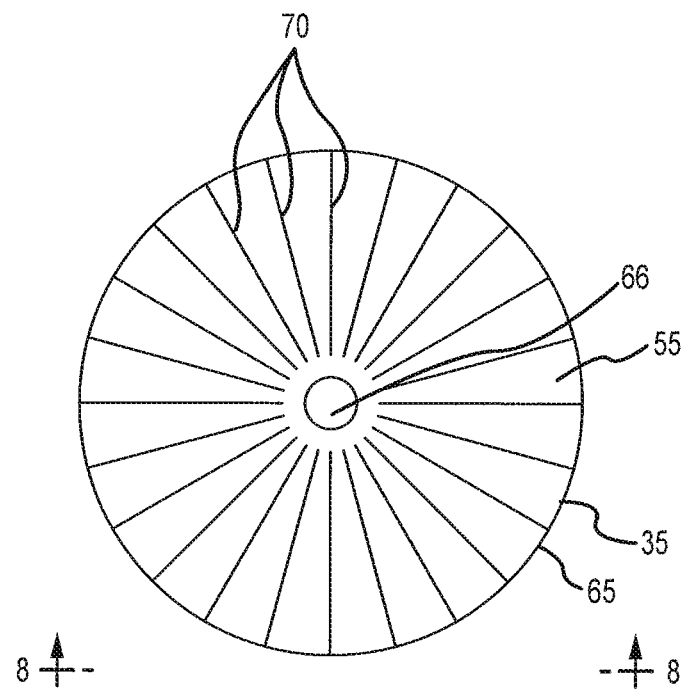
FIG. 7 is a plan view of an inner face of the upper plate.
Figure 8:
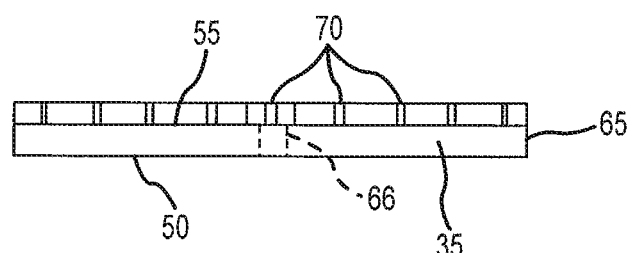
FIG. 8 is a cross section of the upper plate as taken along section line 8-8 in FIG. 7.

As shown in FIGS. 7 and 8, wherein FIG. 7 is a plan view of an inner face 55 of the upper plate 35 and FIG. 8 is a cross section of the upper plate 35 as taken along section line 8-8 in FIG. 7, the upper plate 35 includes an outer edge or circumference 65 and a central hole 66 for receiving therein the screw 40. The inner face 55 of the upper plate 35 may have a plurality of radially oriented ridges 70 defined in the inner face 55. The ridges 70 radiate outwardly from a point near the central hole 66 towards the outer edge 65, and the ridges 70 may have rectangular cross sections.

In one embodiment, the upper plate 35 is machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. The upper plate 35 may have a diameter of between approximately 0.05" and approximately 3", an overall thickness of between approximately 0.02" and approximately 0.5", and the radiating ridges 70 may have a height of between approximately 0.01" and 1". The upper plate 35 may have between approximately 2 and approximately 360 radiating ridges 70. Ridges 70 can be evenly spaced, grouped in sections, or unevenly spaced on the plates surface 55.

For a discussion of the features of a connector end 25 of an intramedullary rod 15, 16 to be received by and connected to the embodiment of the hub 20 discussed above with respect to FIGS. 5-8, reference is made to FIGS. 9A-9D. FIGS. 9A and 9B are, respectively, enlarged bottom and top plan views of a connector end 25 of intramedullary rods 15, 16. FIGS. 9C and 9D are, respectively, enlarged side and end elevations of the connector end 25 depicted in FIGS. 9A and 9B.

As indicated in FIGS. 9A and 9C, the bottom side of the connector end 25 (i.e., the side of the connector end 25 that faces the concentric rings 60 of the bottom plate 36 when the connector end 25 is received in the void 45 of the hub 20) includes a plurality of transverse grooves or teeth 75 defined therein. The grooves or teeth 75 may have a curvature that matches the curvature of the rings 60 of the plate 36. Each of the teeth 75 may have a saw toothed cross section, wherein each tooth 75 has a right triangle cross section, the right angle of each tooth cross section facing the direction of the free end 30 and the slope of each tooth cross section facing in a direction opposite the direction of the free end 30 (i.e., in the direction of the extreme end 80 of the connector end 25). The toothed region formed by the teeth 75 may extend along a length of the rod 15, 16 from a location near the extreme end 80 towards the free end 30 for a distance of between approximately 0.1" and approximately 1.5". While the interdigitation or interlocking features are depicted as being at the connector ends 25 of the various rods 15, 16, in some embodiments, the interdigitation or interlocking features may be in a single region of the rods, in multiple regions of the rods, or the generally the entire surface of the rods. The interdigitation or interlocking features can also be on one or more sides of the rods or extend circumferentially around the entire surface of the rods.

As indicated in FIGS. 9C and 9D, the tooth arrangement may have an elastic or deformable member (e.g. a spring 525) that extends from the rod connector end 25. The spring and teeth, along with the concentric rings of the plate, may combine to form a spring loaded ratchet mechanism.

As shown in FIGS. 9A-9D, the upper side of the connector end 25 (i.e., the side of the connector end 25 that faces the radiating ridges 70 of the top plate 35 when the connector end 25 is received in the void 45 of the hub 20) includes a longitudinally extending slot 85 that extends from the extreme end 80 towards the free end 30 parallel to the longitudinal axis of the rod 15, 16. The length of the slot 85 may be between approximately 0.05" and approximately 1.5".

In one embodiment, the rods 15, 16 are machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. In one embodiment, the rod connector end 25 and/or the concentric rings 60 of the bottom plate 36 are formed of a material that deforms or crimps to facilitate a more secure connection between the rod connector end 25 and the hub 20. Each rod 15, 16 may have a diameter of between approximately 0.01" and approximately 1.5" and an overall length of between approximately 0.1" and approximately 30". Each tooth 75 may have a height of between approximately 0.05" and approximately 0.25". Each rod 15, 16 may have between approximately 2 and approximately 150 teeth 75. Each slot 85 may have a width of between approximately 0.005" and approximately 0.1" and a depth of between approximately 0.005" and approximately 0.1".

As can be understood from FIGS. 5-9D, when the connector ends 25 of the intramedullary rods 15, 16 are received in the void 45 between the plates 35, 36 of the hub 20, as depicted in FIGS. 1-3, the slot 85 of a specific rod 15, 16 may be caused to receive therein a specific radiating guide ridge 70 such that the specific rod 15, 16 may displace along the specific radiating guide ridge 70 towards the center hole 66 of the upper plate 35. As a result, the connector end 25 of the specific rod 15, 16 may be caused to be received within the hub 20 to a greater or lesser extent, depending on how far radially inward the specific slot 85 extends along the specific radiating guide ridge 70. The more fully the specific guide ridge 70 is received in the specific slot 85, the more fully the connector end 25 is received in the hub 20 and the closer the free end 30 of the specific rod 15, 16 is to the outer edge 65 of the upper plate 35. Thus, the distance between the free end 30 and the outer edge 65 can be telescopically adjusted relative to the hub 20 on account of the sliding engagement between the slot 85 and the ridge 70 received therein. Also, as can be understood from FIGS. 1 and 3 and, more specifically from the slot/ridge engagement indicated by arrow A in FIG. 2, the radial orientation of the specific rod 15, 16 about the edge 65 of the upper plate 35 may be selected and maintained according which of the ridge 70 is received by the slot 85. In summary, the engagement between a slot 85 and a specific ridge 70, and the extent of such an engagement, may be used to position the free end 30 of a rod 15, 16 with respect to both the free end's radial position about the hub 20 and the linear distance between the free end and the hub's outer edge.

For example, the concentric rings 60 in the bottom plate 36 allow the connector ends 25 of the intramedullary rods 15, 16 to be positioned at any radial angle relative to the bottom plate 36. The length of the rods is also telescopically adjustable relative to the hub 20 by fixed increments, depending on which rings 60 in the bottom plate are engaged by the ridges, grooves or teeth 75 of the connector ends 25 of the rods 15, 16. The radially oriented guides 70 on the top plate 35 provide lateral stability to the rod connector ends 25 of the rods 15, 16. The two plates are assembled such that the concentric and radial features 60, 70 orient the rods 15, 16 and maintain the orientation.

As can be understood from FIGS. 5-9D, the configuration of the teeth 75 and the spring 525 of a connector end 25 of an intramedullary rod 15, 16 results in a ratchet arrangement with the corresponding concentric rings 60 of the lower plate 36 of the hub 20 when the screw 40 couples the plates 35, 36 together but is not completely screwed tight to make the hub 20 tightly grip the rod connector ends 25 and to make the implant assembly 10 substantially rigid, as described later in this Detailed Description. Specifically, when the plates 35, 36 are generally loosely joined together via a screw 40 that is not tightened down, because of the flexible spring 525 and/or the slopes of the triangular cross sections of the rod teeth 75 face towards the extreme end 80 of the rod 15, 16, and the right angles of the triangular cross sections of the rod teeth 75 face towards the rod free end 30, the ratchet arrangement formed between the rod teeth 75 and the lower plate concentric rings 60 allows the rod connector end 25 to increasingly travel into the void 45 as the ridge 70 is increasingly received in the slot 85. However, the ratchet arrangement prevents the rod connector end 25 from withdrawing from the void 45. Thus, the ratchet arrangement between the rod connector end 25 and the concentric rings 60 allows the rod connector end 25 to be inserted into the void 45 of the hub 20 to the greatest extent made possible via the interaction between the slot 85 and ridge 70 received therein; however, the ratchet arrangement prevents the rod connector end 25 from withdrawing from the void 45, thereby maintaining the rod connector end 25 within the void 45 to the greatest extent the rod connector end 25 has yet to be received in the hub 20. Once the rod connector end 25 is received in the hub 20 to the extent desired, the screw 40 may be fully tightened, causing the hub 20 to rigidly grasp the connector end 25 between the plates 35, 36, preventing any further ratcheting and displacement of the connector end 25 within the hub 20.

Figure 43:
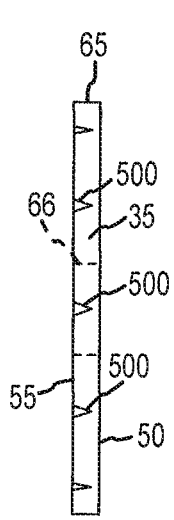
FIG. 43 is a side elevation view of the bottom plate as taken along line 42-42 in FIG. 42.
Figure 42:
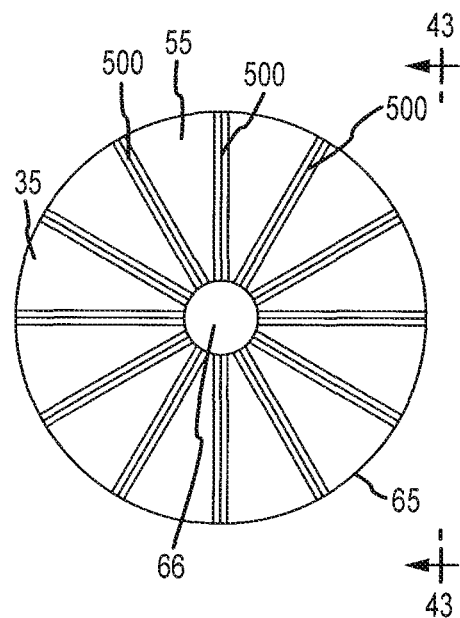
FIG. 42 is a plan view of an interior face of a top plate having radially extending grooves.

In one embodiment, the radially extending ridges 70 of the upper plate 35 discussed with respect to FIGS. 7 and 8 may instead be radially extending grooves 500. For a discussion of such an embodiment, reference is made to FIGS. 42 and 43. FIG. 42 is a plan view of the top plate 35. FIG. 43 is a side elevation view of the bottom plate 35 as taken along line 42-42 in FIG. 42. As shown in FIG. 42, the grooves 500 radially extend from the center hole 66 to the outer circumferential edge 65 and are defined in the inner face 55 of the upper plate 35. As shown in FIG. 43, the grooves 500 may have a V-shaped cross section or other cross section, such as, for example, U-shaped, semi-circular, rectangular, etc.

Figure 44:
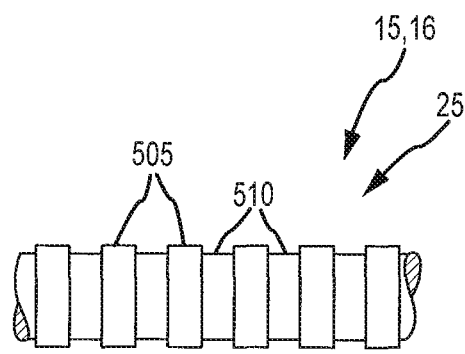
FIG. 44 is a side view of a connector end of a rod, the connector end including a ringed/grooved configuration having plurality of rings and grooves defined in the shaft of the connector end.
Figure 45:
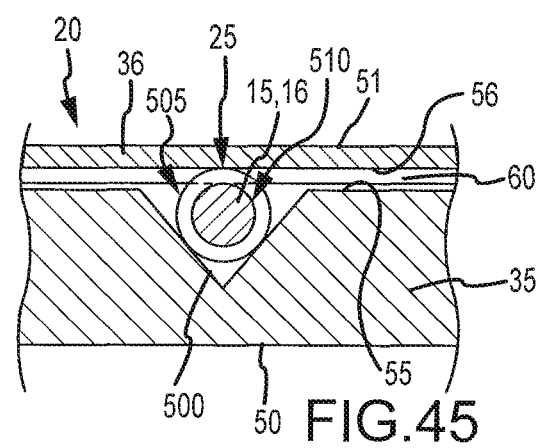
FIG. 45 is a cross section elevation of a connector end extending along a groove of a top plate when the plates are assembled into a hub.

As shown in FIG. 44, which is a side view of a connector end 25 of a rod 15, 16, the connector end may include a ringed/grooved configuration having plurality of rings 505 and grooves 510 defined in the shaft of the connector end 25. As can be understood from FIG. 45, which is a cross section elevation of a connector end 25 extending along a groove 500 of a top plate 35 when the plates 35, 36 are assembled into a hub 20, a concentric ring 60 of the bottom plate 36 is received in a groove 510 of the connector end 25 defined between adjacent rings 505 of the connector end 25. Thus, the groove 500 of the top plate 35 maintains the radial orientation of the connector end 25 and the meshing of the ring/groove arrangement 505, 510 of the connector end 25 with the ring arrangement 60 of the bottom plate 36 secures the connector end 25 in position along the groove 500 of the top plate.

Figure 46:
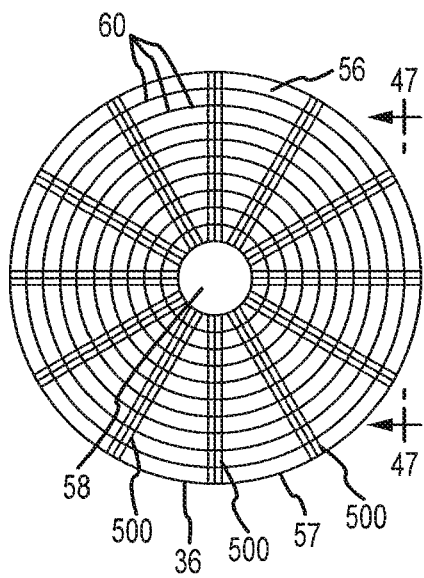
FIG. 46 is a plan view of the interior face of the bottom plate.
Figure 47:
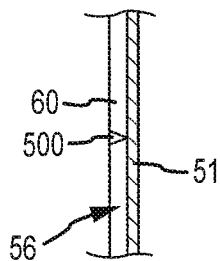
FIG. 47 is a side elevation cross section of the plate as taken along section line 47-47 in FIG. 46.

In one embodiment, the radial grooves 500 and concentric rings 60 can be combined on the interior face of a single plate 35, 36. For a discussion of such and embodiment, reference is made to FIGS. 46 and 47. FIG. 46 is a plan view of the interior face 56 of the bottom plate 36. FIG. 47 is a side elevation cross section of the plate 36 as taken along section line 47-47 in FIG. 46. As shown in FIG. 46, the grooves 500 radially extend from the center hole 66 to the outer circumferential edge 65 and are defined in the inner face 55 of the upper plate 35 and the concentric rings 60 of the inner face 55. As shown in FIG. 47, the grooves 500 may have a V-shaped cross section or other cross section, such as, for example, U-shaped, semi-circular, rectangular, etc. The grooves 500 may be defined only through the concentric rings 60 or additionally through other portions of the bottom plate 36.

Figure 48:
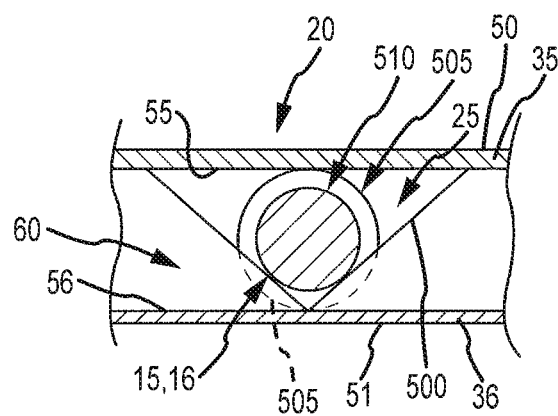
FIG. 48 is a cross section elevation of a connector end extending along a groove of a bottom plate when the plates are assembled into a hub and the bottom plate includes both the radially extending grooves and the concentric rings.

As can be understood from FIG. 48, which is a cross section elevation of a connector end 25 extending along a groove 500 of a bottom plate 36 when the plates 35, 36 are assembled into a hub 20, a concentric ring 60 of the bottom plate 36 is received in a groove 510 of the connector end 25 defined between adjacent rings 505 of the connector end 25. Thus, the groove 500 of the bottom plate 35 maintains the radial orientation of the connector end 25 and the meshing of the ring/groove arrangement 505, 510 of the connector end 25 with the ring arrangement 60 of the bottom plate 36 secures the connector end 25 in position along the groove 500 of the bottom plate 36. In such an embodiment, the top plate 35 inner face 55 may be generally free of any feature, simply acting as a cap to maintain the connector end 25 of the rod 15, 16 received in the radial groove 500 and meshed with the concentric rings 60.

As can be understood from FIGS. 42 and 46, in one embodiment, the radially extending grooves 500 may have generally parallel sides such that the grooves 500 have the same width near the center opening 58 and at the circumferential edge 57. In other embodiments, the radially extending grooves 500 may have sides that diverge from each other such that the grooves are generally pie shaped, having a width at the circumferential edge 57 that is greater than the width at the center opening 58. As a result of the pie shaped configuration of the grooves 500, the grooves 500 may allow a slight radial adjustment of the connector end 25 of the rods 15, 16, allowing the free ends 30 of the rods 15, 16 to be radially positionally varied a small amount despite being secured within the groove 500. In one embodiment, the pie shaped grooves 500 may also be wedge shaped (i.e., the depth of the groove 500 into the plate 35, 36 increases moving from the center hole 58, 66 towards the outer circumferential edge 56, 65. Such a wedge configuration may allow the rods 15, 16 to be attached out of plane from the adjacent locking plate at a pre-determined angle.

Figure 81A:
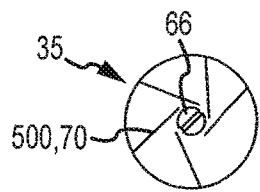
FIGS. 81A-81C are plan views of a plate having an alternative radiating groove or ridge pattern, wherein the radiating pattern and rods, when coupled to the radiating pattern, do not extend from the center of the plate.
Figure 81B:
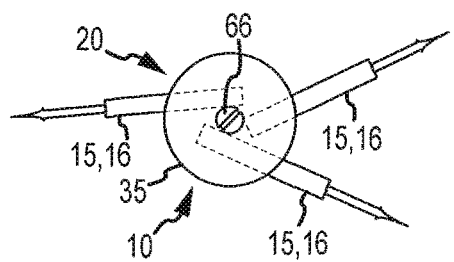
Figure 81C:
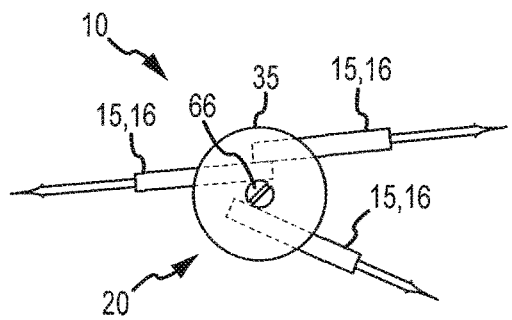

While the embodiments depicted in FIGS. 7, 42 and 46 depict ridges 70 or grooves 500 that extend radially outward from the center hole 66 of the plate or, in other words, the ridges 70 or grooves 500 are in line with the center hole 66 of the plate 35, in other embodiments, the ridges or grooves may have different arrangements. For example, as depicted in FIGS. 81A-81C, which are plan views, respectively, of a plate and plates coupled with rods, a plate 35 may have a radiating pattern of ridges 70 or grooves 500 that radiate outwardly, but are not aligned with the center hole 66 of the plate 35 (see FIG. 81A). Thus, as indicated in FIGS. 81B and 81C, the rods 15, 16 may be coupled to the plate 35 such that they radiate outwardly from the plate, but do not align or extend in the direction of the center hole of the plate. In other words, the line along which the rods extend is offset from the center of the plate.

In one embodiment, the collar 20 may further includes an adjustable collar located between the two plates 35, 36. The collar may be used to set the angle between rods 15, 16 and the plates 35, 36 prior to the plates 35, 36 being tightened together. Once the plates and rods are positioned as desired, the collar acting to temporarily secure the rods as desired, the plates may be tightened together to form the generally rigid hub.

In one embodiment, one or more of the plates 35, 36 may be in the form of a simple plate having multiple slots and/or holes through the surface. These slots and/or holes mate with simple rods 15, 16 having tapped holes that are perpendicular to the longitudinal axis of the rods. Screws or other fasteners are placed through a hole/slot in a plate and into the rod, securing the rod to the plate. In an alternative embodiment, the tapped holes are in the plate and a clean hole in the rod, the screw extending through the rod and into the tapped hole in the plate.

In one embodiment, one or more of the plates 35, 36 are deflectable by being formed of a material that allows the one or more plates to be deformed around the rods 15, 16 when the plates 35, 36 are secured together by, for example, tightening screws to bring the two plates together.

While the plates 35, 36 and hub 20 are depicted as being generally circular in shape, in some embodiments, the plates and hub may have other shapes, such as, for example, rectangular, square, triangular, hexagonal, semi-circular, elliptical, pie slice shaped, etc.

In one embodiment, the plates 35, 36 of the hub 20 and the connector ends 25 of the rods 15, 16 are configured to create a hole or setscrew interlocking of the connector ends 25 to the hub 20, the hole or setscrew interlocking in some cases even being fractionally adjustable in a manner resembling a Vernier scale. To begin a discussion of such an embodiment, reference is first made to FIG. 10, which is a plan view of an inner face 56 of the lower plate 36.

Figure 10:
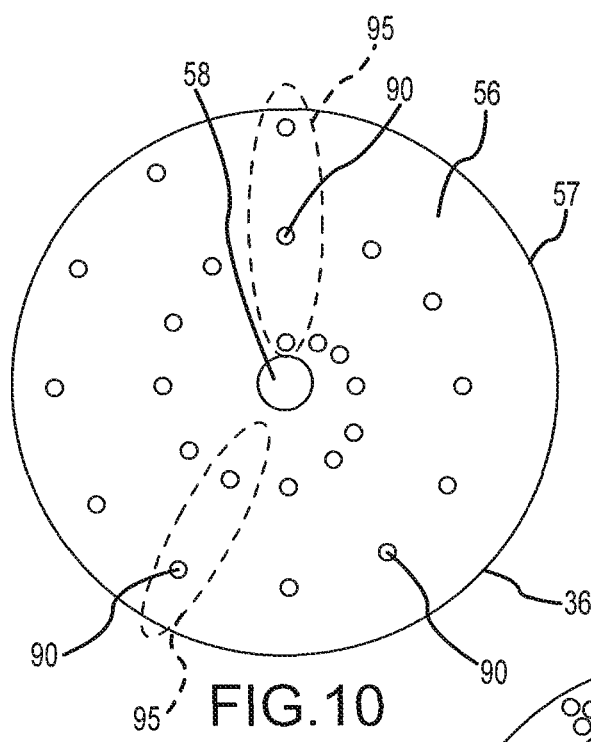
FIG. 10 is a plan view of an inner face of the lower plate of an alternative embodiment of the hub.

As shown in FIG. 10, the bottom plate 36 includes an outer edge or circumference 57 and a central hole 58 for receiving therein the screw 40. The inner face 56 of the lower plate 36 may have a plurality of holes 90 arranged in a spiral array extending between the central hole 58 and the outer edge 57. As indicated in FIG. 10, the holes 90 may be arranged in the spiral array such that at least two holes 90 form each radial line 95 of holes 90 extending from the center hole 58 to the outer edge 57. In one embodiment, each of the radial lines 95 of holes 90 may be radially spaced at approximately five degree increments. In one embodiment, each of the radial lines 95 of holes 90 may be radially spaced at approximately 15 degree increments. In other embodiments, the radial spacing between adjacent radial lines 95 of holes 90 may be greater or lesser than five degrees or greater or lesser than 15 degrees.

In one embodiment, as can be understood from FIG. 10 and from discussion below, the plate 36 may be rotated to determine the set of holes 90 that align with the corresponding notches 110, 111 on the connector end of the intramedullary rod 15, 16 when the rods 15, 16 are implanted with their respective free ends 30 located as desired. Thus, because of the spiral array of holes 90, rotation of the array allows the rods 15, 16 to be telescopically positioned relative to the hub 20 as desired, the rotated array of holes 90 enabling fine adjustment to the distance the rods 15, 16 extend (telescope) away from the hub 20.

In one embodiment, the spiral array equipped plate 36 of FIG. 10 may be employed by itself to form the hub 20 of the implant assembly 10. Specifically, plate 36 may be positioned proximally/distally and rotationally within the bone such that the spiral array of holes 90 may be used to secure the rods 15, 16 to the plate 36 as desired with respect to the extent to which the rods radially extend from the plate and the direction of projection from the plate.

Figure 49:
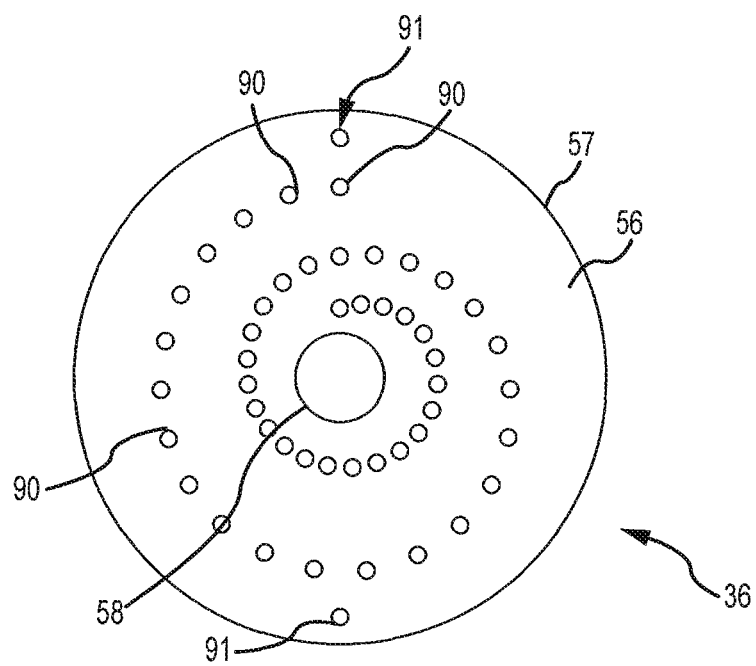
FIG. 49 is a plan view of an inner face of the lower plate of an alternative embodiment of the hub.
Figure 50:
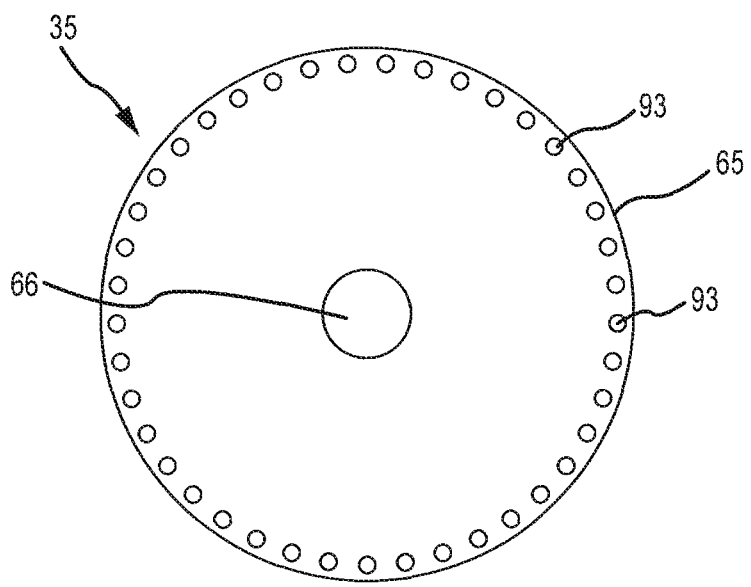
FIG. 50 is a plan view of an inner face of the upper plate of an alternative embodiment of the hub for use with the plate of FIG. 49.

In other embodiments, the spiral array equipped plate 36 may be configured to be used with another plate 35 to form the hub 20 of the implant assembly 10. For example, as indicated in FIG. 49, which is the same view as FIG. 10, except of another embodiment, the spiral array holes 90 discussed with respect to FIG. 10 may further include alignment holes 91 near the outer circumferential edge 57 of the plate 36. In one embodiment, one of the alignment holes 91 is located adjacent the last and most outward hole 90 of the spiral array. Another alignment hole 91 may be located directly across the plate 36 near the opposite side of the outer circumferential edge 57. The alignment holes 91 may be employed for positionally securing the plate 36 rotationally relative to an accompanying plate 35, which may have a plurality of interlocking holes 93 adjacent the outer circumference of the plate 35, as indicated in FIG. 50. In other words, once the plate 36 is rotationally positioned as desired to position the spiral holes 90 as needed, then a pin or setscrew can extend through the alignment holes 91 in the plate 36 and into the locking holes 93 of the plate 35, preventing further rotational displacement between the plates 35, 36, which in combination may form the hub 20 of the implant assembly 10.

In one embodiment, such a lower plate 36 is machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. The lower plate 36 may have a diameter of between approximately 0.05" and approximately 3", an overall thickness of between approximately 0.02" and approximately 0.5", and the holes 90 may have a diameter of between approximately 0.01" and 0.1". The lower plate 36 may have between approximately 1 and approximately 500 holes 90.

Figure 11:
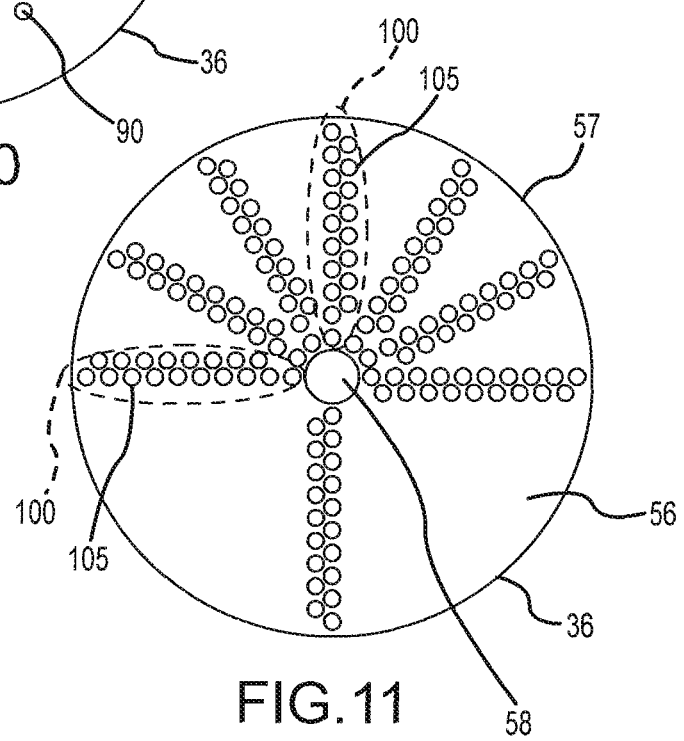
FIG. 11 is a plan view of an inner face of the lower plate of an alternative embodiment of the hub.

As shown in FIG. 11, which is a plan view of an inner face 56 of the lower plate 36, the lower plate 36 includes an outer edge or circumference 57 and a central hole 58 for receiving therein the screw 40. The inner face 56 of the lower plate 36 may have a plurality of radially oriented paired lines 100 of holes 105 in the inner face 56. The paired lines 100 of holes 105 radiate outwardly from a point near the central hole 58 towards the outer edge 57. In one embodiment, the paired lines 100 of holes 105 may be radially spaced from adjacent paired lines 100 of holes 105 at 30 degree increments. In other embodiments, the radial spacing between adjacent paired lines 100 of holes 105 may be greater or lesser than 30 degrees.

In one embodiment, such a lower plate 36 is machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. The upper plate 35 may have a diameter of between approximately 0.05" and approximately 3", an overall thickness of between approximately 0.02" and approximately 0.5", and the holes 105 may have a diameter of between approximately 0.01" and 0.1". The upper plate 35 may have between approximately 1 and approximately 500 holes 105, between approximately 2 and approximately 75 paired lines 100 of holes with between approximately 2 and approximately 50 holes 105 in each line of a paired line 100 of holes 105. The holes 105 extending along a paired line 100 may be spaced or offset from each other at generally even intervals of between approximately 0.02" and approximately 0.1".

In one embodiment, the connector ends of the intramedullary rods 15, 16 may be connected to the paired lines 100 of holes 105 via pins, screws or other members. The extent to which a rod 15, 16 extends from the plate 36 of FIG. 11 will depend where along the paired lines 100 the rod 15, 16 is coupled to the holes 105. Thus, the paired lines 100 of holes 105 may be employed to allow a rod connector end 25 to be coupled to the plate 36 such that the rod 15, 16 extends from the plate 36 a greater or lesser extent. In one embodiment, the plate 36 of FIG. 11 may be rotationally coupled to the plate 35 of FIG. 50 such that the lines 100 of holes 105 may be rotationally positioned about the center holes 58, 66 as desired to allow the rods 15, 16 to extend in a desired direction from the plates of the hub. Once positioned as desired, one or more holes in the plate 36 of FIG. 11 may be pinned, screwed or otherwise connected to the holes 93 adjacent the outer circumference of the plate 35 of FIG. 50, preventing further rotational displacement between the plates of FIGS. 11 and 50.

Figure 52A:
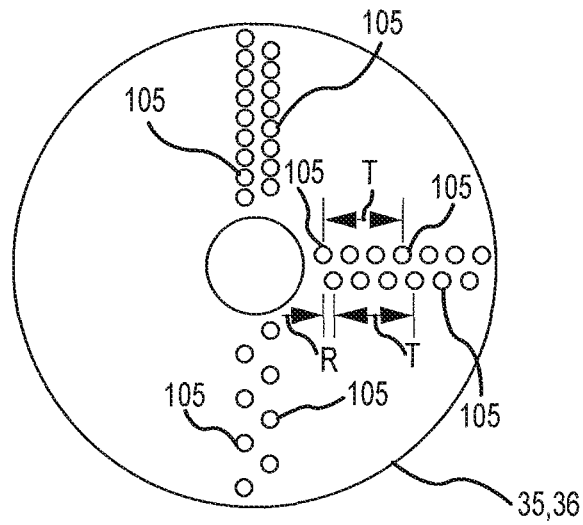
FIG. 52A a view similar to FIG. 11 and depicting the hole spacing.

In other embodiments, the various versions of the plates 35, 36 depicted in FIGS. 10, 11, 49, 50 and 52A may be combined as already discussed above or in other combinations. For example, in some embodiments, the plate of FIG. 10 or 49 may be employed with the plate 35 of FIG. 50. Alternatively, for example, in some embodiments, the plate of FIG. 11 or 52A may be employed with the plate of FIG. 50. Alternatively, for example, in some embodiments where three or more plates are employed, one of the plates may be as depicted in FIGS. 10 and 49 and have rods 15, 16 coupled thereto, another of the plates may be as depicted in FIGS. 11 and 52A and have other rods 15, 16 coupled thereto, and another plate as depicted in FIG. 50 may be used to prevent the three plates from rotating relative to each other once the rods 15, 16 and plates are coupled together and positioned as desired. Alternatively, for example, in some embodiments where three or more plates are employed, two of the plates may be as depicted in FIGS. 10 and 49, each those two spiral array plates having rods 15, 16 coupled thereto, the third plate being as depicted in FIG. 50 and being used to prevent the three plates from rotating relative to each other once the rods 15, 16 and plates are coupled together and positioned as desired. Alternatively, for example, in some embodiments where three or more plates are employed, two of the plates may be as depicted in FIGS. 11 and 52A, each those two pair line array plates having rods 15, 16 coupled thereto, the third plate being as depicted in FIG. 50 and being used to prevent the three plates from rotating relative to each other once the rods 15, 16 and plates are coupled together and positioned as desired.

While the various plates 35, 36 are referred to herein as upper and lower plates, or similar terms, any of the plates 35, 36 described herein may be positioned to be an upper or lower plate or vice versa. Also, any of the different plate embodiments may be combined with any other plate embodiment (e.g., plates described as an upper plate 35 may be combined with another plate described as an upper plate, and plates described as a lower plate 36 may be combined with another plate described as a lower plate) in forming a hub 20. Also, features of the various plates may be combined into a single plate. A hub 20 may be formed of a single plate, two plates, three plates, four plates or more, and each plate of a hub may couple with one or more of the same rods 15, 16 or a specific rod may have a dedicated connection to a single plate of the hub.

Figure 12:
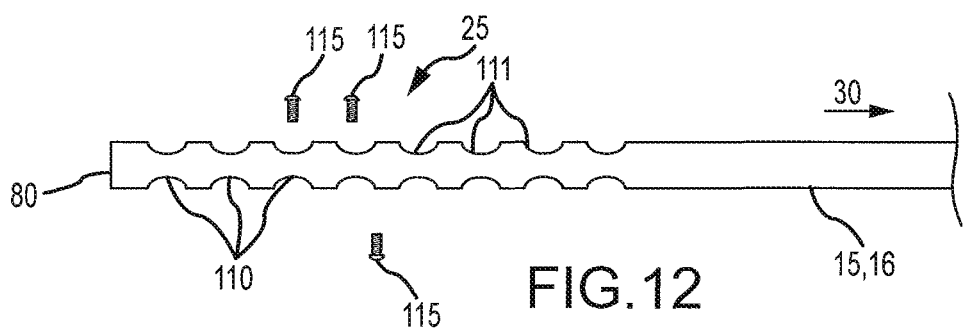
FIG. 12 is an enlarged side elevation of the connector end of intramedullary rods for coupling with the hub described with respect to FIGS. 10 and 11.

For a discussion of the features of a connector end 25 of an intramedullary rod 15, 16 to be received by and connected to the various embodiments of the hub 20 discussed above with respect to FIGS. 10-11, 49, 50 and 52A, reference is made to FIG. 12, which is an enlarged side elevation of the connector end 25 of intramedullary rods 15, 16.

As indicated in FIG. 12, the side of the connector end 25 includes a plurality of notches 110 defined therein. Each of the notches 110 may have a semicircular cross section. The notched region formed by the notches 110 may extend along a length of the rod 15, 16 from a location near the extreme end 80 towards the free end 30 for a distance of between approximately 0.1" and approximately 1.5".

As shown in FIG. 12, the other side of the connector end 25 includes a plurality of notches 111 defined therein. Each of the notches 111 may have a semicircular cross section. The notched region formed by the notches 111 may extend along a length of the rod 15, 16 from a location near the extreme end 80 towards the free end 30 for a distance of between approximately 0.1" and approximately 1.5".

Figure 51A:
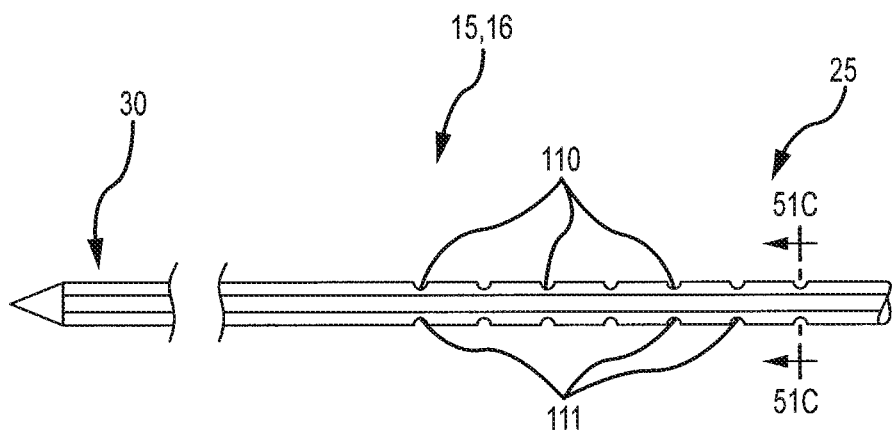
FIG. 51A is a view similar to FIG. 12
Figure 51B:
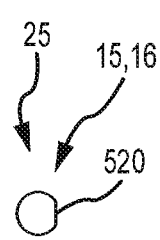
FIG. 51B is an end view of the connector end.
Figure 51C:
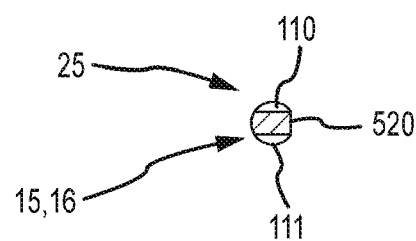
FIG. 51C is a transverse cross section of the connector end as taken along section line 51C-51C in FIG. 51A.

As shown in FIG. 51A, which is a view similar to FIG. 12, the connector end 25 of the rod 15, 16 may include notch spacings on each side that are generally equal and positioned the same as each other. As shown in FIG. 51B, which is an end view of the connector end 25, the connector end 25 may have a flat face 520 that may abut against the interior face 55, 56 of a plate 35, 36. As can be understood from FIG. 510, which is a transverse cross section of the connector end 25 as taken along section line 510-510 in FIG. 51A, the notches 110, 111 are defined in the sides of the connector end 25 that are lateral of the flat face 520.

In one embodiment, the rods 15, 16 are machined, molded, formed or otherwise manufactured from a biocompatible metal, such as, for example, stainless steel, Titanium, Zirconium, Niobium, Cobalt Chrome, or NITINOL® or a biocompatible polymer, such as, for example, PEEK®, TEFLON®, TYROSINE®, POLYSULFONE®, polyethylene, polyurethane, polymethylmethacrylate, DELRIN®, or polyphenylsulfone or a biocompatible ceramic, such as, for example, alumina, zirconia, calcium phosphate, or pyrolitic carbon. Each rod 15, 16 may have a diameter of between approximately 0.01" and approximately 1.5" and an overall length of between approximately 0.1" and approximately 30". Each notch 110, 111 may have a depth of between approximately 0.005" and approximately 0.1" and a length or mating surface area of between approximately 0.01" and approximately 0.25". Each rod 15, 16 may have between approximately 2 and approximately 150 notches 110 on one side and between approximately 2 and approximately 150 notches 111 on the other side. In one embodiment, as indicated in FIG. 12, the notches 110 on the one side may be spaced or offset from each other at generally even intervals of between approximately 0.01" and approximately 0.25". The notches 111 on the other side may be spaced or offset from each other at generally even intervals of between approximately 0.01" and approximately 0.25". Thus, in one embodiment, as indicated in FIG. 12, the notches 110 on one side may have a spacing that is different from the notches 111 on the other side. However, as indicated in FIG. 51A, the spacing of the notches 110, 111 on each side may be generally equal, and the notches 110, 111 on each side may not be offset from each other.

As can be understood from FIGS. 10 and 12 or 49 and 12, when the connector ends 25 of the intramedullary rods 15, 16 are received in the void 45 between the plates 35, 36 of the hub 20 in a manner similar to that depicted in FIGS. 1-3, the spiral array of holes 90 in the bottom plate 36 is employed to allow for a variety of lengths for the intramedullary rods to extend from the hub 20. In other words, the spiral array of holes 90 may be employed to adjust the length of distance between the rod free end 30 and the edge of the hub 20. Once positioned with respect to the extent the rods extend form the plate 36, the plate may be rotated as needed to position the rods as needed with respect to radial direction. The plate 35 of FIG. 50 may then be secured to the spiral plate 36 of FIG. 10 or 49 as described above to prevent the plates 35, 36 from rotationally displacing relative to each other.

As can be understood from FIGS. 10, 12, 49, 50 and 51A, in one embodiment, pins or setscrews 115 may be employed in the holes 90 of the spiral array to engage corresponding notches 110, 111 to secure the rod connector end 25 within the hub 20. The plates 35, 36 may be placed together to sandwich the rod connector ends 25 within the resulting hub 20 as depicted in FIG. 2, and the holes 91, 93 in the plates 35, 36 may be pinned together to prevent the plates from rotationally displacing relative to each other. The central setscrew 40 can then be fully tightened down to cause the hub 20 and rods 15, 16 extending from the hub 20 to form a generally rigid assembly 10.

As can be understood from FIGS. 11 and 52A-52C, the paired line array may be employed to both position the rods 15, 16 with respect to radial position about the hub and telescopic extension from the hub. For example, the paired line array may have radially extending paired lines of holes 105. For each set of paired lines, one line of holes 105 will have a hole spacing that is offset from the hole spacing of the other line of holes 105. As indicated by arrow R in FIG. 52A, the offset R between the lines of holes may be between approximately 0.02" and approximately 0.1". In one embodiment, the offset R may be approximately ½ of the pitch between the holes. As indicated by arrows T and T' respectively in FIGS. 52A and 52C, the spacing T' between adjacent notches 110, 111 on the connector end 25 may be between approximately 0.1" and approximately 0.4", and this spacing T' may correspond to a spacing T between holes 105 in the plate 35, 36 (e.g., spacing T may be the distance across four adjacent holes 105).

In one embodiment, T will be approximately the centerline distance of two holes and the space between them. Hole size may be from approximately 0.02" to approximately 0.08". Such holes may be threaded or not threaded. The pitch between holes on the same side of the rod may be approximately 0.1" to 0.4" with hole size of 0.02" to 0.08". As can be understood from FIG. 52C, groove spacing on one side of the a rod may be in line with the groove spacing on the other side of the rod, and, as can be understood from FIGS. 52A and 52B, the offset spacing of the holes in the plate indexing the rod. Offset spacing R of the holes 105 in the plate labeled may be ½ of the 0.1" to 0.4" pitch range of the grooves in the rod.

Figure 52B:
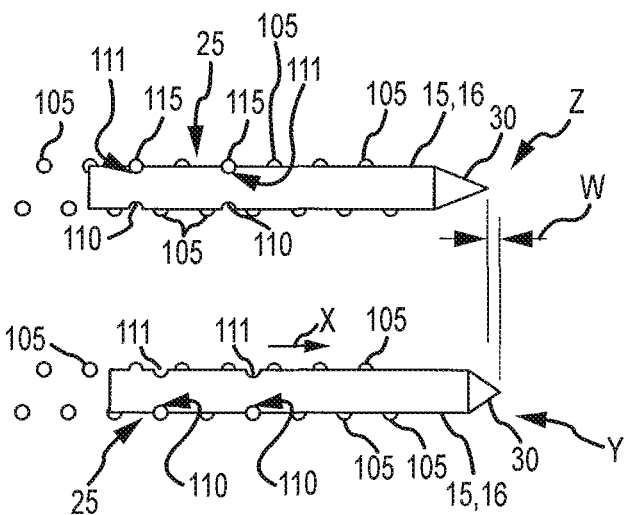
FIG. 52B is a view of the rod connector ends being pinned at different positions along the pair hole array of FIG. 52A.
Figure 52C:
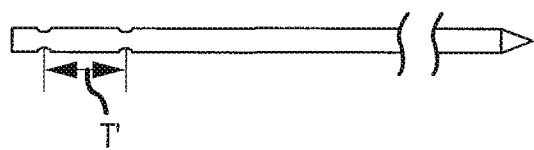
FIG. 52C is a view of a rod connector end having a notch spacing.

As can be understood from FIG. 52B at arrow Z, the rod connector end 25 may be positioned on the plate 35, 36 such that certain notches 111 align with certain holes 105 of a first line of holes 105. Pins or screws 115 may be used to secure the rod connector end 25 in the position indicated by arrow Z. The rod 15, 16 may need to project or telescope further than is allowed by the pin positioning arrangement at arrow Z. As indicated by arrow X, the rod 15, 16 may be moved along the paired line of holes 105 such that the notches 110 on the other side of the rod connector end 25 are mated with holes 105 in the other of the paired lines of holes 105, the free end 30 of the rod 15, 16 projecting further at arrow Y than it did at arrow Z by a movement increment amount of W. Thus, it can be understood that the hole/notch arrangement may be employed to incrementally telescope the rod relative to the hub.

In some embodiments, as can be understood from FIGS. 11 and 52A, in one embodiment, the radially extending paired lines of holes 105 may have parallel lines of holes 105 such that the adjacent lines of holes 105 have the same width of space between the lines of holes 105 near the center opening 58 and at the circumferential edge 57. In other embodiments, the radially extending paired lines of holes 105 may diverge from each other such that the lines of holes 105 define an area between the lines of holes that is generally pie shaped, having a width at the circumferential edge 57 that is greater than the width at the center opening 58. As a result of the pie shaped configuration of the lines of holes 105, the lines of holes 105 may allow a slight radial adjustment of the connector end 25 of the rods 15, 16, allowing the free ends 30 of the rods 15, 16 to be radially positionally varied a small amount despite being secured with the holes 105.

As explained above, in some embodiments, the spiral and paired line arrays depicted respectively in FIGS. 10 and 11 may each be employed respectively on a bottom plate or top plate with the plate of FIG. 50, the plates of FIG. 10 or 11 being employed to position the rods with respect to the hub 20 and the plate of FIG. 50 being employed to complete the hub 20. However, in other embodiments, the hub 20 may only employ the one of the positioning plates depicted in FIG. 10 or 11, and will not be a multi-plate hub 20 (e.g. the hub 20 will not also employ the securing plate of FIG. 50. In some embodiments, the hole arrangements depicted in FIGS. 10 and 11 may be combined or both such plates may be employed in the same hub 20 to act in common to secure and position the same rods 15, 16. In some embodiments, the concentric rings/grooves and/or the radially extending rings/grooves discussed above with respect to FIGS. 5-8 and 42-48, along with the corresponding features of the connector rods 25 configured to work with the concentric and radially extending rings/grooves, may be employed, to a greater or lesser extent, with the notch/hole configurations discussed above with respect to FIGS. 10-12 and 49-52C.

In one embodiment, the plates 35 and 36 respectively depicted in FIGS. 50 and 10 are employed together as a single plate assembly. Specifically, the plate 36 of FIG. 10 is pivotally coupled to the plate 35 of FIG. 50 via a bolt or other fastening member extending through the plates' respective center holes 58. As the plate 36 of FIG. 10 is rotated clockwise, the spiral line of holes 90 will pull the holes 90 on a fixed radial line 95 inwards towards the center of the plate 36. Once the spiral line of holes 90 is rotated to present the combination of holes and location needed to result in the desired notch engagement position for the corresponding rod connector ends 25, the plate 36 of FIG. 10 may be locked rotationally in place relative to the plate 35 if FIG. 50 by extending a fastening member between a hole 90 of the plate 35 into a hole 93 of the plate 36. In some such embodiments, the hub 20 may employ multiple plates 36 of the type depicted in FIG. 10, each such plate 36 being dedicated to positioning a single rod 15, 16.

Figure 53:
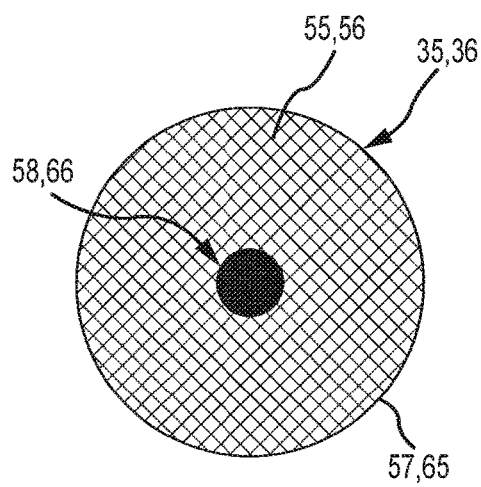
FIG. 53 is a plan view of an interior face of a plate, the interior face being textured.
Figure 54:
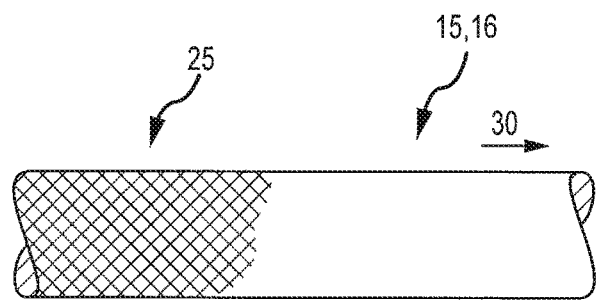
FIG. 54 is a side view of a rod connector end, the connector end being textured.
Figure 55A:
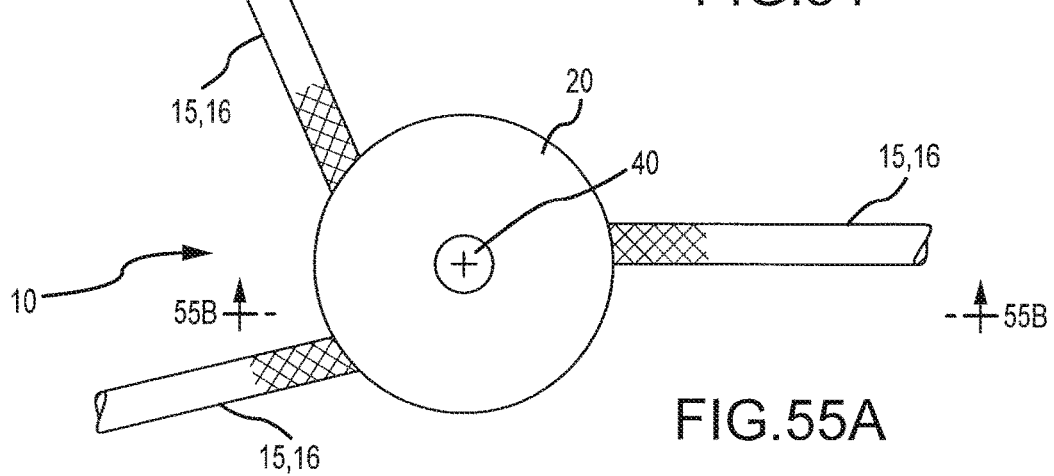
FIG. 55A is a plan view of the implant assembly employing the plates and connector ends of FIGS. 53 and 54.
Figure 55B:
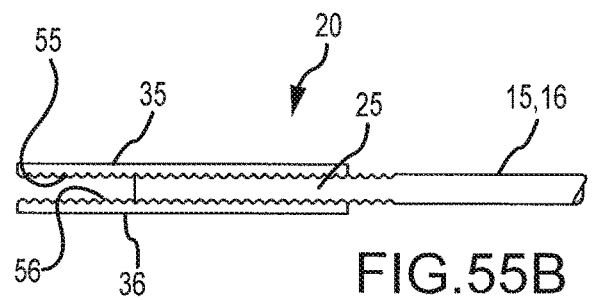
FIG. 55B is a side cross section view of the implant assembly as taken along section line 55B-55B in FIG. 55A.

In some embodiments, the rod connector ends 25 may be configured to provide a textured or friction connection within the hub 20. For example, as shown in FIG. 53, which is a plan view of an interior face 55, 56 of a plate 35, 36, the interior face 55, 56 may be textured (e.g., knurled or otherwise finished) to have a rough, high coefficient of friction surface. As indicated in FIG. 54, which is a side view of a rod connector end 25, the connector end 25 may be similarly textured (e.g., knurled or otherwise finished) to have a rough, high coefficient of friction surface. As indicated in FIG. 55A, which is a plan view of the implant assembly 10, the textured connector ends 25 of the various rods 15, 16 are fixed within the hub 20. As shown in FIG. 55B, which is a side cross section view of the implant assembly 10 as taken along section line 55B-55B in FIG. 55A, the textured interior surfaces 55, 56 engage the textured rod connector end 25 such the rod connector end 25 is securing held in place by the plates 35, 36 being secured together via the screw 40 to form the hub 20 and the overall implant assembly 10. By employing such an embodiment of textured plates and rod connector ends, the positioning options for the rods in the hub with respect to both radial and telescopic position is virtually limitless.

In one embodiment, the plates 35, 36 may be in sections (e.g., a plate may have two semi-circular section, quarter section, etc.). The sections may be individually tightened such that one plate section may be tightened independently from the rest of the plate sections. As a result, one or more rods may be placed and secured in a section of a plate (e.g., the plate section is fully tightened about the one or more rods located within the plate section) after which other rods are placed and secured in other sections of the plate.

In one embodiment, the rod connector ends 25 and the plates 35, 36, or portions thereof, may be configured a ball end connection arrangement. For example, in FIG. 56, which is a side view of a rod connector end 25 having the ball end connection arrangement, the arrangement may include a ball 530 having a hole 535 through which the rod connector end 25 may extend in a telescopic fashion, as indicated by arrow N. The ball 530 may be in the form of two halves 530', 530" or otherwise configured such that the ball 530 can be caused to constrict about the rod connector end 25. The ball 530 may be received in a spherical nest or pot 540 defined via an upper spherical portion 540' in the upper plate 35 and a lower spherical portion 540: in the lower plate 36. On account of the ball end connection, the rod 15, 16 may be both telescopically and radially positioned until the plates 35, 36 are secured together, causing the plates to exert a squeezing force (arrows K in FIG. 57, which is the same view as FIG. 56, except with the squeezing force applied) that causes the spherical nest portions 540', 540" to grip and hold the spherical ball portions 530', 530" in place. Such gripping and holding results in the rod 15, 16 being locked in the desired radial and telescopic position for the free end 30.

Figure 58A:
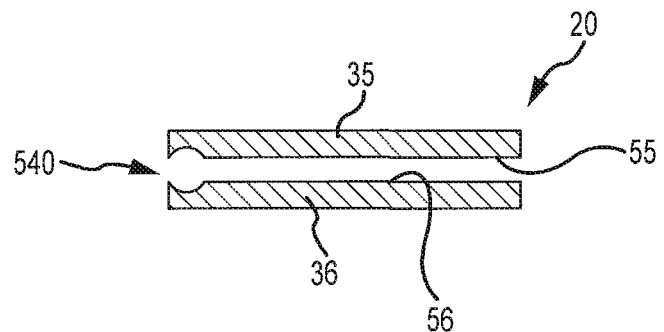
FIGS. 58A-58F depict different views and elements of another version of the ball connection arrangement of FIGS. 56 and 57.
Figure 58B:
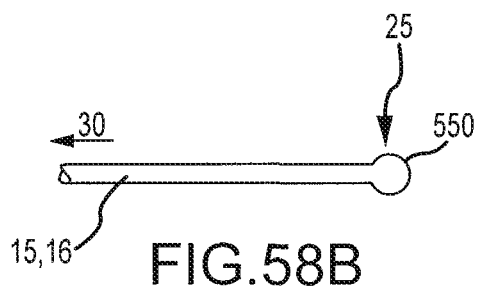
Figure 58C:
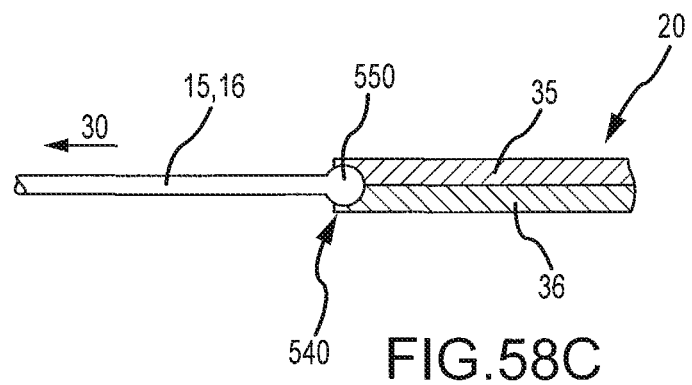
Figure 58D:
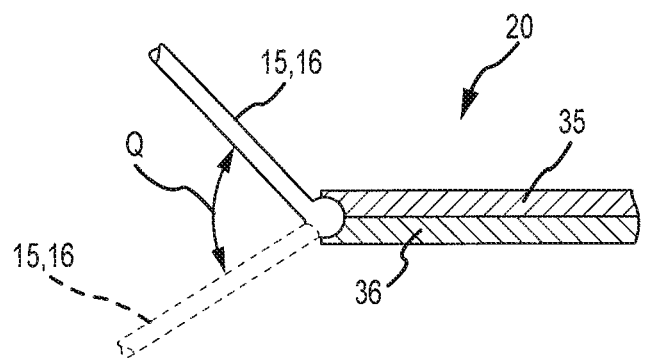
Figure 58E:
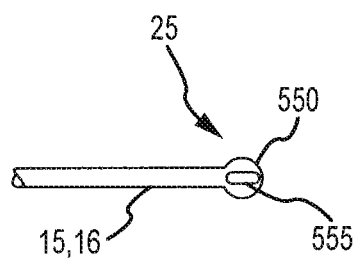
Figure 58F:
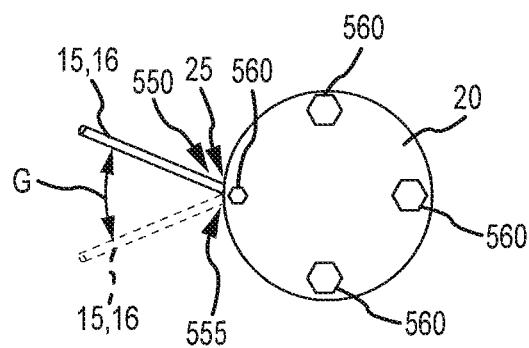

As shown in FIG. 58A, which is a side view of the hub 20, the spherical nest 540 may be formed directly into the interior surfaces 55, 56 of the plates 35, 36. As can be understood from FIGS. 58B and 58C, which are, respectively, a side view of a rod having a connector end 25 with a ball end 550 and a view of the hub and connector end coupled together, the ball end 550 may be secured in the nest 540. As shown in FIG. 58D, which is the same view as FIG. 580, the ball arrangement allows the rod 15, 16 to pivot about the ball 550 and as indicated by arrow Q until the plates are clamped together, as indicated in FIG. 580. As shown in FIG. 58E, which is the same view as FIG. 58B, the ball end 550 may include a hole 555 that may receive a fastener there through. Thus, as shown in FIG. 58F, which is a plan view of the implant assembly 10 employing the ball configuration depicted in FIGS. 58A-58E, the fasteners 560 may extend through the hole 555 to limit the movement to a plane generally parallel to the interior surfaces of the plates, as indicated by arrow G. The fastening of the ball end 550 within the nest 540 may be facilitated by a combination of the plates 35, 36 being tightened together and the fastener 560.

Figure 59A:
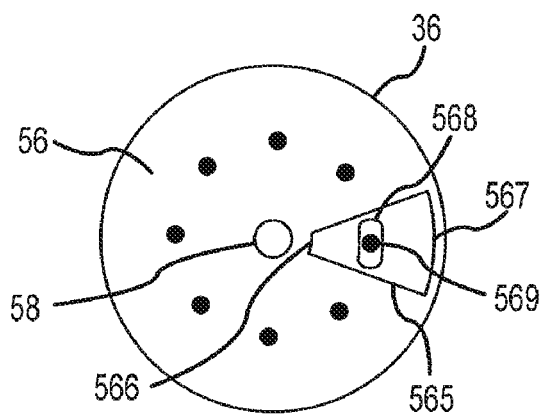
FIG. 59A is a plan view of a bottom plate with a wedged attachment point mounted thereon.
Figure 59B:
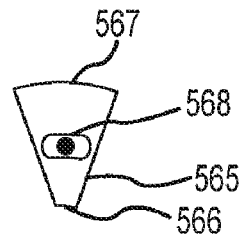
FIG. 59B is a plan view of a wedged attachment point 565.

In one embodiment, as shown in FIGS. 59A and 59B, which are, respectively, plan views of a bottom plate 36 and a wedged attachment point 565, a wedged attachment point 565 may be adjustably mounted on an interior face 56 of the bottom plate 36. As indicated in FIG. 59B, the wedged attachment point 565 may have a narrow end 566, a wide end 567 and an opening 568 between the ends that may be slightly arcuate. As depicted in FIG. 59A, the wedged attachment point 565 may be mounted on the interior face 56 such that the narrow end 566 is near the central opening 58 and the wide end 567 is near the outer circumferential edge 57. A fastener 569 may extend from the interior face 56 through the opening or slot 568.

Figure 59C:
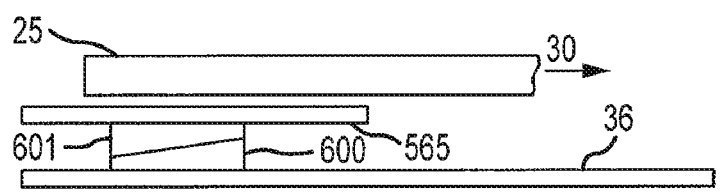
FIG. 59C is a side elevation of the bottom plate and the wedged attachment point of FIG. 59A, wherein the bottom plate and wedged attachment point are parallel.
Figure 59D:
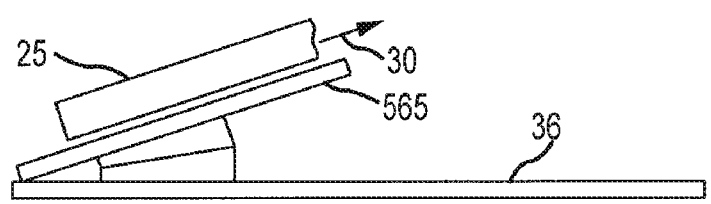
FIG. 59D is the same view as FIG. 59C, except the bottom plate and wedged attachment point are not parallel.

In one embodiment, as indicated in FIGS. 59C and 59D, which are side elevations of the bottom plate 36 and the wedged attachment point 565 mounted thereon, a rod connector end 25 may be coupled to the wedged attachment point 565. The wedged attachment point 565 may be supported off of the bottom plate 36 via interfaced wedged plates 600, 601. Each wedged plate 600, 601 has a wedged thickness. As shown in FIG. 590, when the wedged plates 600, 601 are rotated relative to each other in one way, the wedged thicknesses cancel each other out such that the wedged attachment point 565 is generally parallel to the bottom plate 36. However, as illustrated in FIG. 59D, when the wedged plates 600, 601 are rotated relative to each other in another way, the wedged thicknesses complement each other such that the wedged attachment point 565 is sloped relative to the bottom plate 36. Thus, in the embodiments depicted in FIGS. 59A-59D, it can be understood that the wedged attachment member 565 facilitates the rod 15, 16 being varied radially in a plane parallel to the bottom plate 36, and the wedged plates 600, 601 facilitates the rod 15, 16 being varied radially in a plane perpendicular to the bottom plate 36. Depending on the embodiment, the rods may extend both ways up and down the pie plate 565 shown in FIG. 59D. In other embodiments, the rod will extend down the pie plate 565 in FIG. 59D, not up the pie plate.

Figure 4A:
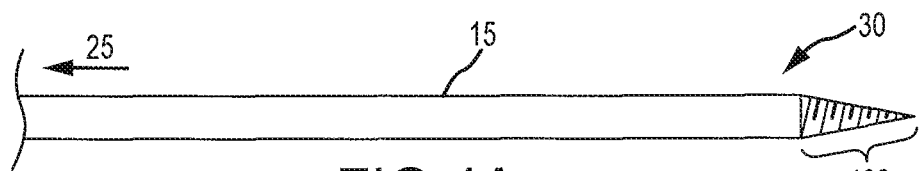
FIGS. 4A-4C are side elevation views of alternative embodiments of free ends of intramedullary rods, wherein the free ends have bone interface tips with different features.
Figure 4B:
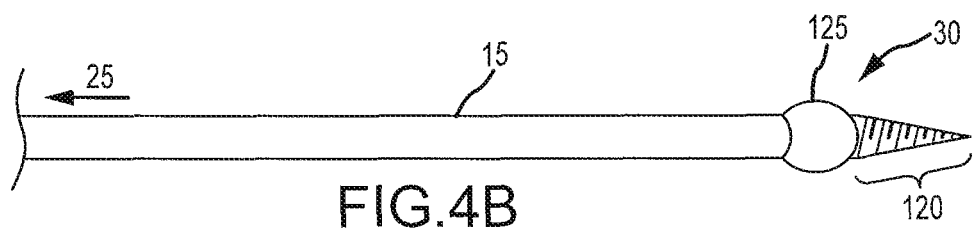
Figure 4C:
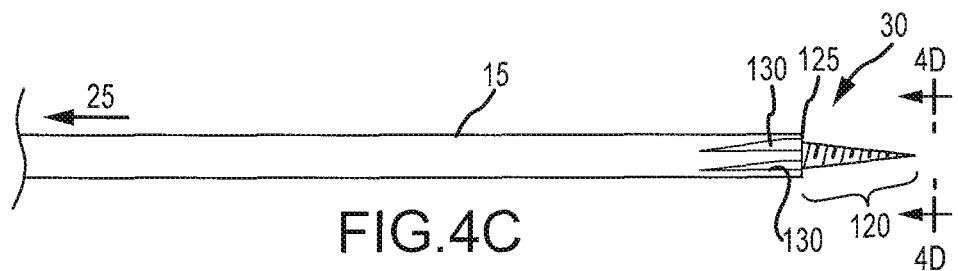
Figure 4D:
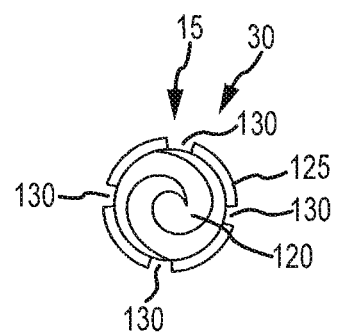
FIG. 4D is an end elevation view of the embodiment depicted in FIG. 4C as viewed along line 4D-4D in FIG. 4C.

In one embodiment, certain intramedullary rods 15 have free ends 30 configured to interface with cortical bone (or other bone materials, which depending on the context, may include cortical bone, cancellous bone, and/or bone marrow) that is between the fracture location and a joint surface. For example, in the context of a distal radial fracture, the free ends 30 of certain intramedullary rods 15 will be configured to interface with cortical bone distal the fracture. In the context of a femoral neck fracture, the free ends 30 of certain intramedullary rods 15 will be configured to interface with cortical bone proximal the fracture. For a discussion of the features of free ends 30 for such intramedullary rods 15, reference is made to FIGS. 4A-4D. FIGS. 4A-4C are side elevation views of alternative embodiments of free ends of intramedullary rods, wherein the free ends have bone interface tips with different features. FIG. 4D is an end elevation view of the embodiment depicted in FIG. 40 as viewed along line 4D-4D in FIG. 4C.

As indicated in FIGS. 4A-4C, each embodiment of the free end 30 of the rod 15 has an interface tip 120 for penetrating or otherwise interfacing in an attaching manner cortical bone. More specifically, each free end of an intramedullary rod 15 has a penetration tip 120 for penetrating cortical bone and, thereby causing the free end 30 to connect to the cortical bone. In one embodiment, the tip 120 is pointed and may be threaded such that the tip 120 may be screwed into the cortical bone. In other embodiments, the tip is not threaded and may be pointed or blunt. In one embodiment, the length of the pointed and threaded tip 120 may be between approximately 0.5 millimeters and approximately 15 millimeters.

In some embodiments, a physical impediment 125 may be found on the free end 30 immediately adjacent to the widest end of the pointed and threaded tip 120. For example, as shown in FIG. 4B, the physical impediment 125 may be in the form of a spherical backstop 125 having a diameter that exceeds the diameter of the intramedullary rod 15 by approximately 5 percent to approximately 75 percent. In another embodiment, as shown in FIGS. 4C and 4D, the physical impediment 125 may be in the form of a collar, rim, lip or other step-like transition 125 in the diameter of the intramedullary rod 15 at the transition between the widest end of the pointed and threaded tip 120 and the rest of the rod 15. Regardless of the shape of the physical impediment 125, the physical impediment 125 improves the surgeons' ability to feel that the tips 120 are sufficiently penetrated into the cortical bone while helping to prevent the surgeon from causing the tips 120 to over penetrate. In other words, the physical impediment 125 may prevent the tip 120 from penetrating into the cortical bone more than the length of the threaded tip 120, thereby preventing articular protrusion of the tip 120.

As illustrated in FIGS. 4C and 4D, in one embodiment, the rod 15 also include grooves 130 that extend into the rod 15 and extend towards the connector end 25 from the widest end of the pointed and threaded tip 120. These grooves 130 may be cut into the rod beginning at the edge of the collar 125 to facilitate the movement of material away from the tip 120. These grooves 130 will also help to distribute bone chips surrounding the rod 15 and improve the fixation of the rod 15 to the surrounding cortical bone.

In some embodiments, the rod free end 30 may not have an interface tip 120, but instead have a blunt end that is not configured to penetrate bone material.

In some embodiments, the intramedullary rod 15 may further include an anchor 135 to prevent the tip 120 from being pulled out of the cortical bone once tip 120 is fixed into the cortical bone. For a discussion of such an anchor 135, reference is made to FIGS. 13A-13C, wherein FIG. 13A is a side elevation cross section of the free end 30 of the rod 15 with the anchor 135 stowed and FIGS. 13B and 13C are the same view, except of the anchor being progressively deployed. As can be understood from FIG. 13A, the anchor 135 is stored inside the intramedullary rod 15 until the tip 120 is imbedded in the bone (e.g., the tip 120 has fully penetrated cortical bone 133). In one embodiment, the rod 15 includes a lumen 140 that extends through the length of the rod 15. The anchor 135 extends through the lumen 140 and may be in the form of a wire or strip 135 that is biased to assume a curved shape, the bias being such that the anchor 135 may be considered to be spring loaded within the lumen 140 until deployed. When the anchor 135 is stowed as depicted in FIG. 13A, the anchor tip 145 is biased against or towards the inner circumferential surface 150 of a lumen 140 and away from an exit opening 155 leading form the lumen 140 to outside the rod 15.

An end 160 of the anchor 135 opposite the anchor tip 145 may be coupled to an anchor actuator 165 that allows the surgeon to manipulate and deploy the anchor 135. For example, in one embodiment, the anchor actuator 165 may be a member or cylinder 165 mounted in the rod 15 that may be both rotated about the rod 15 and axially displaced along the rod 15. Thus, as can be understood from FIG. 13B, by rotating the member 165 about the rod 15 as indicated by arrow B, the anchor 135 is caused to rotate (e.g., 180 degrees) within the lumen 140 such that the anchor tip 145 ends up being located near the exit opening 155. As can be understood from FIG. 13O, by displacing the member 165 axially along the rod 15 as indicated by arrow C, the anchor 135 is caused to axially displace within the lumen 140 such that the anchor tip 145 ends up extending through the exit opening 155 and into a region in the bone 133 near the tip 120. For example, the region in the bone 133 may be cancellous bone and the tip 120 may penetrate cortical bone 133. The anchor tip's passage through the exit hole 155 may be facilitated via the curvature of the anchor 135 and a guide 170 near the exit opening 155.

The anchor actuator 165 may be located at or form the extreme end 80 of the connector end 25 of the rod 15. Alternatively, the anchor actuator 165 may be located on the rod 15 anywhere between the connector end 25 and the free end 30. In other embodiments, the anchor actuator may simply be the end 160 of the anchor 135, the end 160 protruding from an opening in the extreme end 80 and being capable of being grasped and manipulated to bring about the deployment of the anchor tip as shown in FIGS. 13A-13C. The anchor or its actuator may be configured such that either or both lock in place once the anchor is fully deployed. For example, a locking mechanism 175 in the form of a notch 175 on the anchor 135 may ratchet past the guide or backstop 170 such that the anchor 135 cannot be retracted once fully deployed. In some embodiments, there may be more than one notch on the anchor to allow multiple anchoring positions.

In one embodiment wherein the rod 15 has an exterior shaft and interior shaft telescopically arranged relative to each other, the anchor 135 may be deployed by moving the anchor 135 forward relative to the exterior shaft such that the anchor 135 protrudes out through the opening 155 in the rod 15. This motion can be achieved by pushing the interior shaft forward, by pulling the outer shaft back or some combination of these two motions. The opening 155 in the distal end of the rod 15 may be pre-shaped to facilitate the deployment of the anchor 135. There may be one, two or more such anchors 135 for a single rod 15, providing, respectively, one, two or more anchor points.

Figure 74A:
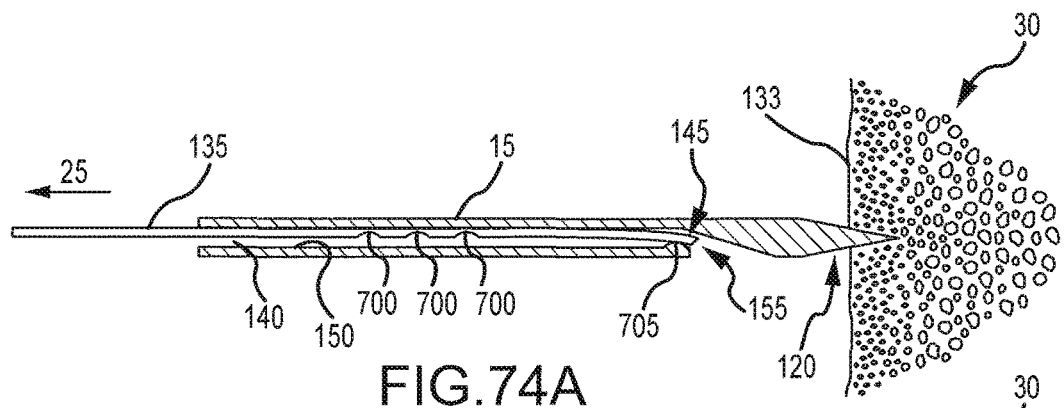
FIGS. 74A and 74B are views respectively similar to FIGS. 13A and 13C, except of another embodiment.
Figure 74B:
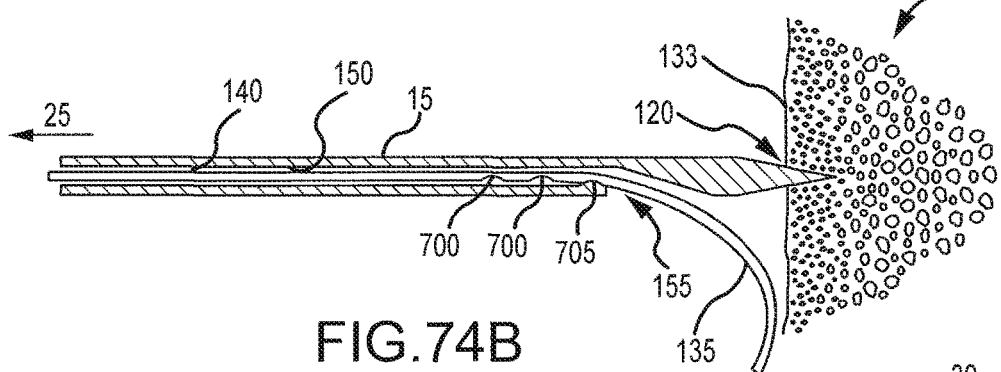

As can be understood from FIGS. 74A and 74B, which are views respectively similar to FIGS. 13A and 13C, the anchor 135 may be locked in place via a locking mechanism once the anchor 13 is fully extended, as shown in FIG. 74B. The locking mechanism may include a notch 700 on the anchor wire 135 that ratchets past a locking bump or pin 705 defined in the inner circumferential surface 150 of a lumen 140 near an exit opening 155 leading form the lumen 140 to outside the rod 15. There may be more than one notch 700 on the anchor wire 135 to allow multiple anchoring positions. In some embodiments, the locking bump or pin 705 may be formed in the inner circumferential surface 150 by crimping, dimpling or otherwise inwardly deforming the wall of the rod 15 to form the feature 705.

As can be understood from FIGS. 13A-14B, 74A and 74B, the rods 15, 16 may employ one, two, three, four or more anchors 135.

Other methods of locking the anchor 135 may be used, for example, by crushing the outer tube of the intramedullary rod 15 into the grooves 700 in the inner anchor wire 135 with a locking pin or clamp, or by crimping the rod 15 to create a press-fit between the shaft of the intramedullary rod 15 and the interior anchor wire 135. In these methods the crimp/crush location on the intramedullary rod 15 may be outside connector end 25 of the intramedullary rod 15 to be incorporated into the central lock hub 20.

The anchor 135 may be made from Nitinol or another spring tempered material that enables the anchor 135 to follow a pre-determined curvature once deployed.

In one embodiment, certain intramedullary rods 16 have free ends 30 configured to interface with bone that is between the fracture location and a shaft of the bone or a portion of the bone that is opposite the fracture from a joint surface. For example, in the context of a distal radial fracture, the free ends 30 of certain intramedullary rods 16 will be configured to interface with bone proximal the fracture. In the context of a femoral neck fracture, the free ends 30 of certain intramedullary rods 16 will be configured to interface with bone distal the fracture. For a discussion of the features of free ends 30 for such intramedullary rods 16, reference is made to FIGS. 14A-14B. FIG. 14A is a side elevation cross section of the free end 30 of the rod 16 with the anchors 135 stowed. FIG. 14B is the same view, except the anchors 135 are fully deployed.

As can be understood from FIGS. 14A-14B, each embodiment of the free end 30 of the rod 16 has an interface tip 120 for penetrating or otherwise interfacing in an attaching manner bone. More specifically, each free end of an intramedullary rod 15 has a penetration tip 120 for penetrating bone and, thereby causing the free end 30 to connect to the bone. In one embodiment, the tip 120 is pointed and may be threaded such that the tip 120 may be screwed into the bone. In one embodiment, the length of the pointed and threaded tip 120 may be between approximately 0.5 millimeters and approximately 15 millimeters.

In some embodiments, the tip 120 may include any of the physical impediments 125 and/or the grooves 130 discussed above with respect to FIGS. 4A-4C.

As shown in FIGS. 14A and 14B, the rod 16 may be equipped with multiple anchors 135 similar to the anchor 135 discussed above with respect to FIGS. 13A-13C and FIGS. 74A-74B. Specifically, the anchors 135 may be axially displaced within the rod lumen 140 to exit from respective exit openings 155. Each anchor 135 may be equipped with a locking mechanism 175 similar to that described with respect to FIGS. 13A-13C and FIGS. 74A-74B. Full deployment of the anchors 135 allows the rod tip 120 to be anchored in the bone material or, more specifically, in the shaft of the bone. Thus, the multiple anchors 135 (e.g., three, four or more anchors) enables the free end 30 of the rod 16 to contact the interior of the shaft of a long bone, such as, for example, a radius, femur or tibia in at least two or three positions to increase the torsional and rotational stability of the fracture. The multiple anchors 135 depicted in FIGS. 14A and 14B may be deployed via any of the mechanisms discussed with respect to FIGS. 13A-13C and FIGS. 74A-74B.

In other embodiments of the rod 16, the outer wall of the rod 16 near the tip 120 may be caused to expand to cause the tip 120 to secure itself within the bone shaft. For example, as depicted in FIG. 15A, which is a side elevation view of a free end 30 of the rod 16, the rod outer wall or surface 180 may be sectioned immediately adjacent the rod tip 120 via cuts or scores 185. As shown in FIG. 15B, which is a side elevation cross section of the free end 120 of the rod 16, a shaft 190 extends through the axial center of the rod 16, one end 195 of the shaft 190 being connected to the tip 120 and the other end 200 being configured such that it may be acted upon by the surgeon.

As shown in FIG. 15C, the shaft 190 may be displaced away from the tip 120 within the rod 16 as indicated by arrow D such that the tip 120 acts against the sectioned wall 180 so as to cause the wall 180 to fold (e.g., like a paper lantern). Thus, displacing the shaft 190 within the rod 16 as indicated by arrow D will cause the wall to form a substantially radially expanded portion 205, which can be used to secure the tip 120 within the bone shaft once the tip 120 is properly positioned within the bone shaft. Depending on the embodiment, the surgeon may cause the displacement between shaft 190 and rod 16 by pulling the shaft 190 back relative to the rod 16 or causing rod 16 to move forward relative to the shaft 190. The shaft 190 may have a notch 175 that engages a feature 170 on the rod 16 that locks the rod and shaft in place once the radially expanded portion 205 makes contact with the cortical bone within the bone shaft. This contact will limit displacements of the free end 30 of the rod 16. The locking of the rod and shaft relative to each other via features 170, 172 will prevent the radially expanded portion 205 from unfolding. The locking of the rod and shaft relative to each other may be accomplished via other configurations, for example, by pins, screws or other members extending between the rod and shaft. Alternatively, the rod may be crimped about the shaft to secure the rod and shaft relative to each other.

Figure 16A:
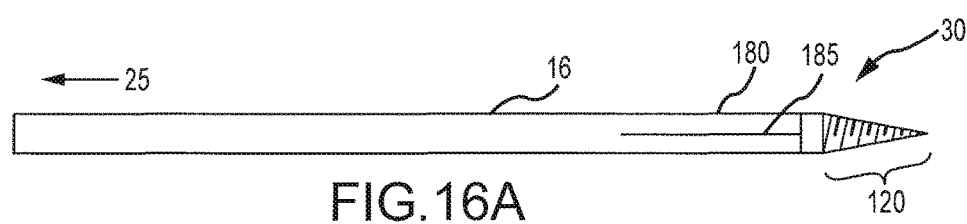
FIG. 16A is a side elevation view of another free end of the rod, wherein the rod is also configured to expand.
Figure 16B:
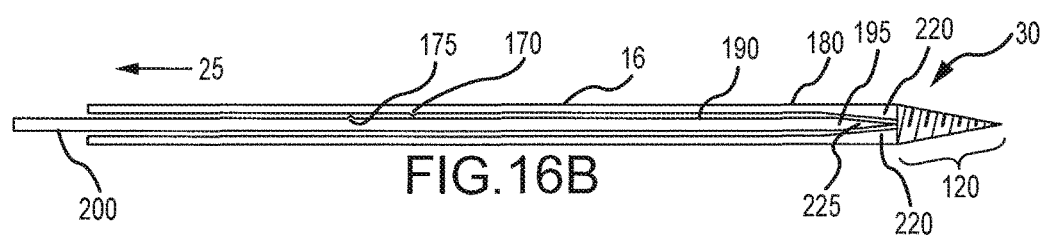
FIG. 16B is a side elevation cross section of the free end of the rod of FIG. 16A, the rod being in a non-expanded state.

In another embodiment of the rod 16, the outer wall of the rod 16 near the tip 120 may also be caused to expand to cause the tip 120 to secure itself within the bone shaft. For example, as depicted in FIG. 16A, which is a side elevation view of a free end 30 of the rod 16, the rod outer wall or surface 180 may be sectioned immediately adjacent the rod tip 120 via cuts or scores 185. As illustrated in FIG. 16B, which is a side elevation cross section of the free end 120 of the rod 16, the rod outer wall 180 may have a thickened portion 220 immediately adjacent the rod tip 120. In other words, the interior of the rod 16 may constrict in diameter moving towards the free end 30 such that the wedge shape 225 may interact with the interior constricted surfaces of the rod 16. As shown in FIG. 16B, a shaft 190 may be extended through the axial center of the rod 16, one end 195 of the shaft 190 having a wedge shape 225 and the other end 200 being configured such that it may be acted upon by the surgeon. The free tip 120 may be connected to the rest of the rod 15 via narrow longitudinally extending wall strips extending through the region of the cuts 185. These narrow longitudinally extending strips may have a constant wall thickness similar to the wall thickness used throughout the rest of the rod 15, with the exception of the thickened wall portions 220.

Figure 16C:
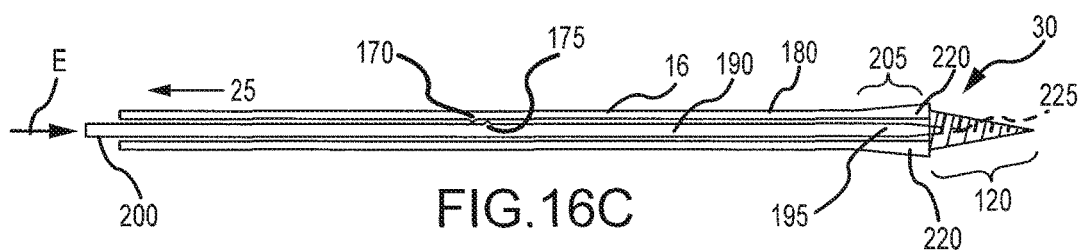
FIG. 16C is the same view as FIG. 16B, except the rod is in the expanded state.

As shown in FIG. 16C, the shaft 190 may be displaced towards the tip 120 within the rod 16 as indicated by arrow E such that the wedge tip 225 acts against the thickened wall portion 220 so as to cause the thickened wall portion 220 to bulge outward near the interface between the wall 180 and the tip 120. Thus, displacing the shaft 190 within the rod 16 as indicated by arrow E will cause the wall to form a substantially radially expanded portion 205, which can be used to secure the tip 120 within the bone shaft once the tip 120 is properly positioned within the bone shaft. The wedge tip 225 may be received within the rod tip 120 as indicated in FIG. 16O. Depending on the embodiment, the surgeon may cause the displacement between shaft 190 and rod 16 by pushing the shaft 190 forward relative to the rod 16 or causing rod 16 to move backward relative to the shaft 190. The shaft 190 may have a notch 175 that engages a feature 170 on the rod 16 that locks the rod and shaft in place once the radially expanded portion 205 makes contact with the cortical bone within the bone shaft. This contact will limit displacements of the free end 30 of the rod 16. The locking of the rod and shaft relative to each other via features 170, 172 will prevent the radially expanded portion 205 from returning to a non-bulged state.

Figure 75A:
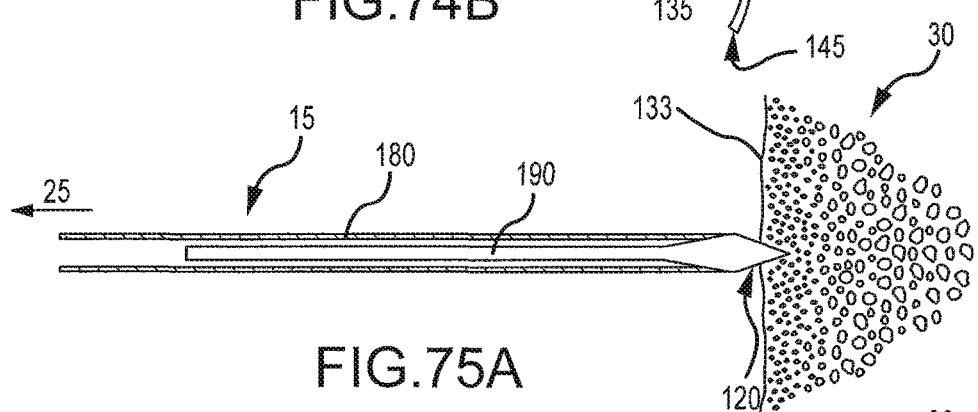
FIGS. 75A and 75B are similar respective views to FIGS. 74A and 74B, except of another embodiment.
Figure 75B:
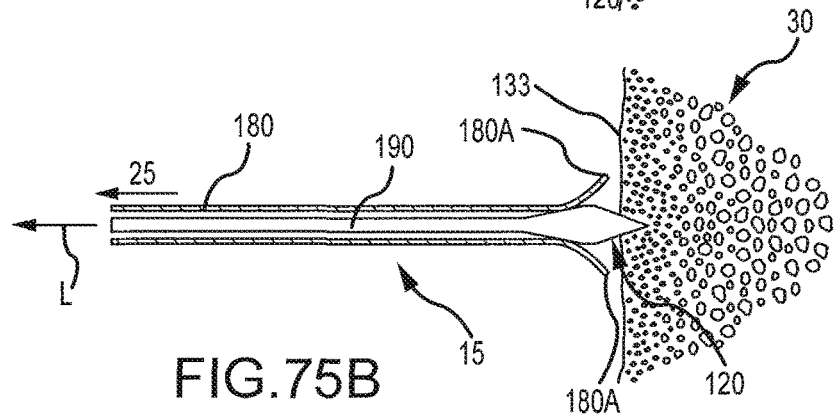

As can be understood from FIGS. 75A and 75B, which are similar respective views to FIGS. 74A and 74B, in one embodiment, the inner shaft 190 may form the tip 120 of the free end 30 of the overall rod 15, and the tip 120 may have a screw, round, tapered, flat or other type of shape. The tip 120 of the inner shaft 190 may project out of the outer shaft 180 at the free end 30, the diameter of the outer shaft 180 at the free end 30 being smaller than a diameter of the tip 120 at the free end 30. The portion of the tip 120 adjacent the interface between the tip 120 and the outer shaft 180 at the free end 30 may be tapered, round, tapered or other shapes.

As can be understood from FIG. 75B, by displacing the inner shaft 190 relative to the outer shaft 180 in the direction of the connector end 25, as indicated by arrow L, the oversized diameter of the tip 120 of the inner shaft 190 causes the outer shaft 180 at the free end 30 to expand radially outward, fixing the free end 30 inside the a region in the bone 133. For example, the expansion may be into the cancellous bone, the tip 120 penetrating into the cortical bone 133. To facilitate the expansion of the outer shaft 180 to create the radially expanded shaft anchoring members 180A, the outer shaft may have reliefs cut therein.

Figure 76A:
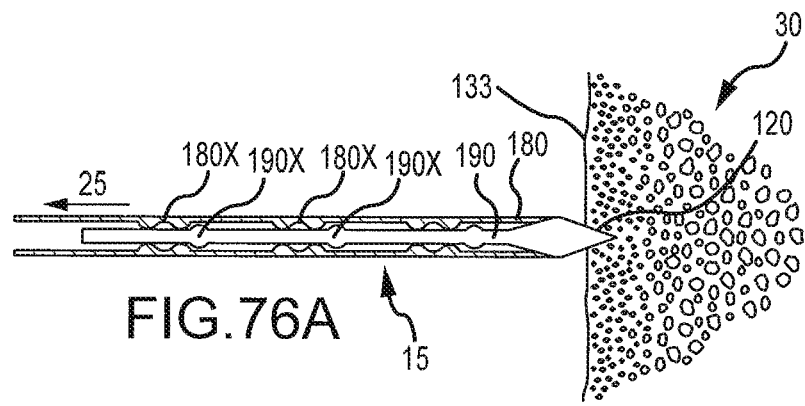
FIGS. 76A and 76B are similar respective views to FIGS. 75A and 75B, except of another embodiment.
Figure 76B:
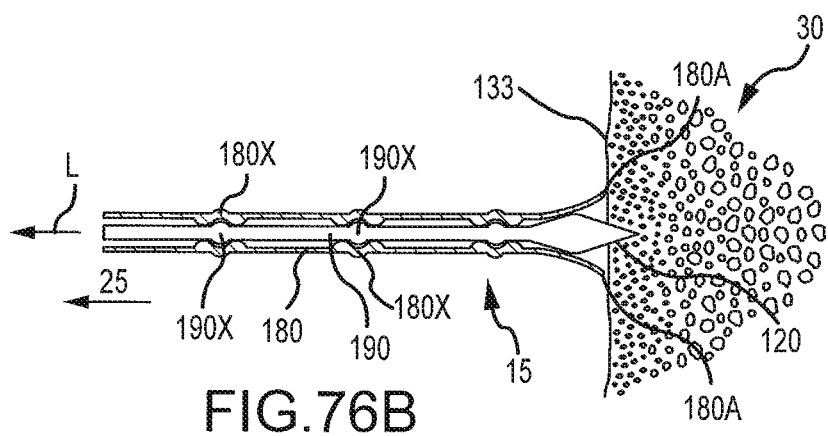

As shown in FIGS. 76A and 76B, which are similar respective views to FIGS. 75A and 75B, in one embodiment, the inner shaft 190 will have features 190X that expand and engage with features 180X of the outer shaft 180 when the inner shaft 190 is displaced relative to the outer shaft 180 such that the tip 120 has expanded the outer shaft 180 to form the shaft anchoring members 180A. Thus, the engagement of the features 180X, 190X can hold the shafts 180, 190 in a position relative to each other that maintains the tip 120 in a position to cause the anchoring members 180A to remain in an expanded, anchoring state, as shown in FIG. 76B. In some embodiments, the features 180X may be created in the inner circumference of the outer shaft 180 by forming dimples or radial crimp lines in the outside diameter of the outer shaft 180.

Figure 76C:
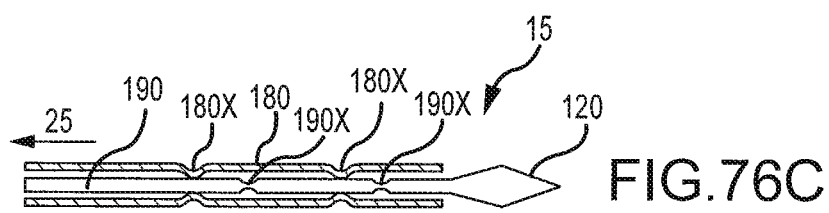
FIGS. 76C and 76D are similar respective views to FIGS. 76A and 76B, except of another embodiment.
Figure 76D:
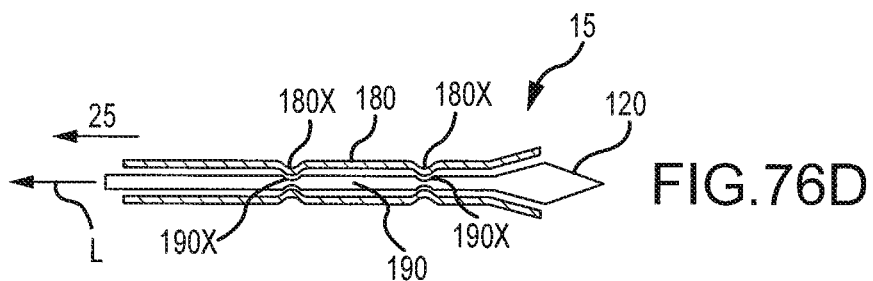

As can be understood from FIGS. 76C and 76D, which are similar respective views to FIGS. 76A and 76B, in some embodiments, the inner shaft 190 and the outer shaft 180 may have opposed interlocking features 180X, 190X defined along their respective lengths in the form of radial grooves 180X, 190X formed via dimpling or crimping.

In some embodiments, the intramedullary rods 15, 16 may be configured to be telescopic such that the actual overall length of the rods 15, 16 may be varied. Thus, in embodiments of the implant assembly 10 employing such length adjustable rods 15, 16, the rods 15, 16 may be both telescopic from the hub 20, on account of the attachment arrangement between the rod connector ends 25 and the hub 20, and telescopic along the length of the rods 15, 16, on account of the telescopic configuration of the shaft of the rods 15, 16. For a discussion of a telescopic rod configuration, reference is made to FIG. 60, which is a longitudinal cross section of such a rod 15, 16.

Figure 60:
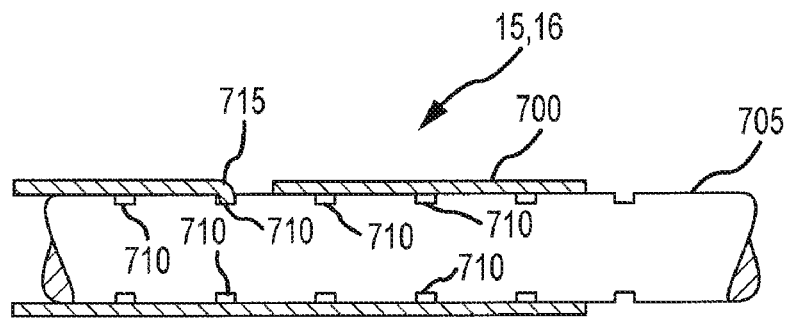
FIG. 60 is a longitudinal cross section of an intramedullary rod having a telescopic configuration and a clip or pin securing arrangement.

As shown in FIG. 60, the rods 15, 16 may include an outer shaft 700 and an inner shaft 705 telescopically located within the outer shaft 700. In one embodiment, the inner shaft 705 includes a series of transverse grooves, ridges, holes, notches, depressions, bumps or other engagement features 710 at generally even intervals along the length of the inner shaft 705. The outer shaft 700 includes radially inward engagement feature 715 that projects radially inward such that it can engage an engagement feature 710 on the inner shaft 705. Engagement of the radially inward engagement feature 710 with an engagement feature 710 on the inner shaft 705 can lock the inner shaft 705 in the outer shaft 700 at a desired telescopic point. Depending on the embodiment, the radially inward engagement feature 715 of the outer shaft 700 may be a spring clip formed of the outer shaft, a pawl tooth, a tab, or any other engagement feature that allows the engagement features 710, 715 to be engaged to lock the outer and inner shafts 700, 705 relative to each other after the length of the rods 15, 16 has been adjusted as desired. In some embodiments, the radially inward engagement feature 715 is configured to establish a ratchet arrangement with the engagement features 710 of the inner shaft 705. In some embodiments, the radially inward engagement feature 715 is non-releasable. In other embodiments, the radially inward engagement feature 715 is releasable such as, for example, in the case of a pawl tooth with a release lever or a inwardly biased tab engaged with a through hole in the inner shaft 705.

Figure 61:
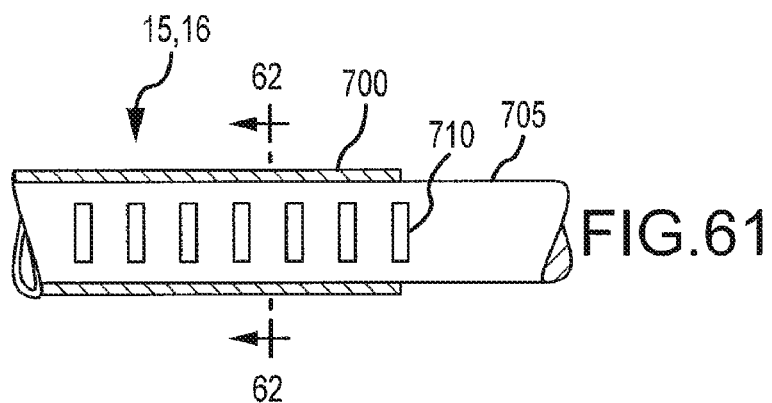
FIG. 61 is the same view as FIG. 60, except of an embodiment employing a crimp securing arrangement.
Figure 62A:
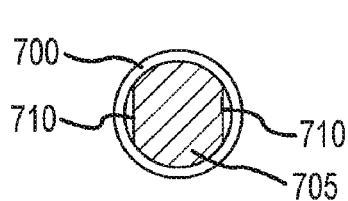
FIGS. 62A and 62B are transverse cross sections as taken along section line 62-62 of FIG. 61.
Figure 62B:
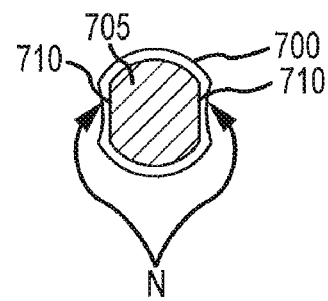

In some embodiments, the engagement arrangement between the outer and inner shafts 700, 705 may be accomplished via a crimp configuration. For example, as shown in FIG. 61 is the same view as FIG. 60, except of a crimp configuration, the inner shaft 705 may have the same engagement features 710 as described above with respect to FIG. 60. However, the outer shaft 700 is generally free of any engagement feature. Instead, as can be understood from FIGS. 62A and 62B, which are transverse cross sections of the rod 15, 16 as taken along section line 62-62 in FIG. 61, the outer shaft 700 does not engage the engagement features 710 of the inner shaft 705 in a non-crimped state (FIG. 62A), but does engage the engagement features 710 of the inner shaft 705 when crimped at arrows N (FIG. 62B), locking the shafts 700, 705 together.

Figure 63:
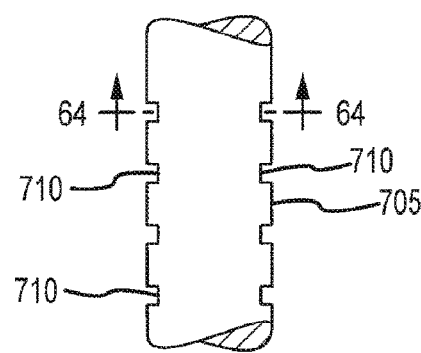
FIG. 63 is a longitudinal side view of the inner shaft.
Figure 64:
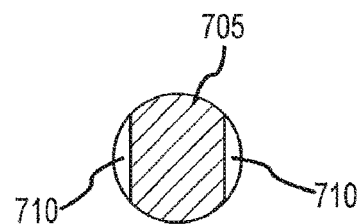
FIG. 64 is a transverse cross section as taken along section line 64-64 of FIG. 63.
Figure 65:
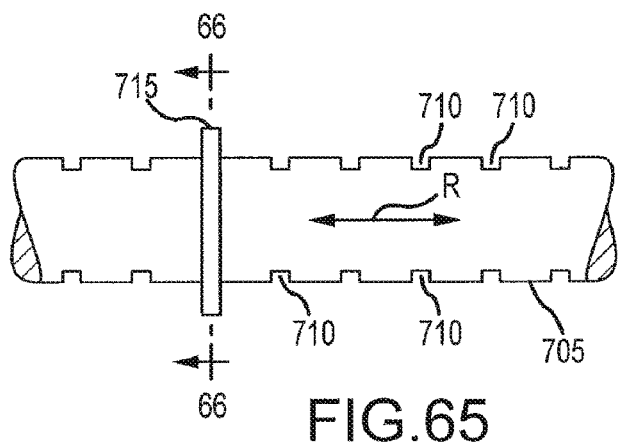
FIG. 65 is a longitudinal side view of the inner shaft wherein a spring clip is employed as part of the securing arrangement and the clip is not engaged with the notches.
Figure 66:
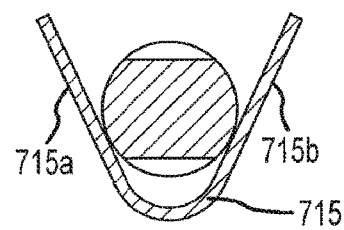
FIG. 66 is a transverse cross section as taken along section line 66-66 of FIG. 65.
Figure 67:
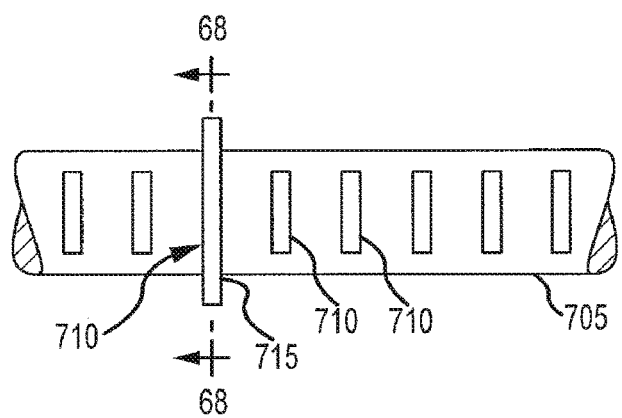
FIG. 67 is a longitudinal side view of the inner shaft wherein a spring clip is employed as part of the securing arrangement and the clip is engaged with the notches.
Figure 68:
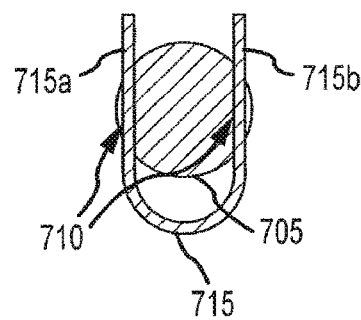
FIG. 68 is a transverse cross section as taken along section line 68-68 of FIG. 67.

In one embodiment, the engagement feature 715 of the outer shaft 700 may be in the form of a clip 715. In such an embodiment, as depicted in FIGS. 63 and 64, which are, respectively, a longitudinal side view of the inner shaft 705 and a transverse cross section as taken along section line 64-64 of FIG. 63, the shaft includes engagement features 710 similar to those described above with respect to FIG. 60. The outer shaft 700 is equipped with an engagement feature 715 in the form of a clip 715 biased radially inward. As can be understood from FIGS. 65 and 66, which are, respectively, a longitudinal side view of the inner shaft 705 and a transverse cross section as taken along section line 66-66 of FIG. 65, the inner shaft 705 is longitudinally displaceable relative to the clip 715 as indicated by arrow R when the inner shaft 705 is rotated such that the engagement features 710 of the inner shaft 705 are oriented away from engagement with the legs 715a, 715b of the clip 715. As can be understood from FIGS. 67 and 68, which are, respectively, a longitudinal side view of the inner shaft 705 and a transverse cross section as taken along section line 68-68 of FIG. 67, the inner shaft 705 is longitudinally fixed relative to the clip 715 when the inner shaft 705 is rotated such that the engagement features 710 of the inner shaft 705 are oriented into engagement with the legs 715a, 715b of the clip 715.

In one embodiment, the outer and inner shafts 700, 705 are capable of being fixed relative to each other via a sliding lock 725 as depicted in FIG. 69, which is a longitudinal cross section of the sliding lock 725 on the inner shaft 705. As can be understood from FIG. 69, in one embodiment, a holder 730 is supported off of the outer shaft 700 and includes housing 732 with a sloped inner face 735, balls 740, a plunger 745 and a helical spring 750. The balls 740 are located adjacent the outer surface of the inner shaft 705. The spring 750 extends about the inner shaft 705. The plunger 745 extends about the inner shaft 705 between the balls 740 and the spring 750. The spring 750 acts between the housing 732 and the plunger 745. The housing extends from the outer shaft 700 and about the inner shaft 705. The outer shaft 700 and housing 732 can be displaced freely in the direction of arrow S such that the spring 750 and plunger 745 causes the balls 740 to travel in the same direction along the inner shaft 700. Once a desired telescopic relationship between the outer and inner shafts 700, 705 is reached, displacement in a direction opposite arrow S is prevented by the wedging action of the sloped inner face 735 acting with the balls 740 against the inner shaft 705. Depending on the embodiment, the holder 730 can be supported off of the inner shaft 700, as opposed to the outer shaft 700. Also, the holder 730 can be configured to travel and lock in both directions, as opposed to a single direction.

In one embodiment, the shafts 700, 705 may be configured such that rotation of the shafts 700, 705 relative to each other causes the shafts 700, 705 to lock with respect to longitudinal displacement relative to each other. For example, as indicated in FIGS. 70A and 70B, which are transverse cross sections of the rods 15, 16, one or more balls 740 may be located between the inner circumferential surface 760 of the outer shaft 700 and the outer circumferential surface 765 of the inner shaft 705. As indicated in FIG. 70A, a feature 770 may extend from one of the surfaces 760, 765 that can be used to move the ball 740 along the surfaces 760, 765 as the shafts 700, 705 are rotated relative to each other as indicated by arrow H' and H". As shown in FIG. 70B, at after a certain amount of rotation, the ball 740 will wedge between the circumferential surfaces 760, 765, causing the shafts 700, 705 to lock together to prevent longitudinal displacement of the shafts 700, 705 relative to each other.

Figure 71A:
FIGS. 71A-71D are transverse cross sections of the outer and inner shafts individually and combined into a intramedullary rod, wherein rotation may expand and/or lock the rods.
Figure 71B:
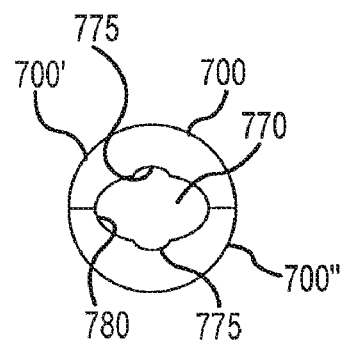

In some embodiments, the configuration of the shafts 700, 705 themselves results in locking of the shafts together with respect to preventing longitudinal displacement of the shafts relative to each other and/or may be employed to expand the shaft to allow the shaft to anchor in surrounding bone material. For example, as indicated in FIGS. 71A-71D, which are transverse cross sections of the shafts 700, 705, the rotation of the inner shaft 705 relative to the outer shaft 700 causes the outer shaft 700 to expand. This feature may be employed to lock the shafts 700, 705 relative to each to prevent longitudinal displacement of the shafts relative to each other. Additionally or alternatively, this feature may be used to expand the outer shaft 700 to anchor the shaft in surrounding bone material. In one embodiment, as shown in FIG. 71A, the inner shaft 705 may have a non-circular cross section, for example, an oval cross section. As shown in FIG. 71B, the outer shaft 700 may be sectioned into two halves 700', 700" and its interior space 770 may have a cross section that corresponds to the cross section of the inner shaft 705, for example, an oval cross section also. The oval cross section of the interior space 770 may have arcuate recesses 775 defined in the inner surface 780 of the interior space 770 that are located generally transverse to the major axis of the oval interior space 770.

Figure 71C:
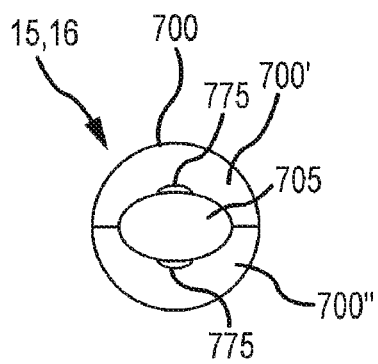
Figure 71D:
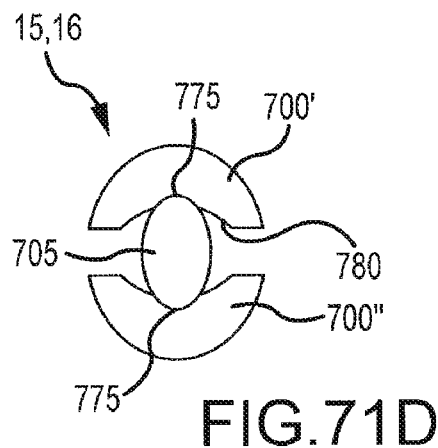

As illustrated in FIG. 71C, when the inner shaft 705 is positioned in the interior space 770 of the outer shaft 700 such that the major axis of the inner shaft oval cross section aligns with the major axis of the interior space cross section, the halves 700', 700" remain in contact or in an otherwise non-expanded state. As depicted in FIG. 71D, when the inner shaft 705 is positioned in the interior space 770 of the outer shaft 700 such that the major axis of the inner shaft oval cross section is transverse with the major axis of the interior space cross section, the narrow oval ends of the inner shaft cross section are received in the recesses 775 and the halves 700', 700" are expanded away from each other. The interaction of the narrow oval ends of the inner shaft cross section with the recesses 775 creates a resting point to maintain the outer shaft in the expanded state. Such an expanded condition of the outer shaft 700 creates sufficient frictional interaction between the outer and inner shafts 700, 705 to lock the shafts together to prevent longitudinal displacement of the shafts relative to each other.

Figure 72:
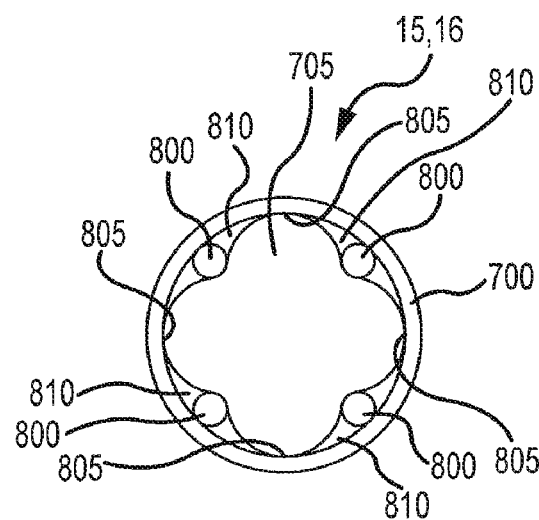
FIG. 72 is a cross section of the shafts locked together via inserted pins.

In one embodiment, the pins 800 or other members 800 are inserted between the outer and inner shafts 700, 705 to lock the shafts together with respect to preventing longitudinal displacement of the shafts relative to each other. For example, as indicated in FIG. 72, which is a cross section of the shafts 700, 705, pins 800 may be inserted into the space between the outer surface of the inner shaft 705 and the inner surface of the outer shaft 700. The pins 800 may be so inserted once the shafts are longitudinally positioned relative to each other as desired. In one embodiment, the inner shaft outer surface may have multiple ridges 805 and troughs 810. The ridges 805 contact the inner surface of the outer shaft 700, and the pins 800 are received in the space between the inner surface of the outer shaft and the outer surface of the inner shaft as provided by the troughs 810. In one embodiment, the pins 800 have a tapered cross section such that the narrow ends of the pins 800 are the leading ends of the pins 800 when inserted into the troughs 810. As the tapered pins 800 are increasingly inserted into the troughs 810, the increasing width of the pins creates a bind between the pins, the inner shaft and the outer shaft, the bind being sufficient to lock the shafts in place relative to each other.

Figure 73A:
FIGS. 73A and 73B are longitudinal cross sections of portions of the rod, wherein a portion of the rod may be deformable.
Figure 73B:

In one embodiment, a portion of the rod 15, 16 may deform to cause a locking condition between the outer and inner shafts 700, 710 and/or cause the outer sleeve to anchor into surrounding bone material. For example, as can be understood from FIGS. 73A and 73B, which are longitudinal cross sections of portions of the rod 15, 16, a portion of the rod 15, 16 may be equipped with a collapsible or otherwise deformable sleeve 820. For example, as depicted in FIG. 72A, the sleeve 820 may be located between the outer and inner shafts 700, 705. Applying a force against the sleeve 820 via either of the shafts 700, 705 causes the sleeve 820 to deform (FIG. 72B), causing expansion of the sleeve 820 and binding of the sleeve and shafts together and preventing longitudinal displacement of the shafts relative to each other. In another embodiment, either the outer or inner shaft 700, 705 may be caused to deform as described with respect to the sleeve 820, causing the shafts 700, 705 to bind together. Additionally or alternatively, the expanding of the sleeve may result in anchoring into the surrounding bone material.

As stated above, the intramedullary rods 15, 16 may have an outer shaft 700 and an inner shaft 705 telescopically located within the outer shaft 700. Such a telescopic arrangement allows the rods 15, 16 to be lengthened or shortened to provide a desired overall length for the rods 15, 16. Thus, the telescopic nature of such rods 15, 16 may be employed to position a rod free end 30 a desired distance from the edge of the hub 20. As can be understood from the preceding discussion regarding FIGS. 60-72, once the shafts 700, 705 are longitudinally positioned relative to each other to provide a rod 15, 16 having a desired length, the shafts 700, 705 may be locked together employing the above-described engagement mechanisms.

Figure 82:
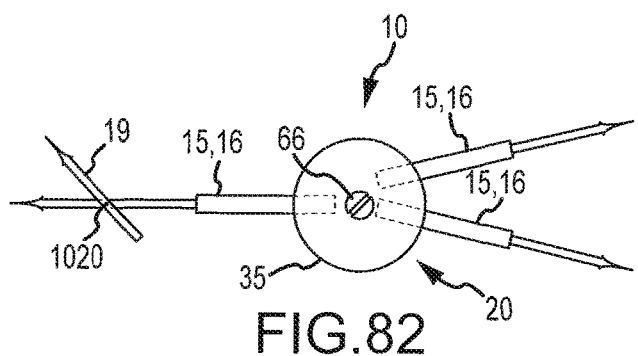
FIG. 82 is a plan view of a rods coupled to a plate, wherein rods may be coupled to rods.

As can be understood from FIG. 82, which is a plan view of an alternative embodiment of the rods, the rods 15, 16 may be configured such that additional rods 18 may extend from rods 15, 16 extending from the plate 35 used to form the hub 20. The additional rod 19 may be coupled a rod 15, 16 via a pin, screw or other joining member or arrangement. Generally, the additional rod 19 may be configured as any of the other rods 15, 16 disclosed herein, except such rod 19 is configured to be coupled to and supported off of the rods 15, 16.

Figure 17:
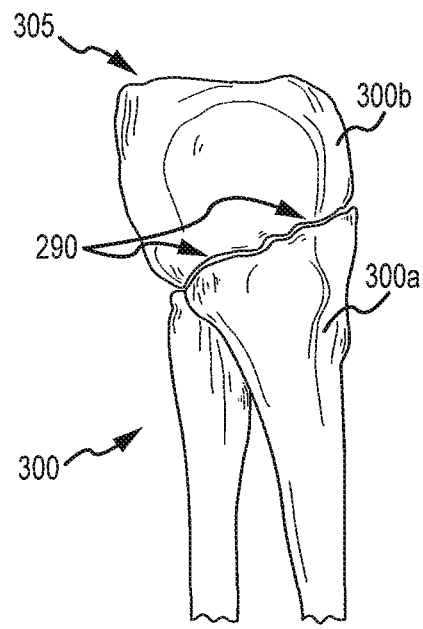
FIG. 17 is a plan view of a bone with a fracture.

For a discussion of a method of employing the implant assembly 10 described above with respect to FIGS. 1-16C to treat a bone fracture, reference is now made to FIGS. 17-24, which illustrate the implant assembly 10 being assembled in a bone fracture over a series of steps. As shown in FIG. 17, a fracture 290 has occurred in a bone 300 near a joint region 305 of the bone 300 resulting in a proximal bone portion 300a and a distal bone portion 300b. While the fracture illustrated in FIG. 17 is that of a distal radial fracture 290, the method and implant assembly 10 depicted in FIGS. 17-24 is readily applicable to other types of fractures (e.g., fractures near or away from a joint region of a bone, multi-bone fragment fractures, spiral fractures, etc.) in other types of bones (e.g., femurs, tibia, humerus, ulna, ribs, collar bone, pelvis, finger, toes, vertebra, etc.).

Figure 18:
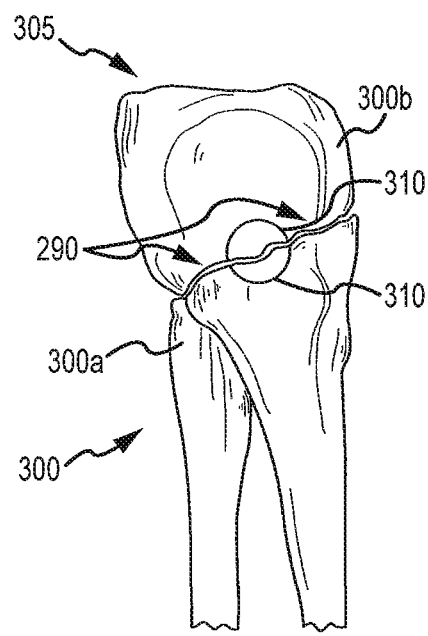
FIG. 18 is the same view of the bone of FIG. 17 subsequent to the creation of an access window in the bone at the fracture.

As shown in FIG. 18, a small access window 310 may be created in the bone 300 across the fracture 290. The access window 310 may be formed in the dorsal or volar surface the bone or another surface of the bone. The access window 310 may have a diameter of between approximately 0.05" and approximately 3". The access window 310 may be formed via a minimally invasive or percutaneous access in the patient's soft tissue extending over the fracture 290. In some embodiments and/or some types of fractures, the creation of an access window 310 may not be necessary, as the implant may simply be delivered into the bone via the fracture itself. In some embodiments, as described below, the implant assembly 10 is assembled within the fracture and inside the bone. In other embodiments, the implant assembly 10 may be assembled on the fracture and on the outside of the bone.

Figure 19:
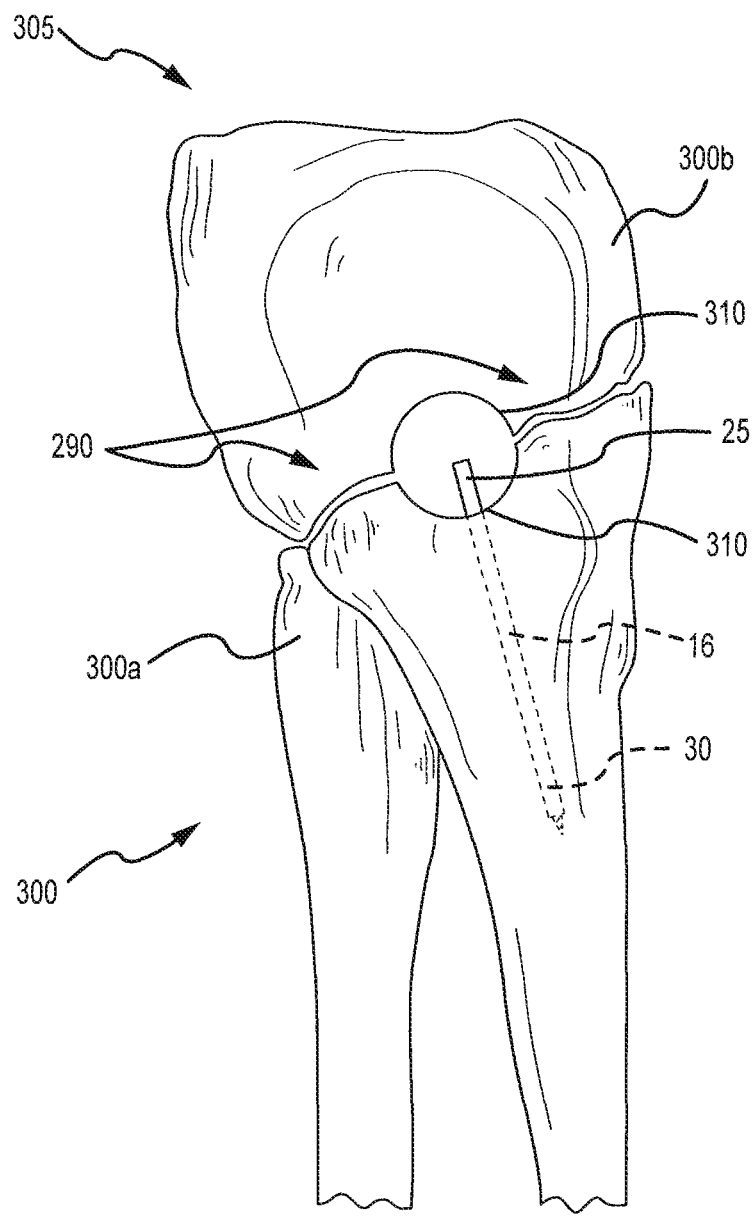
FIG. 19 is the same view of the bone of FIG. 18 subsequent to the delivery of a proximal intramedullary rod into the interior of the bone via the access window.

As explained above with respect to FIGS. 14A-16C, certain intramedullary rods 16 have free ends 30 configured to interface with bone that is between the fracture location and a shaft of the bone or a portion of the bone that is opposite the fracture from a joint surface. In the context of a distal radial fracture, such an intramedullary rod 16 may be considered a proximal intramedullary rod 16 that extends proximally from the fracture 290. As illustrated in FIG. 19, the access window 310 is used to insert the proximal rod 16 into the interior of the proximal bone portion 300a such that the free end 30 resides deep within interior of the proximal bone portion 300a and the connector end 25 is located within the access window 310 and terminates near the fracture 290. The free end 30 of the proximal rod 16 may have any of the tip and anchor features described above with respect to FIGS. 4A-4C and 14A-16C. Therefore, once the free end 30 and, more specifically, the entire proximal rod 16 is positioned as desired within the interior of the proximal bone portion 300a, the anchoring features 135, 205 described with respect to FIGS. 14A-16C may be deployed to fix the free end 30 in place within the bone interior. It should be noted that while a single proximal rod 16 is shown as being inserted proximal of the fracture 290, in some embodiments of the implant assembly 10 and/or for some types of fractures, there may be two, three or more such proximal rods 16 delivered to the interior of the proximal bone portion 300a.

Figure 20:
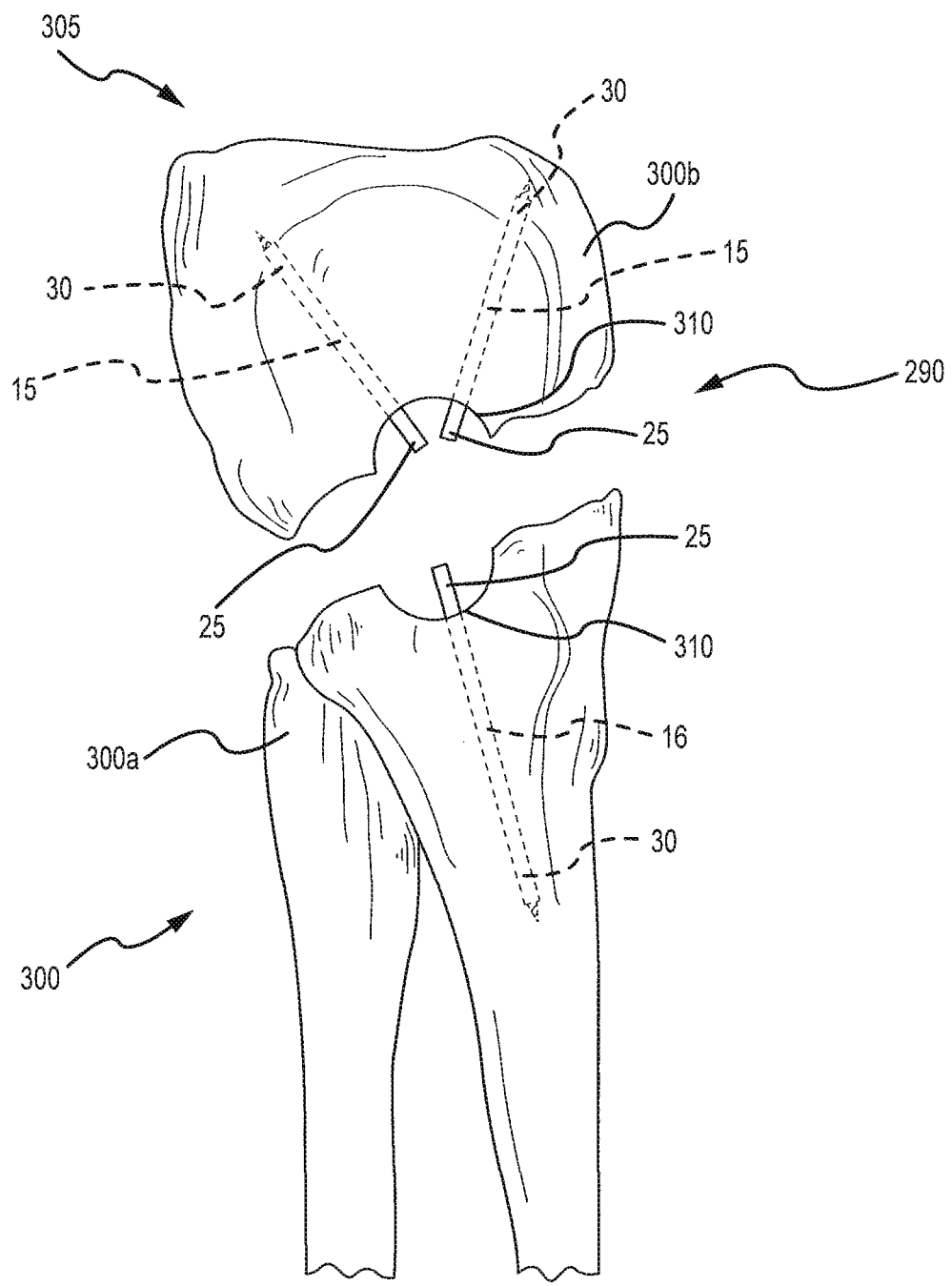
FIG. 20 is generally the same view of the bone of FIG. 19, except the bone portions are separated and subsequent to the delivery of the distal intramedullary rods into the interior of the bone via the access window.

As can be understood from FIG. 20, the distal bone portion 300b and the proximal bone portion 300a may be displaced relative to each other (e.g., tilted, spread apart, etc.) to facilitate of rods 15, 16 through the access window 310 or the fracture 290 itself. In some cases, such displacement of the bones portions 300a, 300b relative to each other may not be necessary to facilitate the delivery of the rods 15, 16.

As explained above with respect to FIGS. 4A-4C and 13A-13C, certain intramedullary rods 15 have free ends 30 configured to interface with bone that is between the fracture location and a joint surface. In the context of a distal radial fracture, such an intramedullary rod 15 may be considered a distal intramedullary rod 15 that extends distally from the fracture 290. As illustrated in FIG. 20, the access window 310 is used to insert the distal rods 15 into the interior of the distal bone portion 300b such that the free ends 30 reside deep within interior of the distal bone portion 300b and the connector ends 25 are located within the access window 310 and terminate near the fracture 290. The free ends 30 of the distal rod 16 may have any of the tip and anchor features described above with respect to FIGS. 4A-4C and 13A-13C. Therefore, once the free ends 30 and, more specifically, the entire distal rods 15 are positioned as desired within the interior of the distal bone portion 300b, the anchoring features 135 described with respect to FIGS. 13A-13C may be deployed to fix the free ends 30 in place within the bone interior. It should be noted that while two distal rods 15 are shown as being inserted distal of the fracture 290, in some embodiments of the implant assembly 10 and/or for some types of fractures, there may be one, three or more such distal rods 15 delivered to the interior of the distal bone portion 300b.

Figure 21:
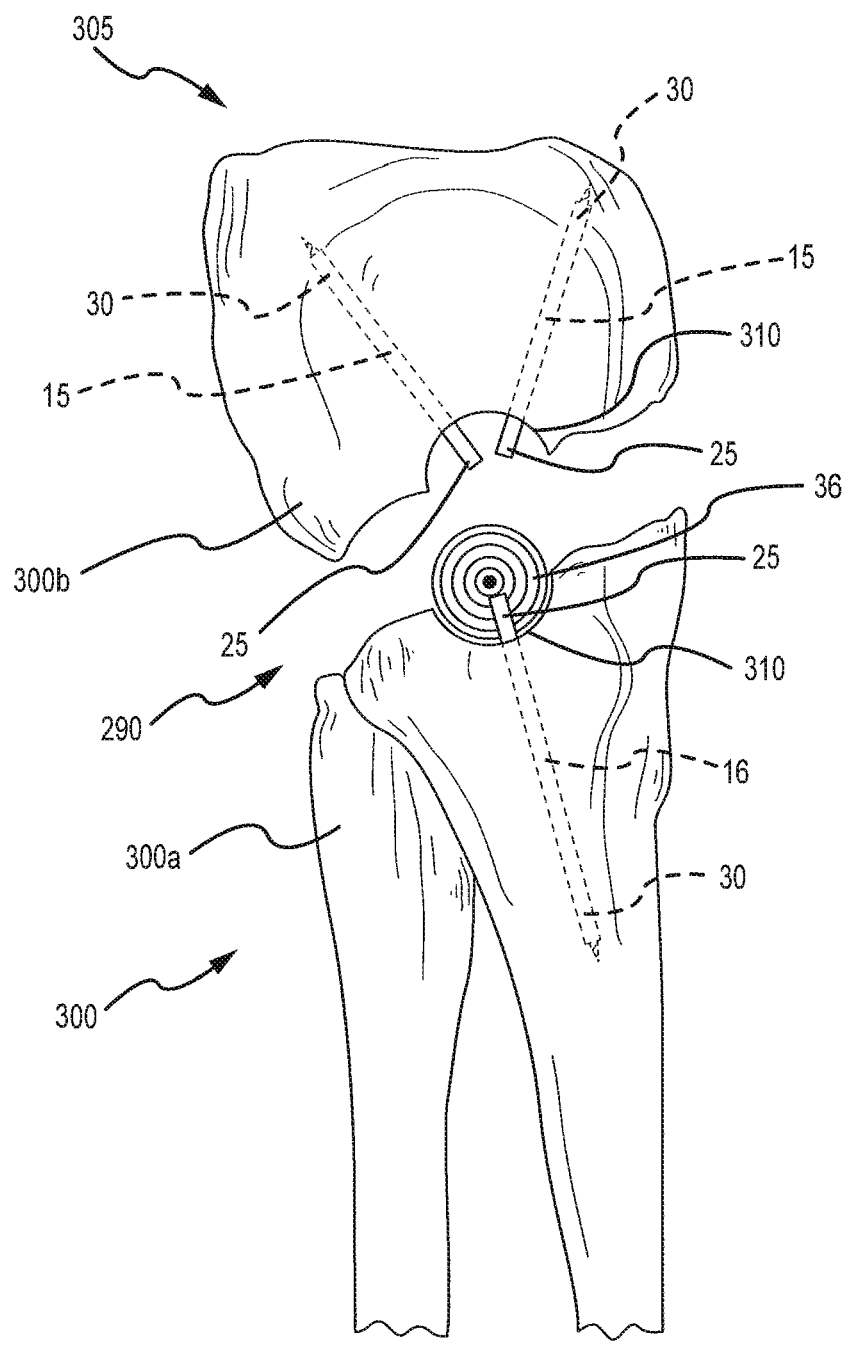
FIG. 21 is the same view of the bone of FIG. 20 subsequent to the delivery of a bottom plate of the hub into the interior of the bone via the access window.

As shown in FIG. 21, a bottom plate 36 having the features described with respect to FIGS. 5-6C or FIG. 10 may be delivered to the access window 310 with the interior surface 56 of the bottom plate 36 facing upward. While FIG. 21 shows the bottom plate 36 as being delivered subsequent to the delivery of the rods 15, 16, the bottom plate 36 may be delivered prior to the delivery of the rods 15, 16 or between the delivery of the various rods 15, 16.

Figure 22:
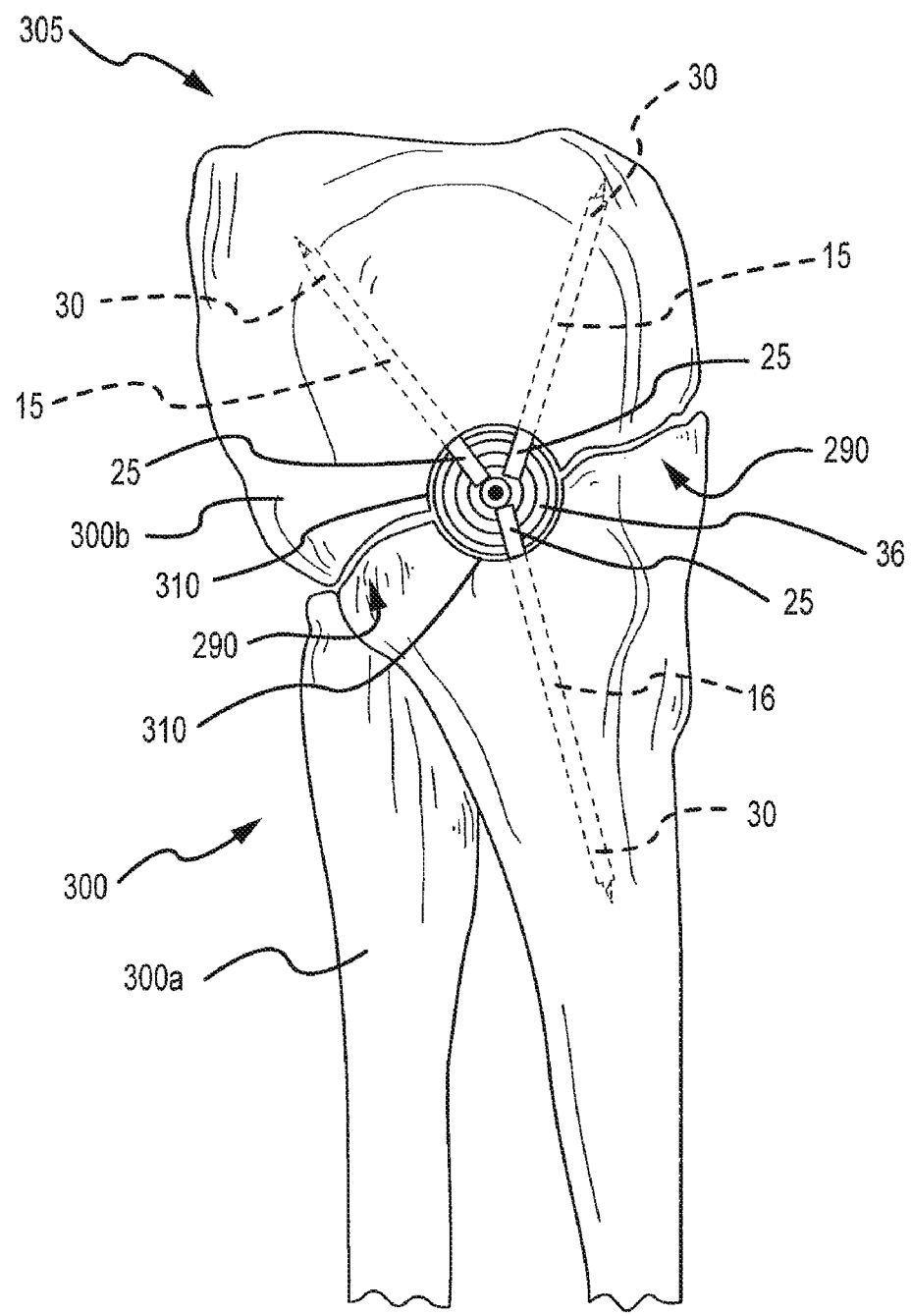
FIG. 22 is generally the same view of the bone of FIG. 20, except the bone portions are no longer separated and subsequent to the desired alignment of the rod connector ends relative to the bottom plate.
Figure 23:
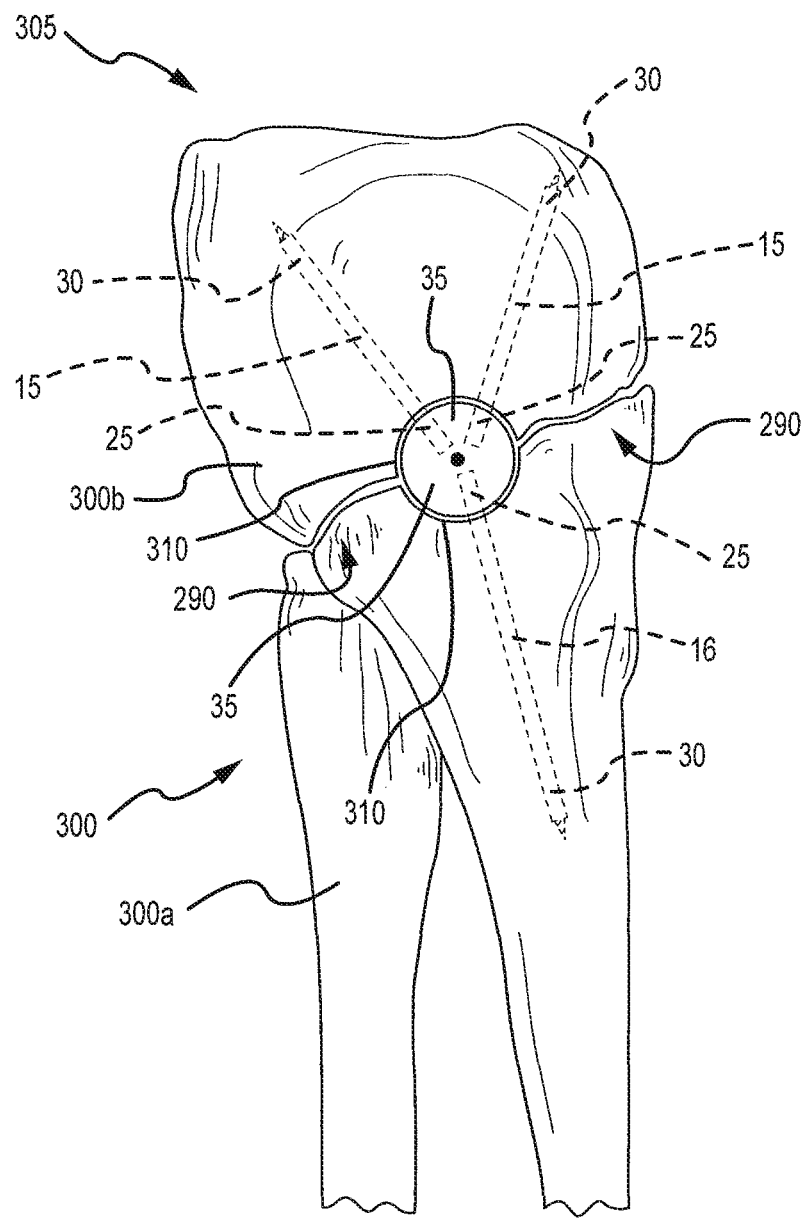
FIG. 23 is the same view of the bone of FIG. 22 subsequent to the delivery of a top plate of the hub into the interior of the bone via the access window.

As indicated in FIG. 22, the bottom plate 36, the connector ends 25 of the various rods 15, 16, and the bone portions 300a, 300b may be positioned relative to each other as desired to bring about the arrangement of the bone portions 300a, 300b that will restore the bone 300 to its pre-fractured alignment and configuration. As illustrated in FIG. 23, the upper plate 35 may then be placed over the bottom plate 36 and junction of the various rod connector ends 25 with the interior surface 55 of the upper plate 35 facing downward. In doing so, the various features (e.g., 75, 85 in FIGS. 9A-9C or 110, 111, 115 in FIG. 12) of the rod connector ends 25 are caused to interface as discussed above with the respective corresponding features (e.g., 60, 70 in FIG. 5-8 or 90, 105 in FIGS. 10-11) of the upper and lower plates 35, 36 of the hub 20.

Figure 24:
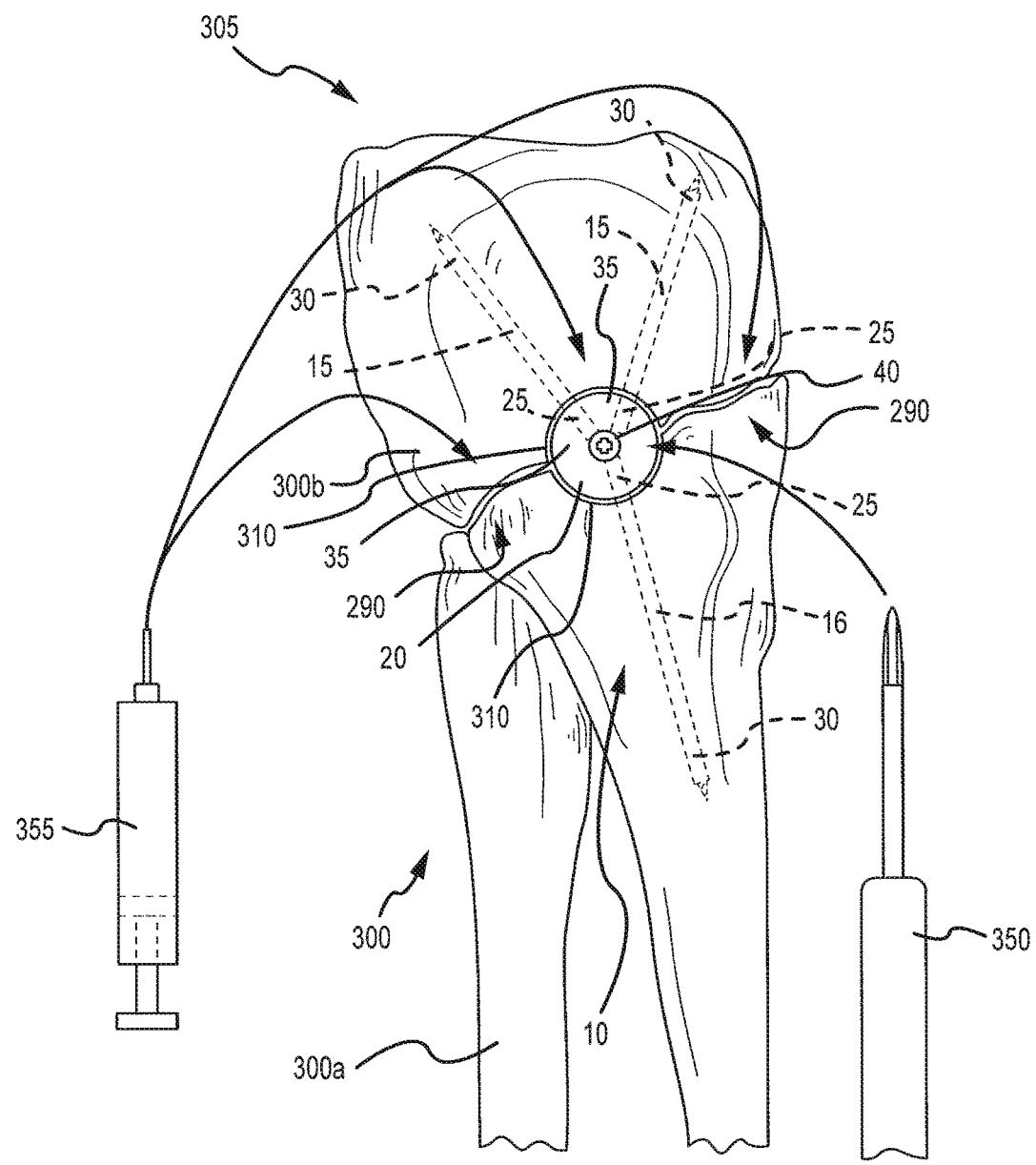
FIG. 24 is the same view of the bone of FIG. 23 subsequent to the implant being secured into a rigid implant assembly and the delivery of bone paste.

As depicted in FIG. 24, the setscrew 40 is then inserted into the center hole of the hub 20 to join the plates 35, 36 of the hub 20 together about the connector ends 25 of the various rods 15, 16. Tightening the setscrew 40 down via a screwdriver 350 results in a rigid implant assembly like discussed above with respect to FIGS. 1-3 (in the context of plate and rod connector end embodiments discussed with respect to FIGS. 5-9C) or similar thereto (in the context of plate and rod connector end embodiments discussed with respect to FIGS. 10-12). The rigid implant assembly 10 secures the proximal bone portion 300a to the distal bone portion 300b in a desired relationship that is believed to lead to the bone 300 healing in its pre-fractured alignment and configuration. As indicated by the arrows leading from the syringe 355, bone paste, bone substitute or bone growth inducing material may be delivered to the fracture 290 and about the implant hub 20 to facilitate healing of the fracture and the securing of the implant assembly 10 at its implanted location.

All of the above mentioned steps, including the delivery of components of the implant assembly 10 and the assembly of the implant assembly 10 within the bone fracture 290 and interior of the bone 300, may be accomplished via a percutaneous or minimally invasive opening in the soft tissue neighboring the fracture 290 via minimally invasive surgical procedures and tools.

Figure 78:
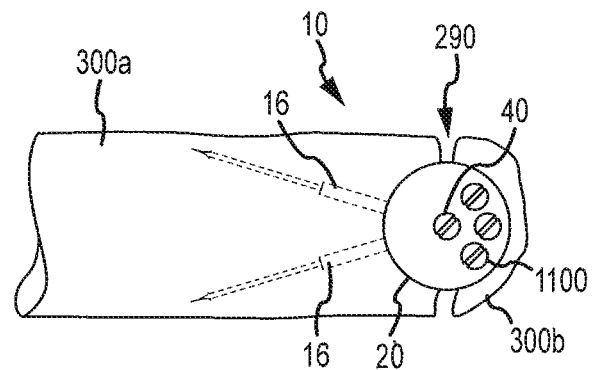
FIG. 78 is a plan view of the implant assembly implanted at a bone fracture, wherein the implant assembly employs a hub that engages the bone material.

While the embodiment depicted in FIG. 24 illustrates the distal bone 300b and proximal bone portion 300a are held together via an implant assembly 10 having a hub 20 with distal rods 15 and proximal rods 16 respectively anchored in the distal and proximal bone portions, in other embodiments, the implant 10 may only employ proximal or distal rods, the hub 20 instead being adapted to engage bone material. For example, as shown in FIG. 78, which is a plan view of the implant assembly 10 implanted at a bone fracture 290, the hub 20 is configured to anchor to or engage with bone material on one side of the fracture 290 (e.g., on the distal bone portion 300b in the embodiment depicted in FIG. 78), and rods 16 extend into the bone portion 300a on the other side of the fracture 290. The hub 20 may be configured to receive anchoring members 1100, for example, bone screws 1100 that extend from the hub 20 into adjacent bone material of the distal bone portion 300b, securing the hub 20 to the distal bone portion 300b. Rods 16 proximally extend from the hub 20 in a manner as described above to anchor in bone material of the proximal portion 300a. The implant assembly 10 may then be employed to treat the fracture 290. While the embodiment discussed with respect to FIG. 78 is discussed with respect to the hub 20 being engaged with the distal portion 300b and the rods 16 being engaged with the proximal portion 300a, in other embodiments and types of fractures, the opposite with be true. Depending on the embodiment and the type of fracture, bone cement may be employed in place of or in addition to the screws 1100.

While the embodiment depicted in FIG. 24 illustrates an implant assembly 10 including a single hub 20 and treating a single fracture 290, in other embodiments, the implant assembly 10 may include two or more hubs 20 joined together via one or more intermediate rods 17. For example, as shown in FIG. 80, which is a plan view of such a multiple hub embodiment, the implant assembly 10 includes first and second hubs 20 on generally opposite ends of the implant assembly 10, the first and second hubs 20 being joined together via one or more intermediate rods 17 using rod/hub coupling arrangements similar to any of those described above. Proximal rods 16 extend from one of the hubs 20 to engage bone material at a first fracture, and distal rods 15 extend from the other of the hubs 20 to engage bone material at a second fracture. Thus, for example, in a dual fracture of a long bone such as a femur, where a first fracture is at the femoral head and the second fracture is at the femoral condyles, one hub 20 may be located at the first fracture, the proximal rods 16 extending across the first fracture and into the femoral head region. The second hub 20 may be located at the second fracture, the distal rods 15 extending across the second fracture and into the femoral condyles. The hubs 20 are joined together via the intermediate rod 17, which extends through the length of the femur. The intermediate rod 17 may couple to the hubs 20 via any of the above described rod/hub coupling arrangements, and the intermediate rod 17 may have a fixed length or an adjustable length as described above with respect to the other rods 15, 16. In some embodiments, one or both of the hubs 20 may be configured for direct engagement with bone material, as described above with respect to FIG. 78.

For a discussion of another embodiment of an intramedullary implant assembly 10, reference is made to FIG. 25, which is a plan view of a proximal locking plate 36. As shown in FIG. 25, the proximal locking plate 36 includes holes 400 for receiving therein and coupling to connector ends 25 of proximal intramedullary rods 16. The proximal locking plate 36 also includes a center hole 405 and a slot 410 leading thereto. The holes 400 are evenly radially distributed about the center hole 405 near the outer circumferential edge 415 of the plate 36. The slot 410 extends from the center hole 405 and the outer edge 415. The slot 410 and center hole 405 are used to couple the proximal plate 36 to a distal plate 35 as described below.

As shown in FIG. 26, which is a plan view of a distal locking plate 35, the distal locking plate 35 includes holes 400 for receiving therein and coupling to connector ends 25 of distal intramedullary rods 15. The distal locking plate 35 also includes a center locking pin 420. The holes 400 are evenly radially distributed about the center locking pin 420 near the outer circumferential edge 415 of the plate 35. The center locking pin 420 is configured to be slid via the slot 410 into the center hole 405. The center locking pin 420 and center hole 405 interlock to couple the proximal plate 36 to a distal plate 35 as described below.

Figure 56:
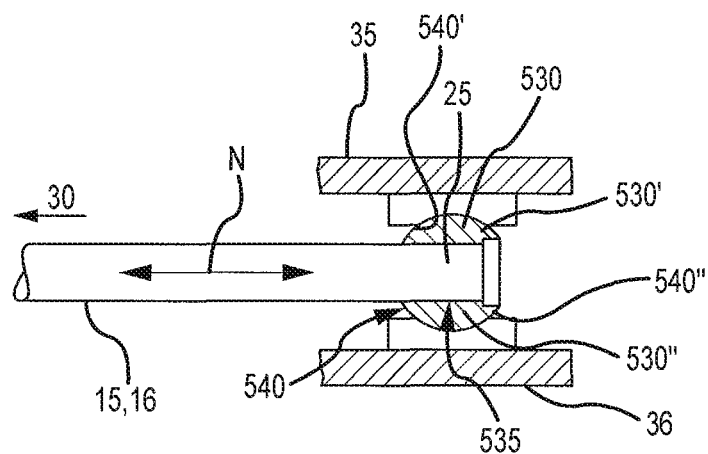
FIG. 56 is a side view of a rod connector end having the ball end connection arrangement.
Figure 57:
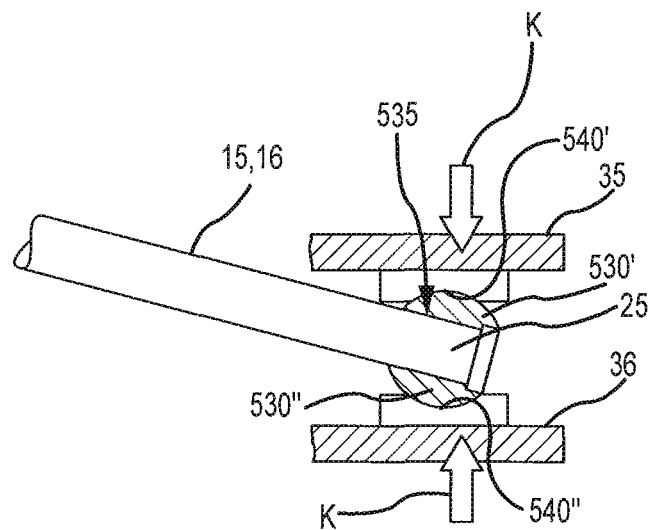
FIG. 57 is the same view as FIG. 56, except a securing force is being applied to the ball connection arrangement.

As can be understood from FIGS. 27 and 28, which are side elevation views of intramedullary rods 15, 16 that may be employed as part of the implant assembly 10, the rods 15, 16 have a connector end 25 and a free end 30. The connector end 25 is configured to be securely connected to any of the holes 400 in either of the plates 35, 36. The connector ends 25 and holes 400 may have a mechanical engagement arrangement such as, for example, a bayonet lock, threads, interference fit, setscrew, ball joints (e.g., as depicted in FIGS. 56 and 57), ball and cup connection (e.g., as depicted in FIGS. 58A-58E), etc. to fixedly connect a connector end 25 to a hole 400. The tips 120 of the rods 15, 16 may have any one or more of the features described above with respect to FIGS. 4A-4C. As can be understood from FIG. 28, the tips 120 may be equipped with anchor systems 135 that may be configured and deployed as discussed above with respect to FIGS. 13A-16C.

Figure 29:
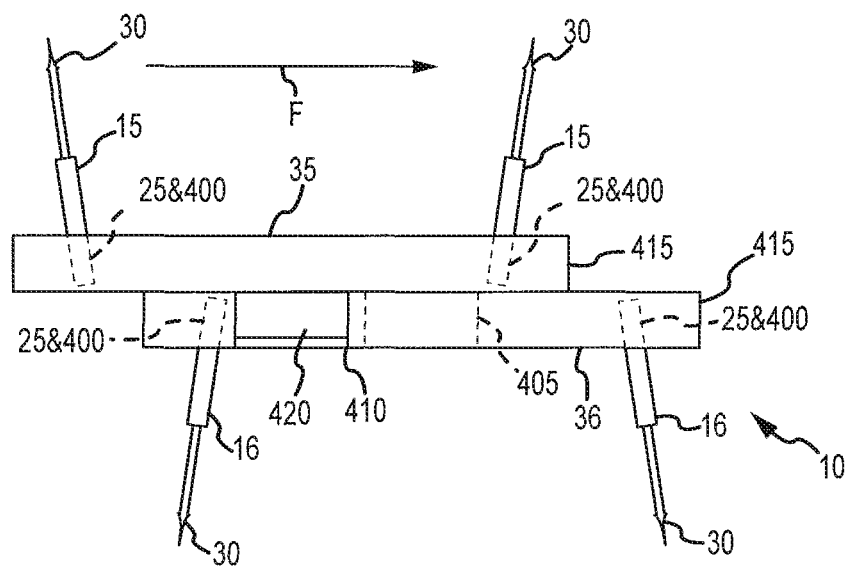
FIG. 29 is a side elevation view of the implant assembly in the process of having the plates slide together.
Figure 30:
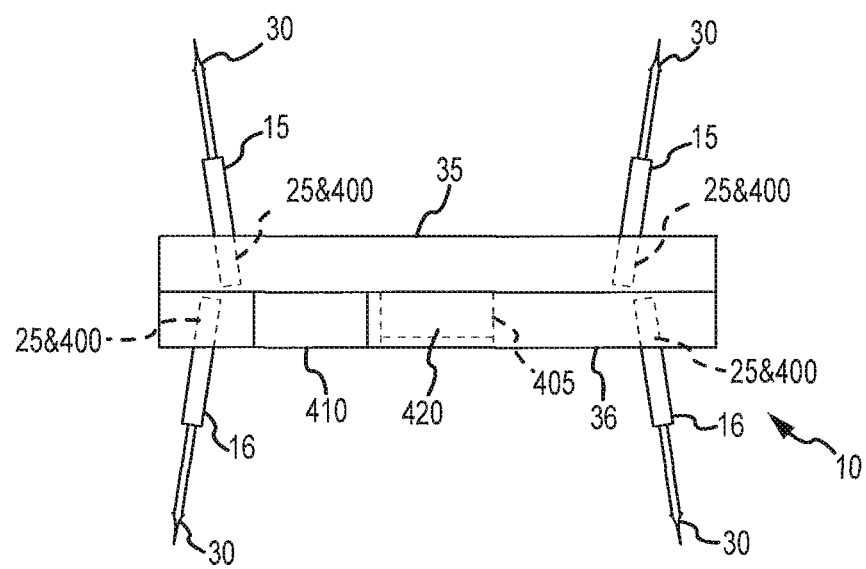
FIG. 30 is a side elevation view of the implant assembly in a fully assembled state.

As can be understood from FIGS. 29 and 30, which are side elevation views of the implant assembly 10 being assembled, the distal and proximal rods 15, 16 are respectively coupled to the distal and proximal plates 35, 36 via the rod connector ends 25 being mechanically connected in the holes 400. The faces of the plates 35, 36 are abutted together, and the center pin 420 is received in the slot 410 and slid in the direction of the center hole 405 as indicated by arrow F in FIG. 29. As shown in FIG. 30, once the center pin 420 is fully received in the center hole 405, a mechanical locking feature 425 (e.g., detent, interference fit, etc.) may cause the center pin 420 to be locked in the center hole 405. The result is a rigidly and securely assembled implant assembly 10 assembled from the plates 35, 36 and rods 15, 16.

Figure 31:
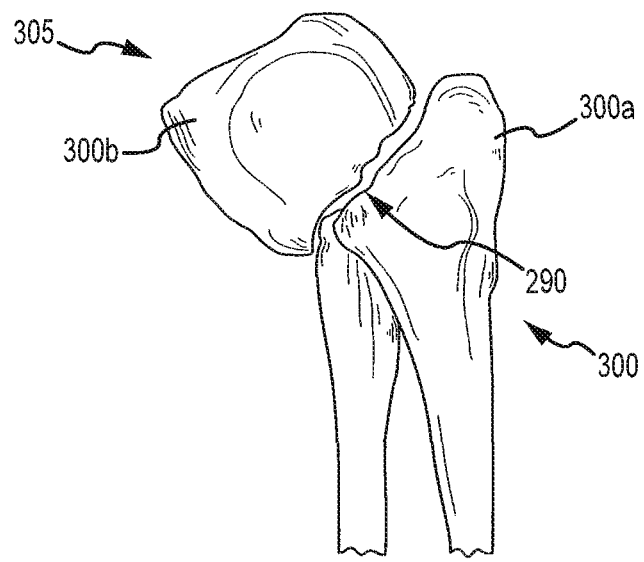
FIG. 31 is a view of a bone having a fracture.

For a discussion of a method of repairing a fracture employing the implant assembly 10 described with respect to FIGS. 25-30, reference is made to FIGS. 31-41, which are the same view of a bone with a fracture as the implant assembly 10 is being assembled in the fracture via percutaneous or minimally invasive delivery and assembly methods. As shown in FIG. 31, the bone 300, which in this example, is a distal radius, has suffered a Colles' fracture 290, resulting in a proximal bone portion 300a and a distal bone portion 300b. Of course, the implant assembly 10 and method provided below is applicable to a wide variety of bones and fractures and should not be limited to the following discussion.

Figure 32:
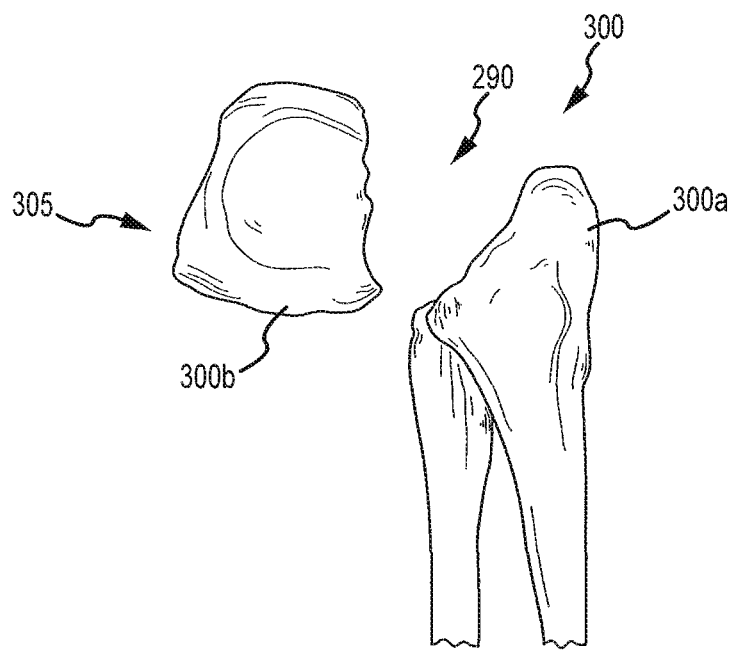
FIG. 32 is the same view as FIG. 31, except the distal and proximal bone portions are displaced from each other.
Figure 33:
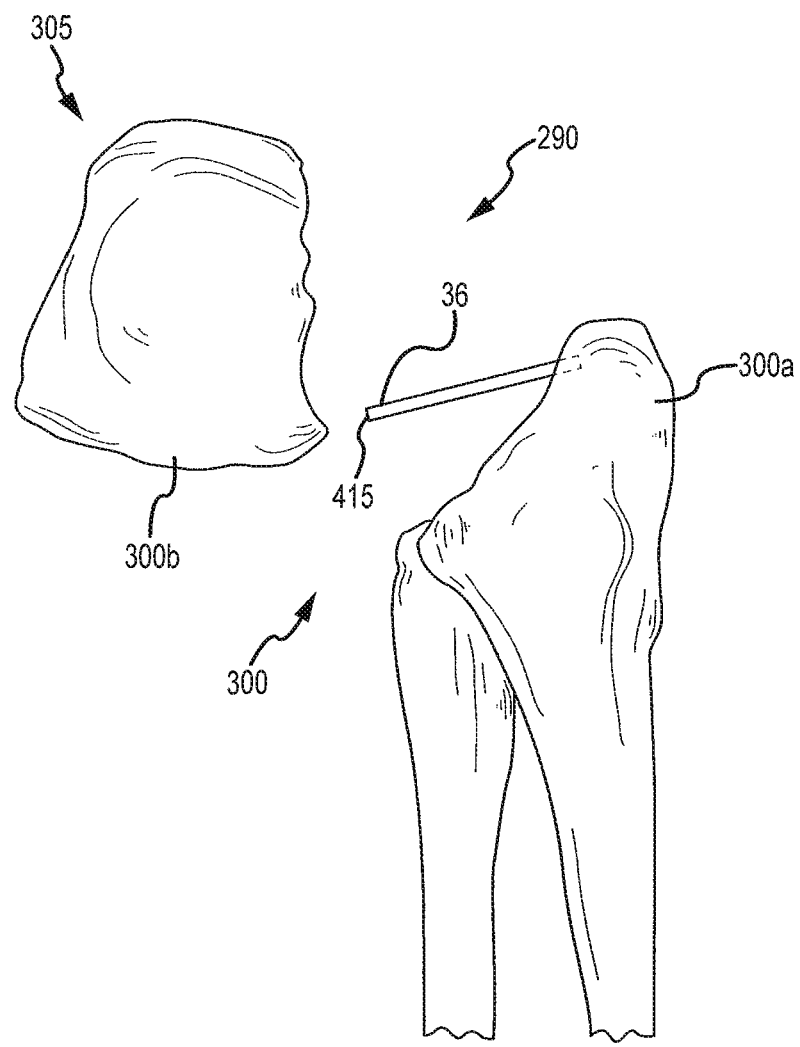
FIG. 33 is the same view as FIG. 32, except the proximal plate has been implanted.

As illustrated in FIG. 32, the distal bone portion 300b may be displaced to expose the fracture surface of the proximal bone portion 300a. As indicated in FIG. 33, the proximal locking plate 36 may be press fit into the trabecular bone such that the plate 36 extends generally transverse to the axis of the bone 300 and a face of the plate 36 faces towards the fracture surface of the proximal bone portion 300a. In one embodiment, the plate 36 may be positioned to be parallel to the fracture. The plate 36 serves as a template for the proximal rods 16. The angle of the plate 36 relative to the fracture surface of the proximal bone portion 300a may require preoperative surgical planning.

Figure 34:
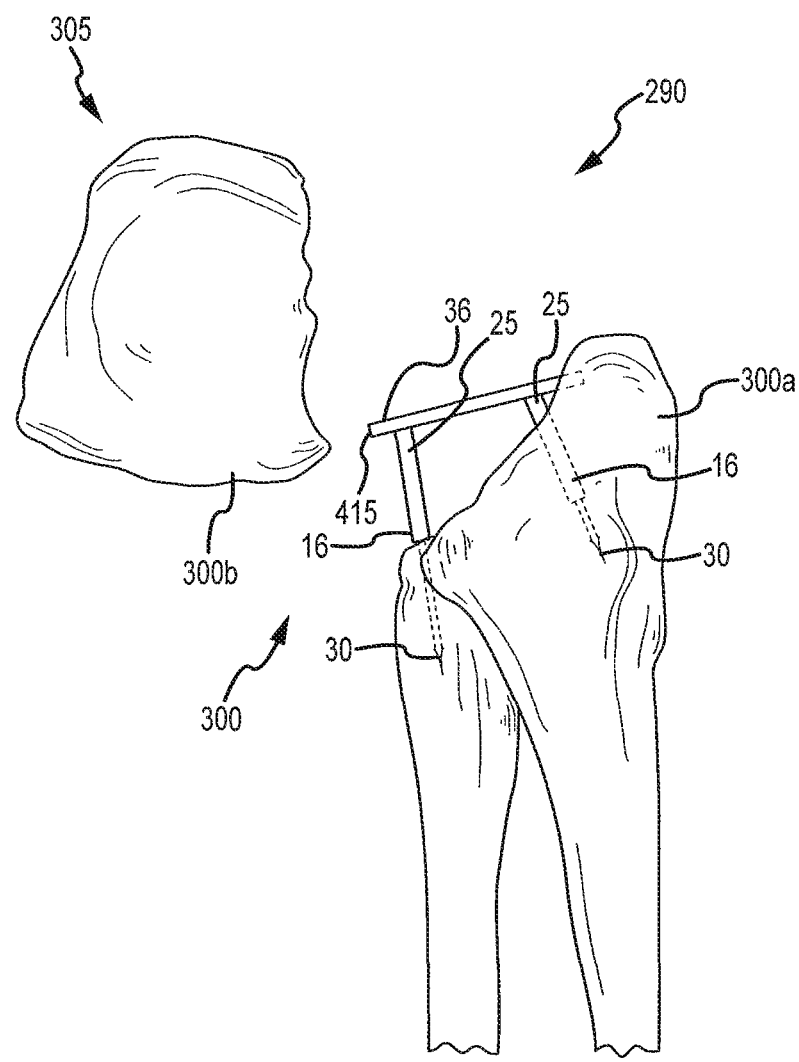
FIG. 34 is the same view as FIG. 33, except the proximal intramedullary rods have been coupled to the proximal plate and inserted into the proximal bone portion.
Figure 35:
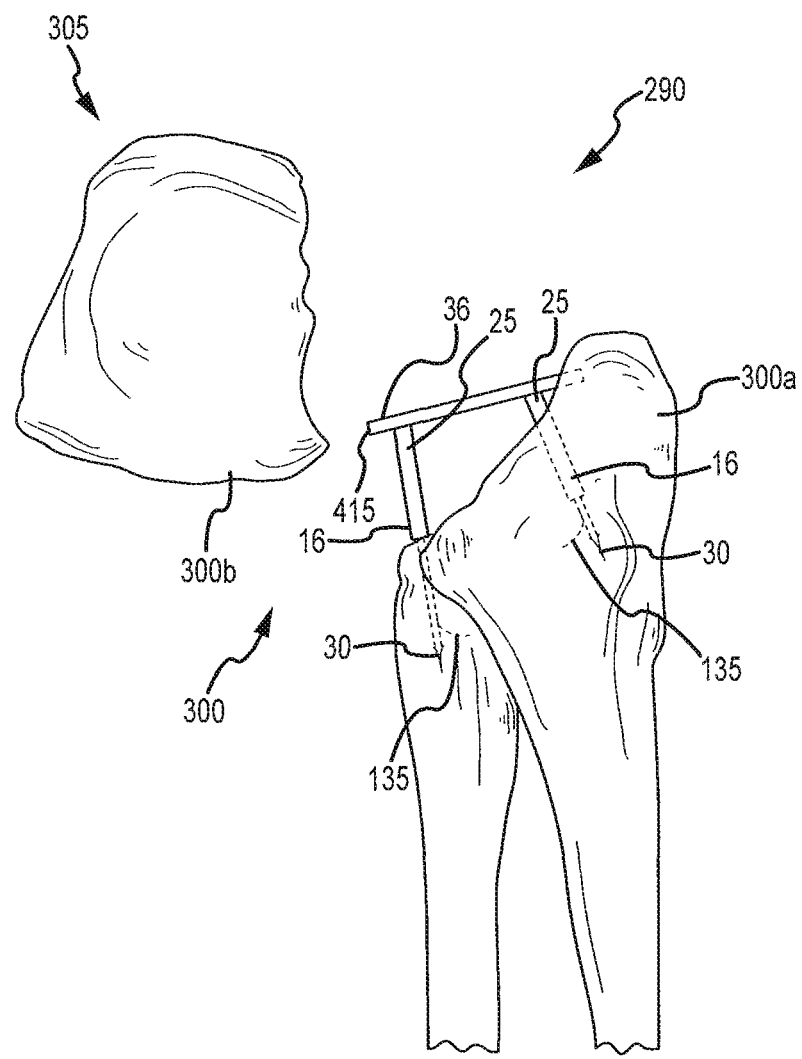
FIG. 35 is the same view as FIG. 34, except the anchors have been deployed on the proximal anchors.

As shown in FIG. 34, the connector ends 25 of the proximal intramedullary rods 16 are coupled to the holes 400 of the proximal plate 36 as shown in FIG. 29. The rods 16 may be passed through the holes 400 and driven into the trabecular bone, the rods 16 telescoping from the plate 36 until the free ends 30 interface with the cortical bone. As discussed above, the shape of the free ends 30 may be configured to indicate to the surgeon when the free ends 30 have fully interfaced with the cortical bone and configured to prevent over penetration. As depicted in FIG. 35 and previously described with respect to FIG. 28, the anchors 135 may then be deployed to prevent the rod 16 from pulling out. The anchors 135 may be spring loaded and configured as described above.

Figure 36:
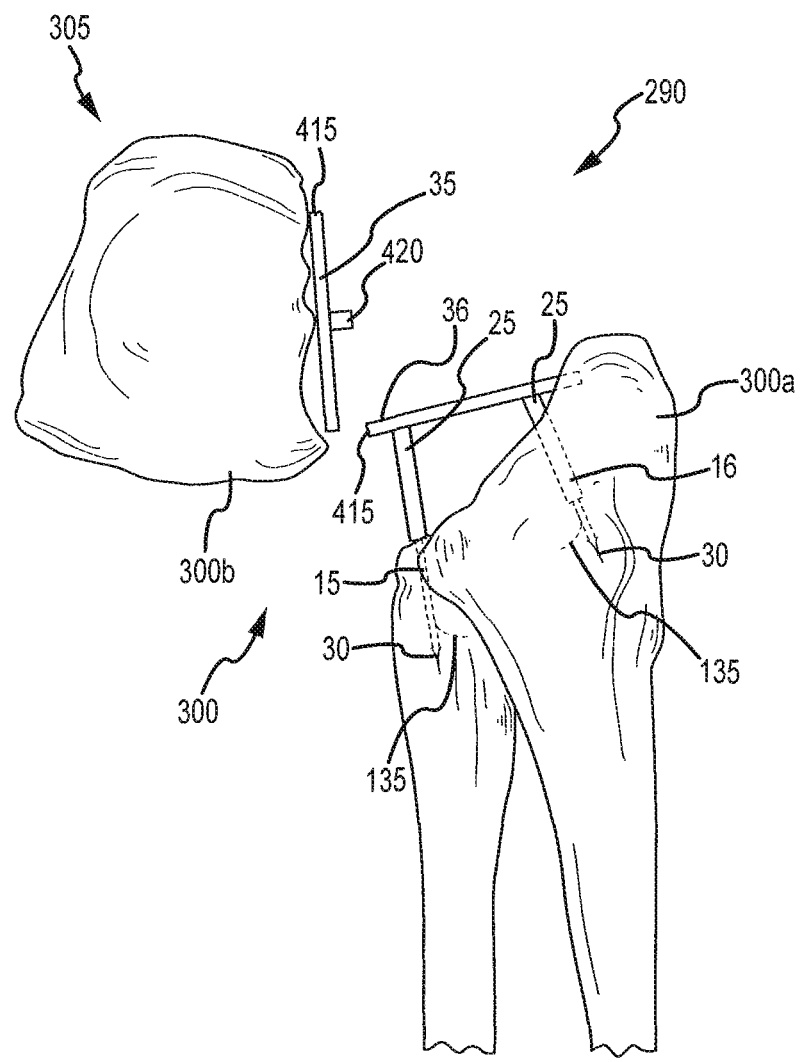
FIG. 36 is the same view as FIG. 35, except the distal plate has been implanted.

As shown in FIG. 36, the distal locking plate 35 may be press fit into the trabecular bone such that the plate 35 extends generally transverse to the axis of the bone 300 and a face of the plate 35 faces towards the fracture surface of the distal bone portion 300b. The plate 35 serves as a template for the distal rods 15. The angle of the plate 35 relative to the fracture surface of the distal bone portion 300b may require preoperative surgical planning.

Figure 37:
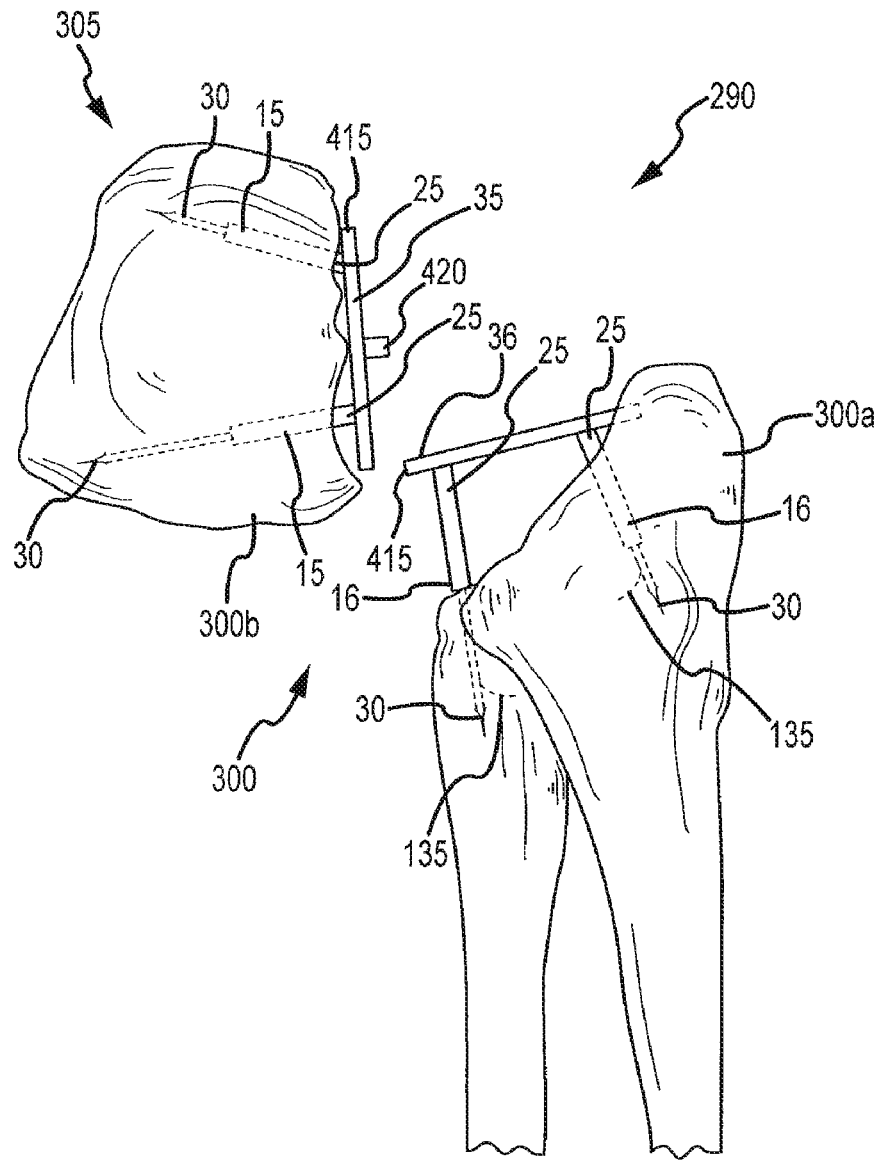
FIG. 37 is the same view as FIG. 36, except the distal intramedullary rods have been coupled to the distal plate and inserted into the distal bone portion.
Figure 38:
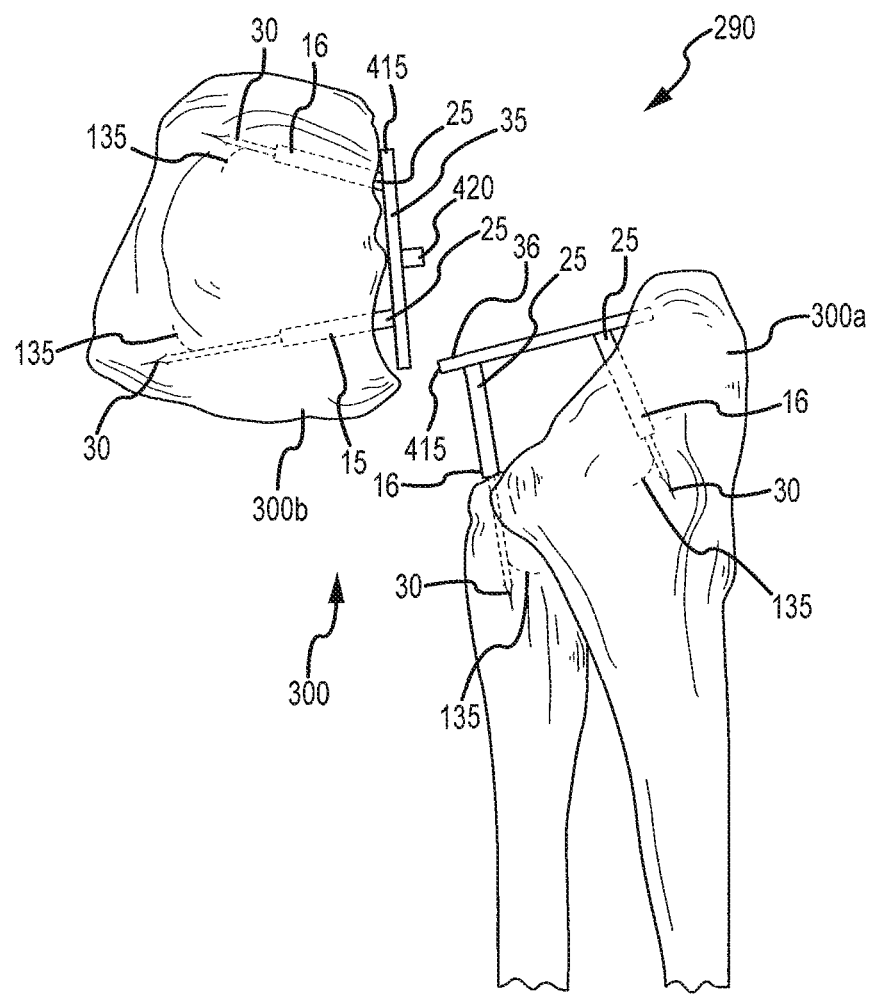
FIG. 38 is the same view as FIG. 37, except the anchors have been deployed on the distal anchors.

As shown in FIG. 37, the connector ends 25 of the distal intramedullary rods 15 are coupled to the holes 400 of the distal plate 35 as shown in FIG. 29. The rods 15 may be passed through the holes 400 and driven into the trabecular bone, the rods 15 telescoping from the plate 35 until the free ends 30 interface with the cortical bone. As discussed above, the shape of the free ends 30 may be configured to indicate to the surgeon when the free ends 30 have fully interfaced with the cortical bone and configured to prevent over penetration. As depicted in FIG. 38 and previously described with respect to FIG. 28, the anchors 135 may then be deployed to prevent the rod 15 from pulling out. The anchors 135 may be spring loaded and configured as described above.

Figure 39:
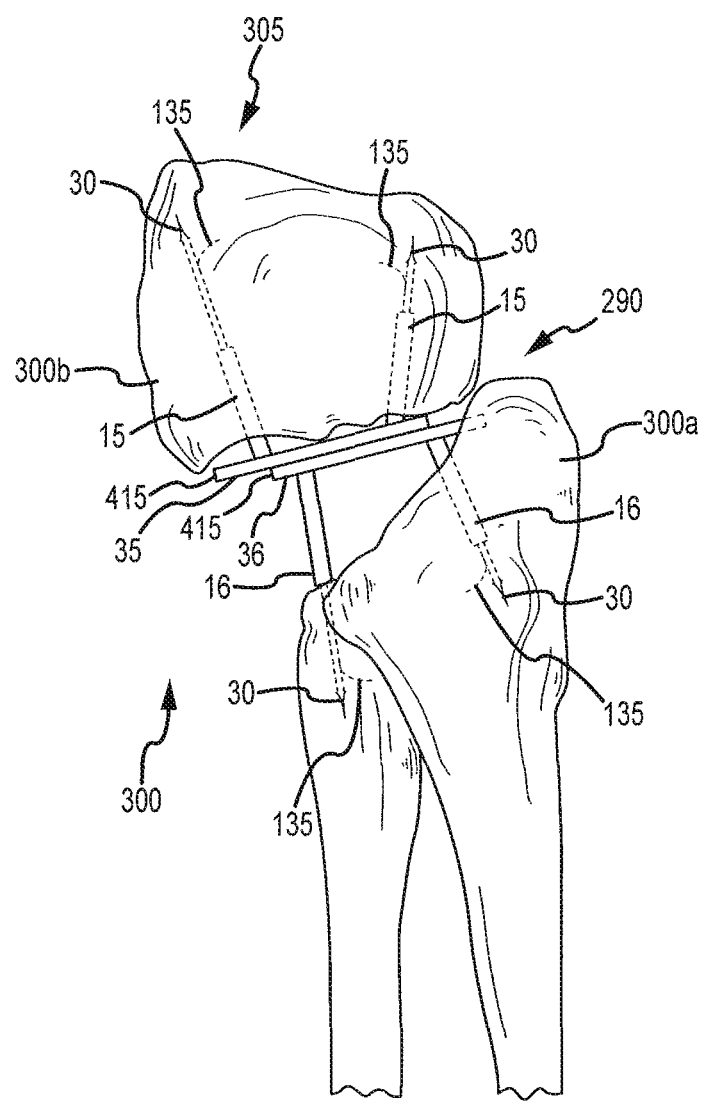
FIG. 39 is the same view as FIG. 38, except the plates and their respective bone portions are being moved into place for fixation of the plates to each other.
Figure 40:
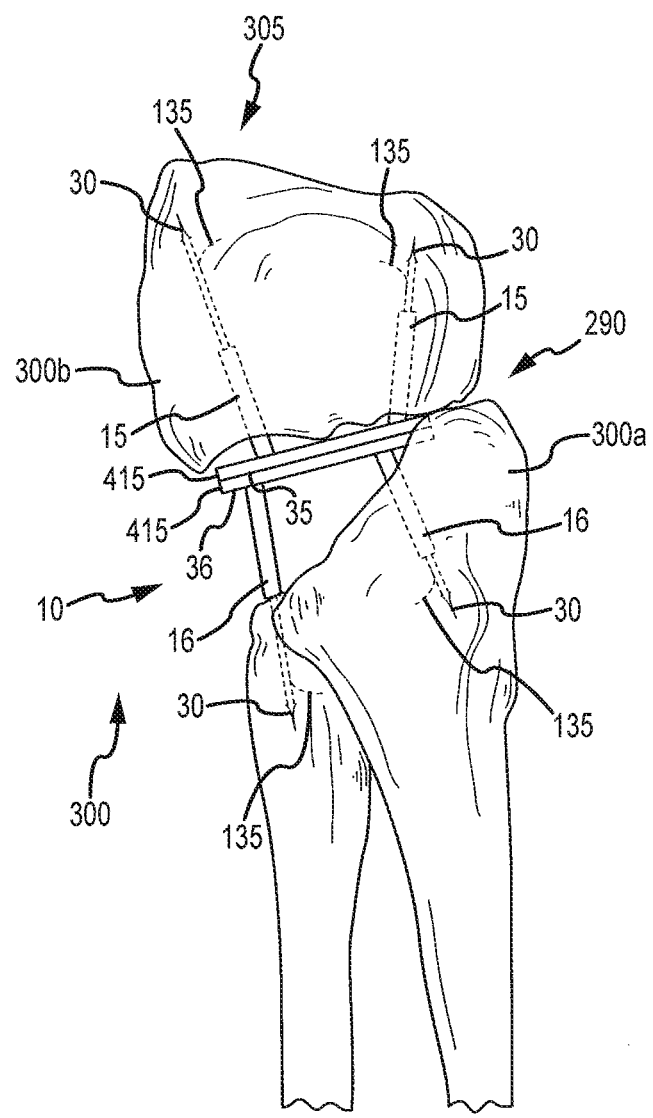
FIG. 40 is the same view as FIG. 39, except the plates have been joined to form a rigid integral implant assembly.
Figure 41:
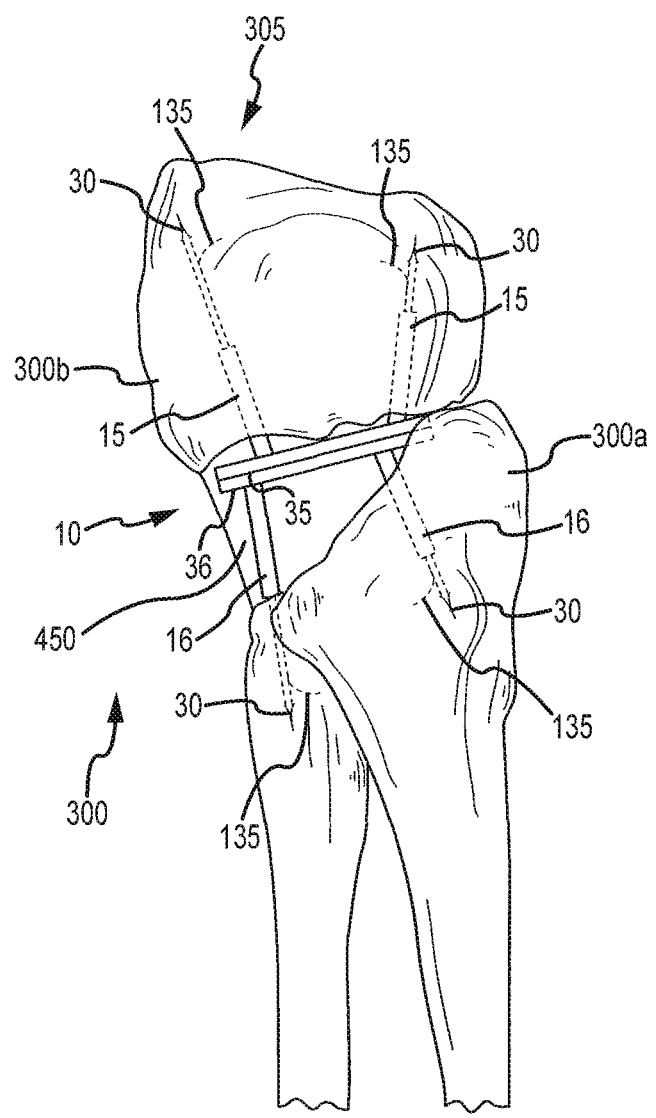
FIG. 41 is the same view as FIG. 40, except bone substitute material has been deposited in the fracture.

As shown in FIG. 39, the plates 35, 36 are placed face-to-face to cause the pin 420 to enter the slot 410 as depicted in FIG. 29. As depicted in FIG. 40, the plates 35, 36 are locked together when the pin 420 is received in the center hole 405 as illustrated in FIG. 30. The implant assembly 10 is now fully assembled into a rigid integral device that maintains the distal and proximal bone portions 300a, 300b in the desired positional relationship to each other via its distal and proximal rods 15, 16 that are coupled together via the distal and proximal plates 35, 36. Finally, as shown in FIG. 41, bone substitute may be added between the locking plates 35, 36 and the fracture surfaces to fill the void and improve stability. The bone substitute material will be remodeled as the bone heals.

All of the above mentioned steps, including the delivery of components of the implant assembly 10 and the assembly of the implant assembly 10 within the bone fracture 290 and interior of the bone 300, may be accomplished via a percutaneous or minimally invasive opening in the soft tissue neighboring the fracture 290 via minimally invasive surgical procedures and tools.

Figure 79:
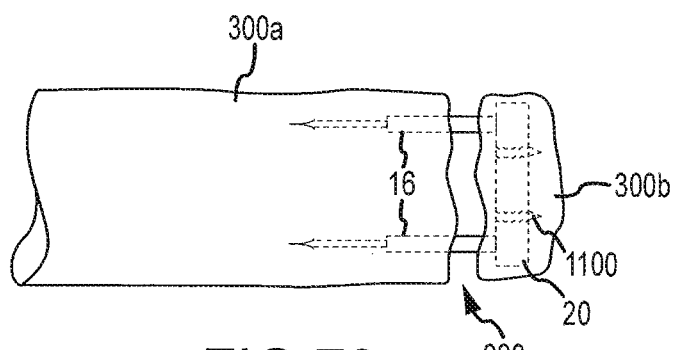
FIG. 79 is a plan view of the implant assembly implanted at a bone fracture, wherein the implant assembly employs a hub that engages the bone material.

While the embodiment depicted in FIGS. 30 and 40 illustrate the distal bone 300b and proximal bone portion 300a are held together via an implant assembly 10 having a hub 20 with distal rods 15 and proximal rods 16 respectively anchored in the distal and proximal bone portions, in other embodiments, the implant 10 may only employ proximal or distal rods, the hub 20 instead being adapted to engage bone material. For example, as shown in FIG. 79, which is a plan view of the implant assembly 10 implanted at a bone fracture 290, the hub 20 is configured to anchor to or engage with bone material on one side of the fracture 290 (e.g., on the distal bone portion 300b in the embodiment depicted in FIG. 79), and rods 16 extend into the bone portion 300a on the other side of the fracture 290. The hub 20 may be configured to be fit in a pocket in the proximal bone portion 300b by being placed generally transverse to the bone and/or generally parallel to the fracture 290. Alternatively or additionally, the hub 20 may be configured to receive anchoring members 1100, for example, bone screws 1100 that extend from the hub 20 into adjacent bone material of the distal bone portion 300b, securing the hub 20 to the distal bone portion 300b. Rods 16 proximally extend from the hub 20 in a manner as described above to anchor in bone material of the proximal portion 300a. The implant assembly 10 may then be employed to treat the fracture 290. While the embodiment discussed with respect to FIG. 79 is discussed with respect to the hub 20 being engaged with the distal portion 300b and the rods 16 being engaged with the proximal portion 300a, in other embodiments and types of fractures, the opposite will be true. Depending on the embodiment and the type of fracture, bone cement may be employed in place of or in addition to the screws 1100.

Depending on the materials forming the hub 20 and rods 15, the embodiments of the hub 20 and rods 15 employed, and the degree to which the rods 15 are gripped or otherwise attached to the hub 20, the assembled implant assembly 10 and various portions thereof may be generally rigid or fixed, semi-rigid or fixed, or generally flexible with respect to the implant assembly 10, the hub 20, the rods 15, elements of the hub 20 or rods 15, or connections between the various elements of the implant assembly 10.

In some embodiments, the implant assembly 10 may be assembled (partially or completely) within the bone and implanted within the bone (e.g., sub bone surface). In such embodiments, the implant assembly 10 may be said to function from the interior of the bone to the exterior of the bone. Depending on the bone and the way the implant assembly is implanted, in such embodiments, the implant assembly 10 may be said to act and/or extend along the axis of the bone in which it is implanted.

In other embodiments, the implant assembly 10 may be implanted so as to be partially within and outside the bone (e.g., partially sub bone surface and partially on the exterior of the bone). In yet other embodiments, the implant assembly 10 may be implanted so as to be generally completely on the outside of the bone (e.g., on the exterior of the bone).

Figure 77:
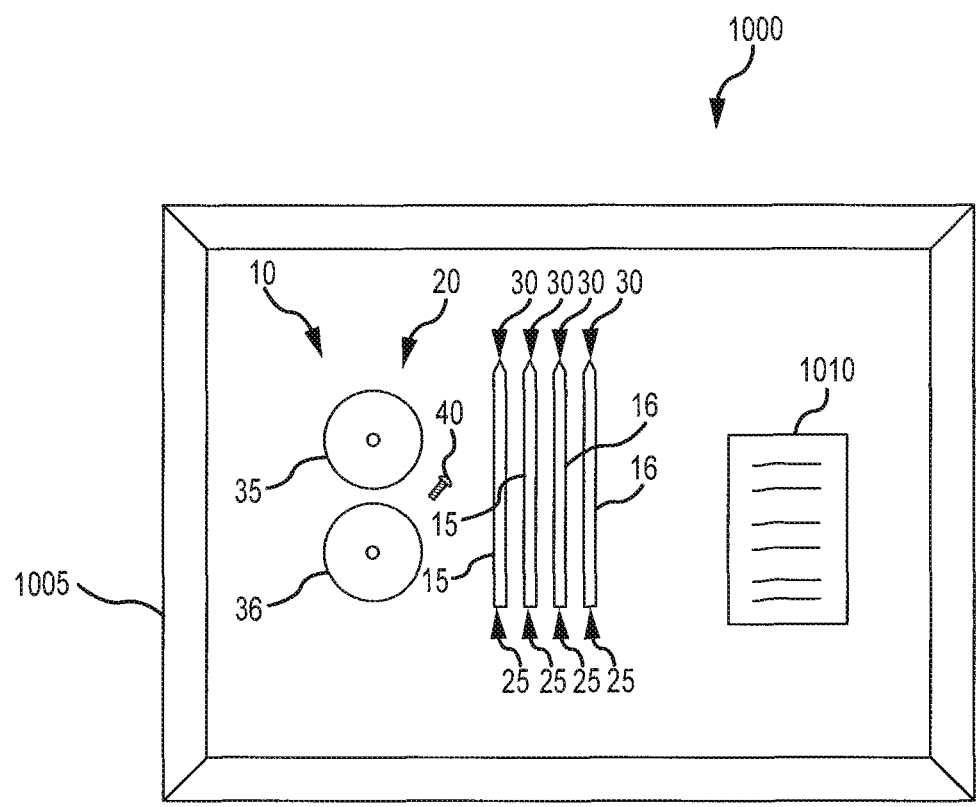
FIG. 77 is a plan view of a kit including the disassembled implant assembly and implantation instructions.

In some embodiments, as can be understood from FIG. 77, the implant assembly 10 may be provided in the form of a kit 1000. For example, the implant assembly components (e.g., the rods 15, 16, the plates 35, 36, and the screw 40 for joining the plates 35, 36) may be provided in a sterilized packaging 1005 along with instructions 1010 that explain the method of implantation as described above. Alternatively, the instructions 1010 may be provided via other methods, such as, for example, via the internet. The above mentioned implant assembly components may be provided in the kit 1000 in a fully assembled state (i.e., the implant assembly 10 is fully assembled), in a partially assembled state, or a fully disassembled state. The kit 1000 may include rods 15, 16 of a variety of fixed lengths or rods 15, 16 that are adjustable over a variety of possible lengths, thereby allowing the physician to select the length of rod needed for assembling the bone fracture via the implant assembly 10.

Figure 83A:
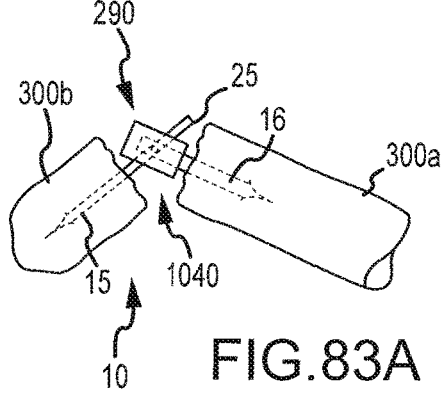
FIGS. 83A and 83B are side views of a fractured bone in which a snap plate equipped implant assembly is being deployed, wherein the snap plate may include two members that can move relative to each other along an axis and can be snapped into a final position and engagement with each other to provide fixation.
Figure 83B:
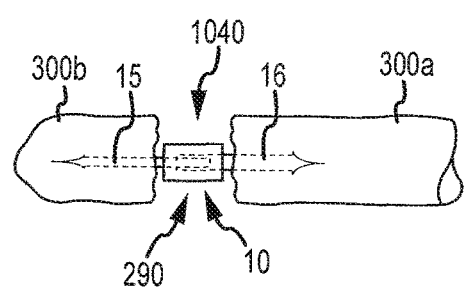

As indicated in FIG. 83A, which is a side view of a fractured bone, the implant assembly 10 may employ a snap plate 1040. One or more rods 15 may extend distally from the snap plate 1040 and be pivotally coupled thereto. One or more rods 16 may extend proximally from the snap plate 1040 and be fixedly coupled thereto. The implant assembly 10 may be delivered in pieces and assembled in the fracture 290 or delivered into the fracture essentially assembled. For example, as indicated in FIG. 83A, the bone portions 300*a*, 300*b* may be placed out of plane relative to each other and the pieces of the implant 10 may be placed in the bone portions. For example, the proximal rod 15 may be placed in the proximal bone portion 300*b*, the distal rod 16 may be placed in the distal bone portion 300*b* with the snap plate 1040 already coupled thereto or added in a subsequent step. Once the implant assembly 10 is fully located within the fracture 290 such that the proximal and distal rods 16, 15 are respectively coupled to the distal and bone portions 300*b*, 300*a* as shown in FIG. 83A, the connector end 25 of the proximal rod 15 may be received in the snap plate 1040 to couple the implant assembly 10 together as depicted in FIG. 83B. As can be understood from FIGS. 83*a* and 83B, the snap plate 1040 may be configured to allow the rods 15, 16 coupled thereto to move relative to each other along an axis to allow the rods 15, 16 to be snapped or otherwise received into the snap plate or each other, securing the rods in a final position with each other to provide fixation.

Although the present invention has been described with reference to preferred embodiments, persons skilled in the art will recognize that changes may be made in form and detail without departing from the spirit and scope of the invention.

What is claimed is:

1. A bone fracture repair device configured for placement directly between opposing pieces of a bone at a fracture site of the bone, the device comprising an at least partially intramedullary hub and at least two intramedullary rods radially extending from the hub to fix respectively within the two opposing pieces of the bone, wherein the hub is configured such that the rods are securable at selected, fixed radial positions over a range of selectable radial positions about a center axis of the hub, the rods are rigid and straight along their entire lengths from a proximal end connected to the hub to and through an interface tip of a distal fixation end and are configured to extend from an intramedullary portion of the hub at a slant with respect to a longitudinal axis of the bone receiving the device and entirely through a medullary cavity of the bone in order to embed interface tips of the fixation ends of the rods obliquely outward from the medullary cavity into a cortex of the bone without the fixation ends extending completely through the cortex, and the hub extends generally transverse to the longitudinal axis of the bone receiving the device at the bone fracture site.

2. The device of claim 1, wherein the selectable radial positions are incremental.

3. The device of claim 2, wherein the incremental selectable radial positions have increments of approximately five degrees.

4. The device of claim 1, wherein the hub is configured such that at least one of the rods is securable at a selected extension position over a range of selectable extension positions, the selected extension position being the extent to which the at least one of the rods extends beyond an edge boundary of the hub.

5. The device of claim 1, wherein at least one of the rods is configured to allow an overall length of the at least one of the rods to be adjusted.

6. A bone fracture repair device configured for placement between opposing pieces of a bone at a fracture site of the bone, the device comprising
a first intramedullary bone engagement member;
a second intramedullary bone engagement member; and
an at least partially intramedullary coupling member securing the first and second bone engagement members together in a variety of fixed angular relationships to each other about a center axis of the coupling member, the bone engagement members and the coupling member being configured for percutaneous delivery and intramedullary implantation by insertion directly between opposing sides of the fracture site, wherein
the first bone engagement member and the second bone engagement member are each rigid and straight along their entire lengths from a proximal end connected to the coupling member to and through an interface tip of a distal end and are configured to extend from an intramedullary portion of the coupling member at a slant with respect to a longitudinal axis of the bone receiving the device and entirely through a medullary cavity of the bone in order to embed the interface tips of the distal ends of the first and second bone engagement members obliquely outward from the medullary cavity into a cortex of the bone without extending completely through the cortex.

7. The device of claim 6, wherein the coupling member is configured to secure at least one of the bone engagement members in a variety of extents to which the at least one of the bone engagement members extends from the coupling member.

8. The device of claim 6, wherein at least one of the bone engagement members is configured to allow an overall length of the at least one of the bone engagement members to be adjusted.

9. The device of claim 6, wherein angular relationships between respective longitudinal axes of the engagement members is variable between approximately zero degrees and 180 degrees.

10. A bone fracture repair device configured for placement between opposing pieces of a bone at a fracture site of the bone, the device comprising
an at least partially intramedullary hub configured for insertion directly between opposing sides of the fracture site and extending generally transverse to a longitudinal axis of the bone receiving the device at the bone fracture site; and
an intramedullary rod that is connected to the hub at a proximal end, is straight and rigid along its entire length between the proximal end to and through an interface tip at a distal engagement end, and is configured to extend from an intramedullary portion of the hub at a slant with respect to the longitudinal axis of the bone receiving the device and entirely through a medullary cavity of the bone in order to embed the interface tip of the engagement end of the rod obliquely outward from the medullary space into a cortex of the bone without extending completely through the cortex, wherein
the hub is configured to allow the intramedullary rod to be coupled thereto in a selected fixed radial position over a range of selectable radial positions about a center axis of the hub extending over at least a portion of an edge boundary of the at least one hub.

11. The device of claim 10, wherein the selectable positions are incremental.

12. The device of claim 10, further comprising another intramedullary rod extending from the hub.

13. The device of claim 12, further comprising yet another intramedullary rod extending from the another intramedullary rod.

* * * * *